(12) United States Patent
Willins et al.

(10) Patent No.: US 7,241,613 B1
(45) Date of Patent: Jul. 10, 2007

(54) **IDENTIFICATION OF *CANDIDA* CELL SURFACE PROTEINS AND THEIR USES**

(75) Inventors: Debra A. Willins, Watertown, MA (US); Arturo J. Morales, Arlington, MA (US); Guillaume Cottarel, Cambridge, MA (US); Qiandong Zeng, Belmont, MA (US); Christina Alberti-Segui, Cambridge, MA (US)

(73) Assignee: Oscient Pharmaceuticals Corporation, Waltham, MA (US)

( * ) Notice: Subject to any disclaimer, the term of this patent is extended or adjusted under 35 U.S.C. 154(b) by 78 days.

(21) Appl. No.: 10/455,719

(22) Filed: Jun. 5, 2003

Related U.S. Application Data

(60) Provisional application No. 60/446,775, filed on Feb. 12, 2003, provisional application No. 60/385,568, filed on Jun. 5, 2002.

(51) Int. Cl.
C12N 1/00 (2006.01)
A61K 36/06 (2006.01)
C12P 21/04 (2006.01)
C07H 21/04 (2006.01)

(52) U.S. Cl. .................. 435/255.4; 435/6; 435/243; 435/252.3; 435/254.1; 435/254.22; 435/320.1; 435/69.1; 435/69.7; 424/274.1; 424/184.1; 530/300; 530/350; 536/23.1; 536/23.7

(58) Field of Classification Search .................. 435/6, 435/243, 252.3, 254.1, 254.22, 255.4, 320.1, 435/69.1, 69.7; 424/274.1, 184; 530/300, 530/350; 536/23.1, 23.7
See application file for complete search history.

(56) References Cited

U.S. PATENT DOCUMENTS 6,747,137 B1 * 6/2004 Weinstock et al. ......... 536/23.1

OTHER PUBLICATIONS

Burgess et al., The Journal of Cell Biology, 111:2129-2138, 1990.*
Mouyna, I., et al., "Identification of the catalytic residues of the first family of β(1-3)glucanosyltransferases identified in fungi", *Biochem J*, 347:(3) 741-747 (2000).
Weig, M., et al., "A *GAS*-like gene family in the pathogenic fungus *Candida glabrata*", *Microbiology*, 147:2007-2019 (2001).
Heinz, W.J., et al., "Molecular responses to changes in the environmental pH are conserved between the fungal pathogens *Candida dubliniensis* and *Candida albicans*," *Int J Med Microbiol*, 290:231-238 (2000) (Abstract).
Rodriguez-Pena, J.M., et al., "A Novel Family of Cell Wall-Related Proteins Regulated Differently during the Yeast Life Cycle," *Mol Cell Biol*, 20:3245-55 (2000).
Cormack, B., et al., "An Adhensin of the Yeast Pathogen *Candida glabrata* Mediating Adherence to Human Epithelial Cells," *Science* 285:578-582 (1999).
Navarro-Garcia, F. et al., "Virulence genes in the pathogenic yeast *Candida albicans*," *FEMS Microbiol. Rev.* 25:245-6 (2001).

* cited by examiner

*Primary Examiner*—Susan Ungar
*Assistant Examiner*—Padma Baskar

(57) ABSTRACT

The invention provides for novel polypeptides of *Candida* species found on the cell wall of the *Candida* organism. The invention further provides for methods of using these polypeptides, the genes encoding the polypeptides and fragments thereof for preparing antibodies, vaccines, therapeutic and diagnostic compositions.

2 Claims, 11 Drawing Sheets

An Ideal Cell Wall Protein

Analysis is biased, but not limited towards these proteins

Examples:

| GeneID | SignalPeptide | GPI | CYS | ST | Size |
|--------|---------------|-----|-----|-------|------|
| ALS1 | YES | 0 | 10 | 36.90 | 1260 |
| HYR1 | YES | 1 | 11 | 31.48 | 937 |
| PHR1 | YES | 1 | 14 | 20.44 | 548 |
| CHT2 | YES | 0 | 13 | 25.04 | 583 |
| HWP1 | Weak (1 TM) | 0 | 17 | 28.86 | 634 |

Construction of *C. albicans* null mutants
—— 3-way PCR ——

Construction of *C. albicans* null mutants
—— Gene disruption method ——

Sequences targeted in the first deletion using the ARG4 marker

Sequences targeted in the second deletion using the URA3 marker

Construction of *C. albicans* null mutants
——Verification PCR——

Filamentation assay

A.

B.

| Strains | Ability to form filament |
|---------|--------------------------|
| SC5314  | ++++ |
| BWP17   | +++  |
| als1    | ++   |
| hwp1    | +++  |
| mp65    | −    |
| pra1    | ++   |
| 6.3873  | ++   |
| 6.1231  | −    |
| sap9    | +    |
| 6.1639  | −    |

Adhesion assay

A.

B.

IDENTIFICATION OF *CANDIDA* CELL SURFACE PROTEINS AND THEIR USES

RELATED APPLICATIONS

This application claims the benefit of U.S. Provisional Application 60/385,568 filed Jun. 5, 2002 and U.S. Provisional Application 60/446,775 filed Feb. 12, 2003, the entire teachings of which are incorporated herein by reference.

SEQUENCE LISTING

Incorporated herein by reference in its entirety is a Sequence Listing, comprising SEQ ID NO: 1 to SEQ ID NO: 420. The Sequence Listing is contained on a CD-ROM, three copies of which are filed, the Sequence Listing being in a computer-readable ASCII file named "PATH03-12.txt", created on Jun. 3, 2003 and of 1,880 bytes in size, in IBM-PC Windows®NT v4.0 format.

FIELD OF THE INVENTION

A method of rapidly identifying cell surface proteins in *Candida* and cell surface proteins identified thereby. Proteins identified thereby can then be used to develop antibodies, vaccines, diagnostic kits, prophylactic compositions and compounds and anti-fungal drugs.

BACKGROUND OF THE INVENTION

The heterogeneous genus *Candida* belongs to the family Saccharomycetaceae with the Deuteromycetes (Fungi Imperfecti). The genus contains approximately 200 species, the number of which may change due to technological advances that will affect the current apparent taxonomic relationship perhaps leading to new species belonging to the genera.

The genus *Candida* is responsible for candidiasis and other conditions, some of which are lethal. In humans, the most common cause is *C. albicans*. However, other species are also responsible for candidiasis including *C. tropicalis, C. parapsilosis, C. guilliermondii, C. glabrata, C. dubliniensis* and *C. krusei*. For example, *C. tropicalis* accounts for about one third of all cases of deep candidiasis in neutropenic patients. Other medically important *Candida* spp. include *C. catenulata, C. ciferrii, C. haemlulonii, C. kefyr, C. lipolytica, C. lusitaniae, C. norvegensis, C. parapsilosis, C. pulcherrima, C. rugosa, C. utilis, C. viswanathii* and *C. zeylanoides*.

Species of *Candida* that are pathogenic for humans exist as benign commensals in their host organisms, in one or more body locations. As opportunistic pathogens, they are poised to overgrow cavities and penetrate tissue in response to an alteration in host physiology that presumable compromises the immune functions that normally suppress their growth.

*Candida albicans* is one species of *Candida*. It is normally a commensal organism that lives in different parts of the body. However, *C. albicans* is responsible for numerous common infections in humans including vaginal yeast infections, thrush (oral candidiasis), esophagitis, gastrointestinal candidiasis, cutaneous candidiasis, diaper rash, paronychia (nail fold infection), chronic mucocutaneous candidiasis, and life-threatening systemic infections. In fact, *C. albicans* is the leading fungal infection in immunocompromised patients and is also one of the leading infections in patients with long hospital stays and indwelling catheters. Such infections result in an estimated cost to hospitals of $34,000-$45,000 per patient and a national annual cost of $216-280 million dollars per year. As the number of immunocompromised patients increases, the amount of money spent annually will correspondingly also increase. The need is further compounded by the emergence of drug resistance of certain fungi to the existing drugs.

Another *Candida* species is *C. glabrata*. *C. glabrata* is regarded as a symbiont of humans and can routinely be isolated from the oral cavity and the genitourinary, alimentary and respiratory tract of most individuals. As an agent of serious infection, it has been associated with endocarditis, meningitis, and multifocal, disseminated disease.

Although the genomes of some organisms have been fully sequenced, the *Candida* genome has been not completed and publicly accessible portions present proteins which are not complete and contain errors. Development of genome-wide functional analysis in *C. albicans* has been hampered by the asexual and diploid nature of the organism. Moreover, there is still a need for the identification of reliable determinants of virulence (Navarro-Garcia et al., 2001 *FEMS Microbiol. Rev.* 25: 245-68). Also, some of these pathogens have become resistant to antifungal agents, especially triazole compounds.

As a consequence, methods of treating *C. albicans* are of growing importance. Thus new targets for treating *C. albicans* need to be identified. The invention disclosed herein provides a rapid method for identifying such targets, e.g., cell surface proteins, and the proteins identified thereby. The proteins thus identified can then be used to develop therapeutic, prophylactic and diagnostic antibodies, vaccines, drugs, diagnostic kits, and prophylactic compositions and compounds.

BRIEF SUMMARY OF THE INVENTION

It is an object of the invention to provide a method of identifying a cell surface protein of a microorganism comprising the method of identifying a polypeptide with two or more of the following characteristics: (a) 750 or more amino acids, (b) about 10 or more serine and threonine residues, (c) a GPI motif, (d) eight or more cysteines, or (e) a signal peptide domain. In a more specific embodiment, the microorganism is *Candida*.

Another embodiment of the invention provides for polypeptides obtained by the above methods. Examples of such polypeptides include but are not limited to SEQ ID NO:211-SEQ ID NO:420 or fragments thereof. These polypeptides and fragments thereof can be expressed in the form of a fusion polypeptide or an epitope-tagged polypeptide.

It is a further object of the invention to provide for nucleic acids which encode SEQ ID NO:211-SEQ ID NO:420. Preferably these nucleic acids include SEQ ID NO:1-SEQ ID NO:210.

In another embodiment, the invention provides for an antibody or immunogenic fragment thereof which binds to an epitope on a polypeptide discussed above. Such antibodies and immunogenic fragments include chimeric antibodies (including humanized antibodies), monoclonal antibodies, labeled antibodies, a bispecific antibodies or an immunogenic fragments of one of these antibodies.

Another aspect of the invention includes compositions comprising an antibody or immunogenic fragment and an antifungal agent. Preferred antifungal agents include amphotericin B, amphotericin B—lipid based nystatin, flucytosine, imidazoles, triazoles, ketoconazole, itraconazole, fluconazole, terbinafine, butoconazole, ciclopirox olamine, halopro-gin, tolnaftate, naftifine, butenafine, echinocandin B, a polyene antifungal antibiotic, undecylenic acid, benzoic acid, salicylic acid, propionic acid, caprylic acid, or potassium iodide.

In another aspect, the invention provides for a method of treating candidiasis in a subject comprising the step of administering the antibody or immunogenic fragment thereof described above. The antibody also can be administered with an antifungal agent.

It is a further aspect of the invention to provide for a method of preventing a *Candida* related infection in a subject comprising the step of administering an antibody or immunogenic fragment described above. The antibody also can be administered with an antifungal agent.

Another embodiment of the invention contemplates a method of detecting a *Candida* related infection in a subject comprising: obtaining a biological sample which is believed to contain *Candida* from said subject; and assaying said sample with an labeled antibody.

Another object of the invention is to provide a therapeutic or prophylactic composition for inhibiting or preventing a *Candida* related infection in a subject comprising a polypeptide or antigenic fragment thereof in a therapeutically or prophylactic effective amount, an adjuvant, and a carrier, wherein when said composition is administered to a subject conferring a therapeutic or prophylactic effect to said subject.

Yet another object of the invention provides for a composition for raising an immune response in a subject comprising a therapeutically effective amount of a polypeptide or an immunogenic effective amount of an antigenic fragment thereof, an adjuvant and a carrier.

In another aspect, the invention provides for a diagnostic composition which assays for the presence of a *Candida* species comprising an antibody or antigenic portion thereof as described above operably attached to a detectable label.

It is a further object of the invention to provide for a method of screening for compounds that inhibit a biological activity of a polypeptide described above comprising:
(A) preparing a cell which overexpresses or underexpresses a polypeptide of interest such that the cell is more resistant to a compound when the polypeptide is overexpressed and the cell is less resistant to the compound when the polypeptide is underexpressed;
(B) exposing the cell to a candidate agent when the polypeptide is overexpressed;
(C) determining whether the agent of interest inhibits virulence, biofilm formation, adhesion, or growth.

Alternatively the method of screening for compounds can be performed in vitro. The method would comprise steps such as:
(A) preparing an expression vector comprising a nucleic acid of interest which is operably linked to a suitable promoter;
(B) transforming the expression vector in to a host cell;
(C) culturing the host cell under conditions suitable for expression of the vector and the polypeptide encoded by the nucleic acid of interest;
(D) purifying the polypeptide;
(E) exposing the purified polypeptide to a compound; and
(F) determining whether the compound bound the purified polypeptide. This method could further comprise the step of determining whether the activity of the polypeptide is modulated by the compound. In this method the preferred host cell is a bacterium, a yeast, an insect cell or a mammalian cell.

Another aspect of the invention contemplates a probe or primer for diagnosing a subject with a *Candida* infection comprising a nucleic acid.

In yet another aspect, the invention provides for a drug obtained by the above methods.

DETAILED DESCRIPTION OF THE INVENTION

Figure 1:
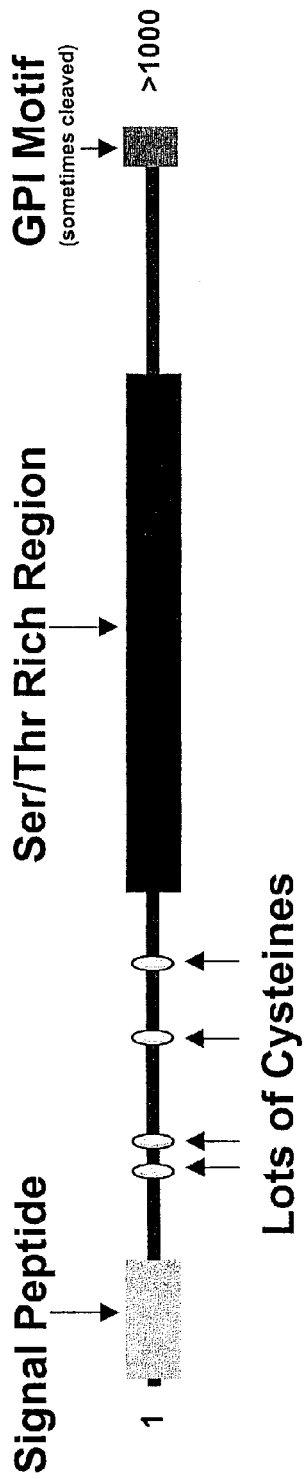
FIG. 1. An ideal *Candida* cell surface protein.
Figure 2:
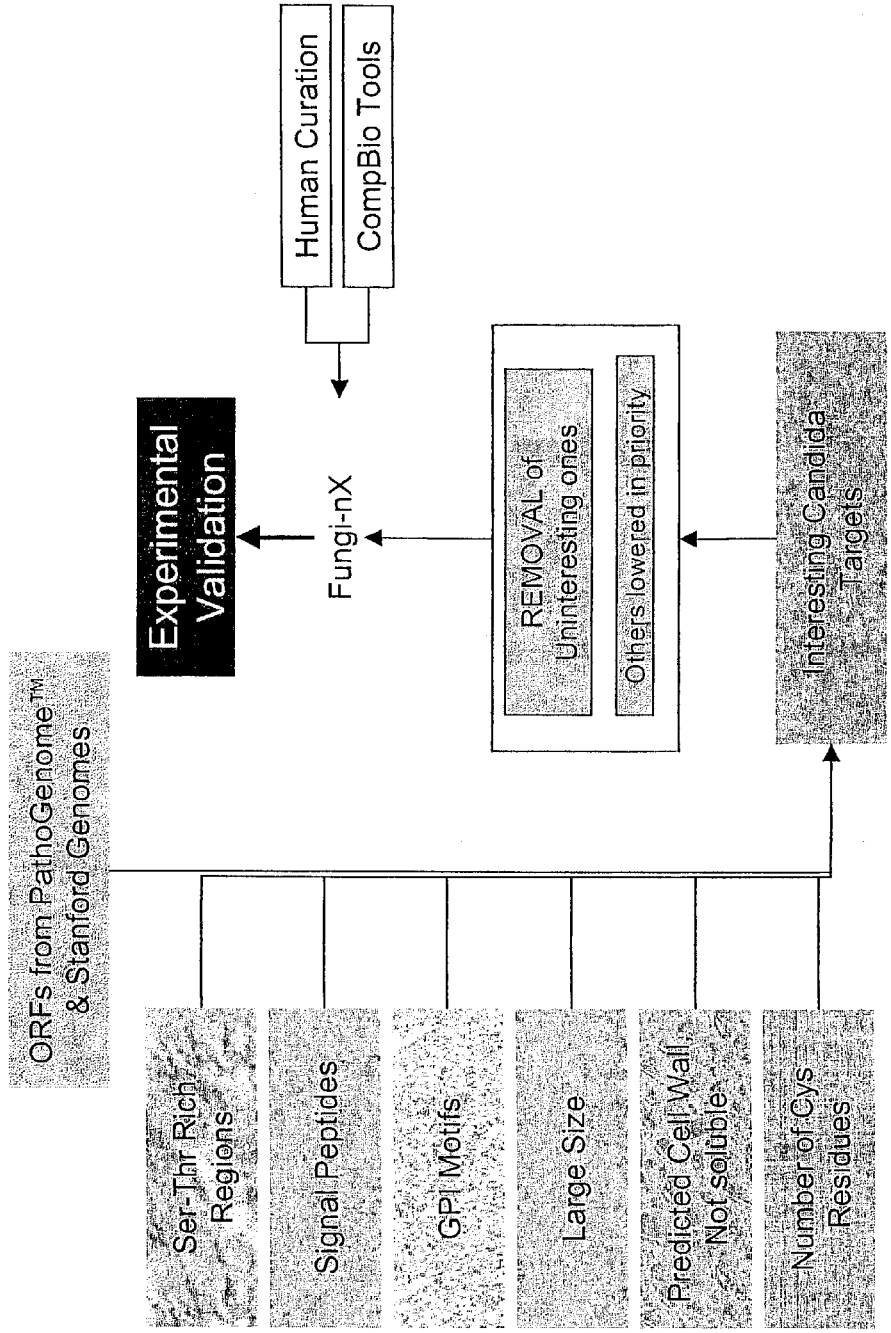
FIG. 2. Model of Genome-Wide Search. Open reading frames (ORFs) from PathoGenome™ and Stanford Genomes databases. Sequences greater than 1000 amino acids were first selected and then analyzed for whether they contained any of the following: serine-threonine rich domains, signal peptides for the cell membrane over signal peptides for other domains in the yeast organism, a GPI anchor motif, a cell wall localization signal, and a high content of cysteine residues. Based on these criteria, sequences encoding *Candida* proteins were selected for further experimental analysis. By "interesting" is meant higher priority.

Although the examples and discussions are discussed in terms of *Candida* and preferably *Candida albicans*, the embodiments described herein can be utilized with any microbial organism.

1. Definitions

By "*Candida*" is meant to include any species of *Candida*. Preferable species of *Candida* include *C. tropicalis, C. parapsilosis, C. guilliermondii, C. glabrata, C. dubliniensis, C. krusei, C. catenulata, C. ciferrii, C. haemlulonii, C. kefyr, C. lipolytica, C. lusitaniae, C. norvegensis, C. parapsilosis, C. pulcherrima, C. rugosa, C. utilis, C. viswanathii* and *C. zeylanoides*. Preferable species are those which cause candidemia in a subject. In a recent 2002 study, the Centers for Disease Control (CDC) identified the following relevant *Candida* species and isolates:

| *Candida* species | Percent Isolates |
|---|---|
| *C. albicans* | 45 |
| *C. glabrata* | 24 |
| *C. parapsilosis* | 13 |
| *C. tropicalis* | 12 |
| *C. krusei* | 5 |
| *C. dubliniensis* | |

See Hajjeh, "The Changing Epidemiology of Candidemia," 6th American Society for Microbiology *Candida* and Candidiasis Conference, Jan. 13-17, 2002, Tample, Fla.

By "individual" and "subject" are meant to include a vertebrate, preferably a vertebrate (e.g., fish, amphibian, avian, mammal and the like. More preferably, these terms are meant to be mammals. Mammals include, but are not limited to, farm animals, sport animals, and pets, e.g., murines, canines, felines, bovines, ovines, caprines, equines, porcines, rodents, and the like. Most preferred, the mammals are human.

By "biological sample" is meant a sample obtained from a subject. The sample includes but is not limited to blood, serum, hair, urine, tissue, and combinations thereof.

By "biological activity" is meant that the nucleic acid or the polypeptide of interest has a structural, regulatory and/or biochemical function of the naturally occurring sequence found in the *Candida* spp.

By "modulating" or "regulating" is meant the ability of an agent to alter from the wild type level observed in the individual organism the activity of a protein or nucleic acid of interest. The activity can be at the level of transcription, translation, nucleic acid or protein stability or protein activity.

By "vaccine" is meant a pharmaceutical composition for human or animal use, which is administered with the intention of conferring the recipient with a degree of specific immunological reactivity, or immune response, against a particular target, or group of targets. The immunological reactivity may be antibodies or cells (particularly B cells, plasma cells, T helper cells, and cytotoxic T lymphocytes and their precursors) that are immunologically reactive against the target or any combination thereof. Immunological reactivity may be desired for experimental purposes, for treatment, or for the elimination of a particular substance.

By "antibody" (interchangeably used in plural form) is meant an immunoglobulin (Ig) molecule capable of specific binding to a target, such as a polypeptide, through at least one antigen recognition site, located in the variable region of the immunoglobulin molecule. An antibody can be from any source of animal capable of producing them, for example, mouse, rat, rabbit, or human antibodies. As used herein, the term encompasses not only intact antibodies, but also fragments thereof (such as Fab, Fab', F(ab')$_2$, Fv, single chain (ScFv)), mutants thereof, fusion proteins, chimeric antibodies (e.g., humanized antibodies, primatized antibodies and the like), and any other modified configuration of the immunoglobulin molecule that comprises an antigen recognition site of the required specificity. The term "antibody" includes polyclonal antibodies and monoclonal antibodies. The term "antibody" can refer to any of the major vertebrate immunoglobulin classes, such as IgA, IgD, IgE, IgG, or IgM, as well as subclasses thereof (e.g., IgG1, IgG2 and the like). Antibodies of the invention may be isolated from a hybridoma cell, the serum of a vertebrate, recombinant eukaryotic or prokaryotic cells transformed with antibody coding sequences, including plant cells, ascites fluid, bovine milk, or the like.

"Immunological recognition" or "immunological reactivity" refers to the specific binding of a target through at least one antigen recognition site in an immunoglobulin or a related molecule, such as a B cell receptor or a T cell receptor.

The term "antigen" refers to the target molecule that is specifically bound by an antibody through its antigen recognition site. The antigen may, but need not be chemically related to the immunogen that stimulated production of the antibody. The antigen may be polyvalent, or it may be a monovalent hapten. Examples of kinds of antigens that can be recognized by antibodies include polypeptides, polynucleotides, other antibody molecules, oligosaccharides, complex lipids, drugs, and chemicals. The specific portion of the antigen or immunogen which is bound by the antibody is termed the "binding epitope" or "epitope."

An "immunogen" is an antigen capable of stimulating production of an antibody when injected into a suitable host, usually a mammal. Compounds may be rendered immunogenic by many techniques known in the art, including cross-linking or conjugating with a carrier to increase valency, mixing with a mitogen to increase the immune response, and combining with an adjuvant to enhance presentation. The term is used interchangeably with "antigen".

The term "epitope" refers to the site on an antigen or hapten to which a specific antibody molecule binds or is recognized by T cells. The term is also used interchangeably with "antigenic determinant" or "antigenic determinant site."

The terms "immunogenic polypeptide" and "immunogenic amino acid sequence" refer to a polypeptide or amino acid sequence, respectively, which elicit antibodies that neutralize viral infectivity, and/or mediate antibody-complement or antibody dependent cell cytotoxicity to provide protection of an immunized host. An "immunogenic polypeptide" as used herein, includes the full length (or near full length) sequence of the desired protein or an immunogenic fragment thereof.

By "immunogenic fragment" is meant a fragment of a polypeptide which includes one or more epitopes and thus elicits antibodies that neutralize viral infectivity, and/or mediates antibody-complement or antibody dependent cell cytotoxicity to provide protection of an immunized host. Such fragments will usually be at least about 5 amino acids in length, and preferably at least about 10 to 15 amino acids in length. There is no critical upper limit to the length of the fragment, which could comprise nearly the full length of the protein sequence, or even a fusion protein comprising fragments of two or more of the antigens. The term "treatment" as used herein refers to treatment of a mammal, such as bovine or the like, either (i) the prevention of infection or reinfection (prophylaxis), or (ii) the reduction or elimination of symptoms of an infection. The vaccine comprises the recombinant BAV itself or recombinant antigen produced by recombinant BAV. An "immunological response" to a composition or vaccine is the development in the host of a cellular and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

By "fragment" is meant a fragment of a nucleic acid, antibody or polypeptide as described herein. Preferably the fragment has a biologic and/or immunogenic activity.

By "epitope-tagged polypeptide" is meant a polypeptide sequence wherein a nucleic acid encoding the polypeptide of interest has been fused to a second nucleic acid sequence which encodes a well characterized epitope that is recognized by commercially available antibodies or other antibodies of interest. A well characteractized epitope includes, but is not limited to myc, hemagglutinin (HA), vesicular stomatitis virus (VSV) epitopes or FLAG epitopes. See, e.g., Antoni et al., 2000 *Gene* 246: 179-85.

By "purified" or "isolated" are meant to refer to molecules (e.g., nucleic acids or polypeptides), that removed from their natural environment and isolated or separated from at least one other component with which they are naturally associated.

By "nucleic acid" is meant to include RNA and DNA both single stranded and double stranded (i.e., ssRNA, dsRNA, ssDNA and dsDNA), cDNA, antisense strands of nucleic acids, small hairpin RNAs (i.e., shRNA), inhibitory RNAs (i.e., iRNAs or siRNAs), oligonucleotide, nucleotide and polynucleotide sequences, genes and fragments thereof. The nucleic acid can be genomic or synthetic in origin, and preferably encodes a protein found in a species of *Candida*.

By "functional variant" is meant a nucleic acid that encodes a polypeptide that has at least 80% sequence similarity to the wild-type polypeptide sequence and which shares a biological activity as the wild-type polypeptide sequence. Preferably, the variant is at least 85%, 90%, or 95% similar to the wild-type polypeptide sequence and shares one or more biological activities of the wild-type polypeptide sequence. "Functional variant" is meant to include "functional derivative", "fragments", "analogs", and "homologs" as they may relate to polypeptides and nucleic acids of interest.

The term "protein" is used herein to designate a polypeptide or glycosylated polypeptide, respectively, unless otherwise noted. The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like. Preferably the proteins of interest are *Candida* proteins.

"Fusion protein" is usually defined as the expression product of a gene comprising a first region encoding a leader sequence or a stabilizing polypeptide, and a second region encoding a heterologous protein. It involves a polypeptide comprising a protein fragment preferably with a biological activity (e.g., antigenic activity, enzymatic activity and the like) or a full length protein of interest as well as (a) heterologous sequence(s), typically a leader sequence functional for secretion in a recombinant host for intracellularly expressed polypeptide, or an N-terminal sequence that protects the protein from host cell proteases, such as SOD. An antigenic protein fragment is usually about 5-7 amino acids in length.

By "modification" as it relates to a chemical modification (e.g., addition of a fatty acid, sugar moiety, or other alteration on a polypeptide or a methylation, for example on a nucleic acid). Preferably the modification does not unnecessarily alter the biological activity of the nucleic acid or the polypeptide.

By "antifungal agent" is meant an agent, such as a chemical compound, extract (e.g., plant or herbal composition) which has a modulatory activity on a *Candida* spp. gene or polypeptide encoded by a *Candida* spp. gene, wherein the modulatory activity inhibits or prevents the *Candida* growth, infection, virulence, and the like.

By "therapeutically effective amount" is meant that amount of drug or pharmaceutical agent that will elicit the biological or medical response of a tissue, system or animal that is being sought by a researcher or clinician. Likewise, by "prophylactically effective amount" is meant that amount of drug or pharmaceutical agent that will elicit the biological or medical response of a tissue, system or animal that is being sought by a researcher or clinician (e.g., prevention or inhibition of the onset of a *Candida* infection).

The terms "label" or "labeled" refers to incorporation of a detectably marker, e.g., by incorporation of a radiolabeled amino acid or attachment to a polypeptide of biotinyl moieties that can be detected by marked attachment to a polypeptide of biotinyl moieties that can be detected by marked avidin (e.g., streptavidin containing a fluorescent marker or enzymatic activity that can be detected by optical or colorimetric methods). Various methods of labeling polypeptides and glycoproteins are known in the art and may be used. Examples of labels for polypeptides include but are not limited to: 3H, C14, 35S, 125I, 135I, fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, metal binding domains, epitope tags and the like). Radioactive labels and fluorescent labels can similarly be used to label nucleic acids of interest for use as probes and primers.

2. Methods of Identifying Cell Wall Proteins

Cell wall proteins are useful targets in preparing drugs, antibodies and diagnostics for prophylactic treatment and therapy relating to *Candida* infections. Additionally, such proteins or polypeptide fragments thereof may be used to prepare vaccines to prevent *Candida* infection. Such polypeptides or fragments can be used either alone or in combination with other *Candida* cell wall polypeptides.

These cell wall polypeptides can be derived from sequences previously identified in the literature, which may or may not have been fully characterized and which may or may not have annotation suggesting that the proteins would localize to the cell wall. Alternatively, as the *Candida* genome has not been fully sequenced and characterized to date, sequences can be identified based on partial sequences deposited in the various international *C. albicans* databases (e.g., PathoGenome™ Database (www.genomecorp.com), Stanford Genome databases, GenBank, EST databases, cDNA databases, TIGR database, and the like). Of particular interest are proteins with specific features associated with cell wall proteins, whether selected directly from *C. albicans* sequences or found by homology between *C. albicans* sequences and proteins with these features from other fungi, especially *S. cerevisiae*. The proteins identified by these methods would not typically fall within a class of proteins essential to the cell growth.

In the event that cell wall proteins that are essential for *Candida* growth are identified, these would become candidates for the development of antifungal drugs. Either cell-based or cell-free assays would be designed to screen for compounds that bind the protein of interest or affect its function. For example, screening could be done in a cell-based assay by preparation of strains over-expressing the protein of interest and comparing the effect of compounds on the growth of the over-expression strain as compared to a wild-type strain. If the compound inhibited the activity of the protein of interest (or proteins in the same functional pathway), over-expression of the protein may moderate the effect of the compound (make the cells somewhat resistant to the compound). Alternatively, a cell-based assay could be designed to detect hypersensitivity to the compound of cells under-expressing the gene of interest (e.g., heterozygous mutants, conditional-lethal mutants, or transcriptionally-repressed mutants). Another method of screening for compounds that affect the protein of interest would be to screen in vitro for compounds that bind the protein of interest (e.g., by capillary electrophoresis, surface plasmon resonance, thermal denaturation, scintillation proximity, or similar assays). Such compounds would ideally be screened further to determine if they had any effect on the function of the protein of interest. And finally, if the protein of interest has a biochemical activity that can be assayed directly or through use of an appropriate reporter gene fusion, compounds could be screened for those that inhibit the activity of interest. Compounds that inhibit the protein of interest generated by any of these screening methods would be excellent candidates for antifungal drugs. In particular, if the target is found by further experimentation (as discussed infra) to be exposed on the outer surface of the cell wall, such drug candidates would have an advantage over other drug candidates because their action would not be limited by their ability to penetrate to the interior of the cell.

2.1 Cell Wall Motifs

Determination of cell wall proteins will be based on the presence of certain motifs that typify cell wall proteins. These include: glycosyl phosphatidyl inositol (GPI) anchor motifs, the length or size of the protein (i.e., number of amino acids), serine-threonine rich domains, and cysteine rich domains. Cell wall proteins can also be identified by the absence of non-cell wall protein motifs. Such motifs include, but are not limited to nuclear localization signals, DNA binding signals, RNA binding signals, and mitochondrial targeting signals. The motifs will be analyzed based on their convergence (e.g., the presence of 4 cell wall motifs is better than three motifs, which is better than two motifs and so forth).

2.1.1 Glycosyl Phosphatidyl Inositol (GPI) Anchor Motifs

In fungi, and a variety of eukaryotes including mammals, many proteins that localize to the cell surface have recognizable sequence features of a GPI protein. A GPI protein comprises an N-terminal signal sequence, a C-terminal hydrophobic sequence, and a short omega-sequence located upstream of the hydrophobic sequence. The GPI moiety is pre-assembled in the endoplasmic reticulum (ER) in a series of enzymatic steps from phosphatidyl inositol, N-acetyl-glucosamine, mannose, and phosphoethanolamine components. The protein receiving the GPI modification is imported into the ER, cleaved at the omega site, and the GPI moiety is added as a block by a transamidase, which replaces the C-terminus of the protein with the GPI moiety. The GPI proteins get additional modifications as well, and proceed through the ER and Golgi bodies, finally being transported to the cell membrane. In fungi, some GPI proteins remain on the cell membrane and some are modified further. For example, the GPI moiety is cleaved off and the protein is linked to the β-1,6-glucan of the cell wall (this class of proteins has a slightly different version of the GPI sequence motif) (Hamada et al., 1998a *Mol. Gen. Genet.* 258: 53-9; Hamada et al., 199b *J. Biol. Chem.* 273: 26946-53; Hamada et al., 1999 *J. Bacteriol* 181: 3886-89; and Caro et al., 1997 *Yeast* 13: 1477-89).

GPI proteins are of interest because approximately 65% of *S. cerevisiae* GPI proteins are observed in the cell wall and because the majority of *C. albicans* proteins linked to the cell wall appear to be GPI proteins. Additionally, two of three known *Candida* adhesins are GPI proteins and are important in virulence.

2.1.2 Size

Most preferred are the proteins that comprise 1,000 amino acids or more, as that length typifies proteins which are long enough to be exposed on the outside of the cell wall. Such polypeptides and proteins can also be utilized to prepare antibodies or immunogenic fragments thereof. Proteins are considered which contain about 500 or more amino acids. More preferred are proteins which contain 750 or more amino acids. More preferred still are proteins with 900 or more amino acids.

2.1.3 Serine-Threonine Rich Domains

Serine and threonine rich domains can be modified by O-glycosylation, which is implicated by the protein having an extended rod-like conformation. This may be important in extension of the functional domain of the polypeptide above the cell surface (Jentoft, 1990; *Trends Biochem. Sci.* 15: 291-4; and Tennissen et al., 1993 *Yeast* 9: 423-7). Preferred proteins will contain serine-threonine (ST) rich domains of about 10 to about 50 serines and threonines. More preferably, there will be about 20 to 50 serines and threonines. It is necessary that there be at least one tract of amino acids which is 30-60 amino acid residues and of which about 30 to about 50 percent of those residues are either a serine or a threonine (Jentoft, 1990).

2.1.4 Cysteine Rich Domains

Preferred polypeptides will contain eight or more cysteine residues over the length of the polypeptide. More preferred proteins will comprise 10 or more cysteine residues. Most preferred will be those proteins that contain 12 or more cysteine residues. For a discussion on the relevance of cysteine rich domains, see for examples, Molloy et al., 1995

Exp. Mycol. 19: 178-85; Shen et al., 2001 J. Biol. Chem. 276: 15768-75; Wojtaszek et al., 1997 FEBS Lett. 405: 95-8; and Thompson et al., 1970 J. Microsc. 91: 87-98.

However, not all proteins identified will contain cysteine rich domains. For example, the following proteins in Table 1.

TABLE 1

Proteins Without Cysteine Rich Domains

| Identifier | SEQ ID NO | Comments |
|---|---|---|
| 6.1231 | 290 | Protein with high similarity to S. cerevisiae Crh1p, which is a cell wall protein, member of the glycosyl hydrolase 16 family, which hydrolyze glycosidic bonds between two or more carbohydrates or between a carbohydrate and a non-carbohydrate moiety. |
| 6.2929 | 321 | Protein with a high similarity to a region of C. albicans Rbt1p, which may have a role in virulence and transcriptionally repressed by Tup1p. |
| 6.3969 | 345 | Protein with similarity to S. cerevisiae Ecm33p, which is involved in cell wall structure or biosynthesis and to S. cerevisiae Sps2p, which is involved in the middle/late stage of sporulation. |
| 6.6348 | 378 | Protein with moderate similarity to a region of S. cerevisiae Plb3p, which is a phospholipase B. |
| 6.7314 | 386 | Protein that shares identity with C. albicans Sap9p, which is a secreted aspartyl proteinase, member of the aspartyl (acid) protease family of peptidases. |
| 6.7956 | | Protein with low similarity to a region of murine Selp1, which is a P-selectin glycoprotein ligand that binds Selp and is important for adhesive interactions between circulating leukocytes and endothelial cells. |

For those proteins indicated as having low similarity, the degree of similarity to another protein is not necessarily relevant as long as other sequence properties exist (e.g., cysteine rich, serine and threoine rich and the like)

As will be discussed further below, the polypeptides of the invention do not require all the motifs to be cell wall proteins. In fact, those which lack some motifs and have others may still be cell wall proteins. Such proteins are nevertheless good targets for drug development.

2.1.5 Non-Cell Wall Motifs

Identification of cell wall proteins will also be aided by assessing polypeptides for the presence of non-cell wall motifs as well as the presence of cell-wall motifs. Polypeptides with more cell wall motifs than non-cell wall motifs, or those that lack non-cell wall motifs, will be weighted higher than those proteins with non-cell wall motifs, such as nuclear targeting domains. Proteins without any cell wall motifs and with only non-cell wall motifs will be discounted entirely and not further examined.

2.2 Types of Cell Wall Proteins

Based on what is known in S. cerevisiae and Candida, the following categories of cell wall proteins are likely targets for preparation of vaccines, drugs, antibodies, prophylactics and diagnostics. Preferably, these proteins include virulence factors and adhesion factors. Virulence factors include host recognition biomolecules (adhesions), morphogenesis related proteins (e.g., proteins involved in the reversible transition between unicellular yeast cells and filamentous growth forms), secreted aspartyl proteases and phospholipases (Calderone et al., 2001 Trends Microbiol. 9: 327-35).

Preferred adhesion factors include adhesins, hyphal specific cell wall proteins, 1,3-β-glucanosyltransferases and other proteins involved in carbohydrate metabolism and in cell wall maintenance; proteins involved in morphogenesis, filamentation and virulence; hydrolases (e.g., chitinase 2), proteinases, mannoproteins, mating response or agglutination proteins, β-glucanases and the like.

Identification of these proteins will preferably be in C. albicans, the most common of the human Candida pathogens. However, identification and use of these proteins (e.g., to prepare vaccines, drugs, antibodies and diagnostics) from other Candida species is also contemplated. The likelihood that proteins identified from Candida albicans will also be good targets in other species of Candida will depend on their degree of conservation. Based on a phylogenic tree of Candida, it would be expected that certain proteins from C. albicans would be more closely related to C. tropicalis and C. parapsilosis. Refer to the phylogenetic tree below for Candida and its relationship to Saccharomyces, Kluyveromyces and filamentous fungi. For additional information regarding the phylogenetic relationship of Candida, see for examples Barnes et al., 1991 J. Bacteriol. 173: 2250-5; Kurtzman et al., 1997 J. Clin. Microbiol. 35: 1216-23; and Hendriks et al., 1991 J. Gen. Microbiol. 137: 1223-30; and http://alces.med.umn.edu/candida/taxonomy.html.

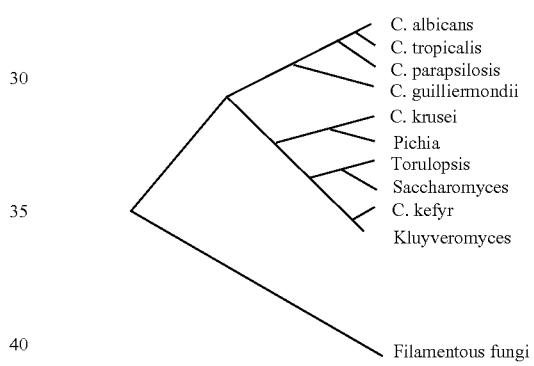

Candida glabrata used to be called Torulopsis glabrata 2.2.1 Adhesins, Biofilms and Virulence Factors Adhesins encompass a wide variety of different proteins including mannoproteins (Fukazawa et al., 1997 J. Med. Vet. Mycol. 35: 87-99), ALS proteins (see below), extracellular matrix (ECM) adhesins including ALA1 (Gaur et al., 1997 Infect. Immun. 65: 5289-94), mannan adhesins (Han et al., 1995 Infect. & Immun. 63: 2714-9), EPA1 of C. glabrata (Cormack et al., 1999 Science 285: 578-2), and HWP1 (Sundstrom 1999 Curr. Opin. Microbiol. 2: 353-7; Gale et al., 1996 Proc. Natl. Acad. Sci. USA 93: 357-61; Gale et al., 1998 Science 279: 1355-8; Buurman et al., 1998 Proc. Natl. Acad. Sci. USA 95: 7670-5).

In the instance of mannan adhesins, liposome-encapsulated yeast cell adhesin (L-adhesin) was shown to induce in mice a protective response against disseminated candidiasis. Antibodies specific to the adhesin fraction were at least partially responsible for the protection (Han et al. 1995).

Biofilms are the most common mode of microbial growth in nature and are also important in clinical infections especially due to the high antibiotic resistance associated with them. Biofilm formation is especially important with regard to biomedical devices (e.g., catheters) and denture stomatitis. Thus, biofilms play a role in both superficial and systemic candidiasis and the inability of current antifungal therapy to cure such diseases. Biofilm formation has been proposed to be a highly complex phenomenon (Chandra et al., 2001 *J. Bacteriol.* 183: 5385-94). Biofim formation likely involves the differential expression of proteins by *Candida* which may or may not be expressed during for regular adhesion of a *Candida* cell to a host cell.

2.2.2 ALS Genes

ALS (agglutinin-like sequence) genes of *C. albicans*, encode large cell surface glycoproteins, which are implicated in the process of adhesion to host surfaces. They are classified as one type of adhesin protein. These cell surface proteins are described as having a three-domain structure. They each have a relatively conserved N-terminal domain, a central domain consisting of a tandemly repeated motif, and a serine-threonine-rich C-terminal domain that is relatively variable across the family (Hoyer et al., 2001 *Yeast* 18: 49-60).

Several ALS genes have been identified in *C. albicans* including ALS1, ALS2, ALS3, ALS4, ALS5, ALS6, ALS7, ALS8 and ALS9 (Hoyer et al., 1998 *J. Bact.* 180: 5334-43; Hoyer et al., 2000 *Yeast* 16: 847-55; Hoyer, 2001 *Trends Microbiol.* 9: 176-180). Some are hypha-specific (i.e., expressed in the hyphal or filamentous growth form of *Candida*) such as ALS3 and some are not (e.g., ALS1).

The ALS1 genes of *C. albicans* is similar to alpha-agglutinin, a cell surface adhesion glycoprotein of *Saccharomyces cerevisiae* (Hoyer et al., 1998 *Curr. Genet.* 33: 451-9). The gene was found to have a central domain consisting of a tandemly repeated 108-bp sequence. This 108-bp sequence in ALS1 was determined to hybridize to multiple *C. albicans* genomic DNA fragments, indicating at that time that other ALS1-like genes existed. Others have since been found.

These genes are differentially regulated by physiologically relevant mechanisms (Hoyer, 2001 *Trends Microbiol.* 9: 176-80) such as growth stage and morphological form (Hoyer et al., 1999 *Infect. & Immun.* 67: 4251-55). The ALS genes vary in size and number among the different *C. albicans* isolates and thus is highly variable (Hoyer et al., 1999). The expression of these proteins in animals indicates their role in host-pathogen interaction (Hoyer et al., 1999). Consequently they are also good proteins with which to prepare agents which can differentiate for diagnostic and epidemiological purposes the various strains.

2.2.3 Hyphal Specific Cell Wall Proteins and Proteins Involved in Morphogenesis

At least one protein that is expressed specifically in the hyphal (i.e. filamentous) growth form of *Candida albicans* is implicated in adhesion and virulence. HWP1 was first isolated as a hyphal-specific gene by differential screening (Staab et al., 1996 *J. Biol. Chem.* 271: 6298-6303). It is composed of an amino-terminal domain, which is rich in proline and glutamine and is exposed to the surface, and a C-terminal domain that includes a GPI motif and is likely to be located in the cell wall. The amino-terminal domain of HWP1 is similar to substrates of transglutaminase, a mammalian enzyme, which is thought to cross-link epithelial proteins (Staab et al. 1996). *Candida albicans* strains deleted for HWP1 have reduced transglutaminase substrate activity, reduced adhesion (measuring stable covalent linkages), and reduced virulence in a mouse model for systemic infection (Staab et al., 1999 *Science* 283: 1535-8; Tsuchimori et al., 2000 *Infect. Immun.* 68: 1997-2002).

Morphogenesis refers to the ability of *Candida albicans* to convert from either of its two growth forms to the other (e.g., from yeast-form to hyphal- or filamentous-form and vice versa). There is experimental evidence for an affect on virulence in strains that are unable to convert from one growth form to the other, or in strains that have altered expression of form-specific genes (Calderone et al., 2001 *Trends Microbiol.* 9: 327-35). In particular, mutants in the following regulatory proteins involved in morphological switching are known to exhibit reduced virulence or no virulence: the signal transduction regulatory protein CPH1, the transcriptional regulatory protein EFG1, the upstream regulatory protein RIM101, and the TEC1 regulatory protein (Calderone et al., 2001).

2.2.4 1,3-β-glucanosyltransferases

These proteins have different gene names depending on the organism from which they were derived. In *Aspergillus fumigatus*, the genes are known as GEL genes (e.g., GEL1 gene). In *S. cerevisiae*, *C. albicans*, and *Candida maltosa* they are respectively known as the GAS, PHR or EPD. The proteins derived therefrom are known as Gel1p, Gas1p, Phr1p and Epd1p if derived respectively from GEL1, GAS1, PHR1, or EPD1. The genes are required for correct morphogenesis in yeast (Mouyna et al., 2000 *J. Biol. Chem.* 20: 14882-89).

PHR1 and PHR2 encode glycosylphosphatidylinositol-anchored cell surface proteins in *C. albicans* (Fonzi, 1999 *J. Bacteriol.* 181: 7070-9). These proteins are functionally related and their expression is modulated in relation to the pH of the ambient environment in vitro and in vivo. Specifically Deletion of either gene has been demonstrated to produce a pH-conditional defect in cell morphology and virulence (Id.).

2.2.5 Secreted Aspartyl Proteinases (SAPs)

SAPs have been linked with fungal virulence since their discovery (Staib et al., 2000 *Proc. Natl. Acad. Sci. USA* 97: 6102-7). They have been identified in several members of the *Candida* genus, including *C. parapsilosis*, *C. albicans* (Beggah et al., 2000 *Microbiol.* 146: 2765-73), *C. tropicalis* (Zaugg et al., 2001 *Infection & Immunity* 69: 405-412), and *C. lusitaniae* (Pichova et al., 2001 *Eur. J. Biochem.* 268: 2669-77).

At least 10 genes (i.e., SAP1 to SAP10) have been identified in *C. albicans* (Zaugg et al., 2001). Proposed functions of the proteinases during infection include the digestion of host proteins for nutrient supply, the evasion of host defenses by degrading immunoglobulins and complement proteins, adherence and degradation of host barriers. The ability of *C. albicans* to adhere to mucosae in the oral and vaginal tracts, to invade in deep organs and to resist phagocytic cells apparently requires some of these proteinases (Zaugg et al., 2001). Sap1-3 have been shown to be crucial for superficial infection in experimental mucosal and cutaneous candidosis, whereas Sap4-6 appear to be responsible for systemic disease (Schaller et al., 2001 *J. Med. Microbiol.* 50: 743-7). SAPs have demonstrated differential expression in vitro under special experimental infection. In vivo expression technologies (IVETs) have been developed to detect expression of a gene during infection (Valdivia et al., 1997 *Trends Microbiol.* 5: 360-3).

SAP proteins are synthesized as preproenzymes. The prepeptide, or signal peptide comprising 16-18 amino acids allows the polypeptide to enter the secretory pathway by transporting it across the endoplasmic reticulum (ER). The propeptide is relatively short (i.e. 32-58 amino acid residues) and contains one to four KR sequences, one of which is located immediately before the N-terminus of the mature proenzyme (Beggah et al., 2000).

Development of antibodies against SAP antigens has already proven beneficial. The monoclonal antibody CAP1 has been shown to be potentially useful for diagnosis and treatment monitoring of invasive candidiasis (Na et al., *Clin. & Diag. Lab. Immunol.* 6: 924-9). Development of drugs against these proteinases would also be useful. Certain HIV-1 protease inhibitors (i.e., ritonavir and saquinavir) have been shown to inhibit the activity of Sap2p, Sap1p, Sap1p and Sap1p in micromolar concentrations (Pichova et al., 2001). Finally, one study in a rat model showed that immunization with a SAP protein and adjuvant could protect the host against candidal vaginitis (De Bernardis et al., 2002 *Infect. Immun.* 70: 2725-9).

3. Identified Targets

Once targets are identified using the initial in silico methods, the following information may be obtained on the protein and provided: YPD™ (Proteome database) name, synonyms, chromosome, introns, essentiality to *Candida* (e.g., effect on virulence), localization, molecular environment, functional family, role, proteome 1-line summary, an in silico summary, *Candida* hit information and coverage ($p \leq 10^{-5}$ and more preferably $p \leq 10^{-10}$), signal peptide information (3 methods), serine-threonine rich information, GPI anchor motif information, PFAM, Blimps, PSORT (motifs identified by this localization prediction software or similar software), GenBank similarity information, PDB (protein database) hits, motif information, coiled-coil information, transmembrane segments (2 methods) and cluster information (e.g., protein clustering based on motif similarities such as all ALS protein members).

This above information would be determined by the steps described supra. The flowchart of steps are described below:

After the original in silico target selection (Bioinformatics Search), the validation of a sample of these proteins were performed as described below (Biological Characterization). After gene expression was verified by RT-PCR, the genes encoding the identified proteins was deleted from *C. albicans*. The deletion strain had both alleles for that particular gene deleted or functionally deleted. The deletion strain then was compared to the wild-type strain for effects on virulence in vivo in an animal model for infection as described in Example 2. For example additional teaching, see Staab et al., 1998 *Science* 283: 1535-1538; and Han et al, *Infection & Immunity* 63: 2714-19.

For the adhesion assay, a comparison was made between the wild-type and deletion mutants of *C. albicans*. In addition, the *C. albicans* gene was introduced as a recombinant protein expressed in a heterologous species, *S. cerevisiae*. As *S. cerevisiae* is non-adherent normally, adhesion of the recombinant heterologous expression strain was compared to the parent *S. cerevisiae* strain. See, e.g., Fu et al., 1998 *Infection & Immunity* 66: 1783-6; and Cormack et al., 1999 *Science* 285: 578-2. The various deletion strains or heterologous expression strains were then tested using an improved version of the adhesion assays previously reported (Fu et al., 1998; and Cormack et al., 1999).

As described in more detail in Example 2, the six proteins: MP65, PRA1, SAP9, 6.1231, 6.1639 and 6.3873 (named CSF for cell surface factor; see Table 6) were then further characterized as targets. These proteins demonstrated an impact on virulence and/or adhesion. Additional molecular genetics or biochemical experiments to assess whether the proteins of interest are integrally involved in the cell wall and morphogenesis of *C. albicans* were also performed including complement assays. These experiments for biological characterization confirmed the 210 proteins (SEQ ID NO:211-SEQ ID NO:420) encoded by nucleotide sequences, SEQ ID NO:1-SEQ ID NO:210, as targets for therapeutics and diagnostic applications.

One skilled in the art would appreciate that additional experiments could be performed beyond the Examples described herein to confirm the same. For example, by biochemical methods, intact *Candida albicans* cells could be exposed to membrane-impermeable biochemical labeling reagents, such as biotinylation reagents (Mrsa et al., 1997 *Yeast* 13: 1145-1154; and Casanova et al., 1992 *Infection & Immunity* 60: 4898-4906). Such reagents would only modify proteins exposed on the cell surface. The corresponding proteins then could be isolated and purified by, for example, separation on an electrophoresis gel or chromatography column and identified by protein sequencing or mass spectrometric analysis.

Another alternative for biochemical determination would be to fractionate the cells using enzymes or chemical treatments to release cell wall proteins (Casanova et al., 1992). Again, the proteins could be identified by purification and sequencing or mass spectrometry.

As an alternative, by molecular genetics methods, the gene of interest could be fused to an easily-detectable reporter gene or tag and the strain could be tested to determine whether that reporter or tag is accessible from the environment or is localized in a cell wall fraction (see, e.g., Ram et al., 1998 *FEMS Microbiol. Lett.* 162: 249-255; Hamada, et al., 1998 *J. Biol. Chem.* 273: 26946-53; and Hamada et al., 1998 *Mol. Gen. Genet.* 258: 53-59). For example, an epitope tag (e.g., hemagglutinin epitope or c-myc epitope) could be introduced into the gene and detected in the expressed protein by use of an antibody raised against that epitope. If the reporter gene activity or epitope tag is detected with reagents that do not penetrate the cell wall and without damaging the cell wall or destroying the permeability of the cells, one would conclude that the protein is localized at least in part to the cell wall. Alternatively, one could test cell wall fractions for presence of the reporter or tag.

As another alternative, serum from patients infected with *Candida albicans* could be used to detect proteins of interest on a Western blot, e.g., preferably recombinant proteins produced in *E. coli* to avoid detection of carbohydrate modifications that would occur in fungi. Proteins bound by antibodies in the serum could be detected by enzyme or fluorophore-conjugated secondary antibody. Detection of target proteins of interest by patient serum (which is most likely to reaction with proteins on the fungal surface) would be suggestive but not conclusive evidence that the protein is localized to the cell wall.

The targets can be used in any of several ways. A preferred usage is to express the protein, purify a sufficient quantity, and raise monoclonal antibodies against the protein. The antibodies could then be screened for effectiveness in prophylactic or therapeutic uses against fungal infections. Preferred antibodies would be humanized or primatized™ antibodies. Less preferred, the antibodies could be used diagnostically to screen for the presence of a *C. albicans* infection. Therapeutic or prophylactic anti-fungal therapy using such antibodies could be assayed in a suitable animal infection model.

For example, mouse models exist for the study of systemic *Candida* infections (see, e.g., Han et al., 1999 *Infection & Immunity* 63: 2714-9). Another mouse model exists for use in studying vaginal *Candida* infections (Han et al., 1998 *Infection & Immunity* 66: 5771-6)

Certainly evidence has demonstrated that antibodies against the carbohydrate components of *C. albicans* and *Cryptococcus neoformans* cell surface proteins are effective in preventing fungal infections in mice (Han et al., 1995; Yuan et al., 1998 *Infection & Immunity* 66: 1057-62). Animal models such as mice and the assays described in these and other references known to the skilled artisan could be used to assess the efficacy of the antibody. If effective in a mouse infection model for example, a corresponding humanized antibody could be generated for use prophylactically or therapeutically in human patients. Alternatively, an antibody, preferably a monoclonal antibody (e.g., preferably a humanized monoclonal antibody) can be used diagnostically.

4. Antibodies

The invention includes, in one aspect, a method of treatment or prevention of systemic infection by *Candida*, and especially *Candida albicans*. The method includes administering antibodies (preferably human, humanized, or primatized antibodies) to a subject suffering from such an infection. Alternatively, antibodies can be administered to a patient at high risk (e.g., immune compromised patients) for developing a fungal infection as a prophylactic measure.

Preferably, the term "human" antibody refers to an antibody, which is substantially human in structure; that is, it derives at least its constant regions from a human antibody. This term includes so-called chimeric antibodies, in which the heavy and light chain constant regions are derived from human genes, while the heavy and light chain variable regions are derived from an immune animal source. The term also includes so-called "humanized" antibodies, in which the heavy and light chain constant regions, as well as the variable region framework regions, are human in origin, and hypervarible regions from an immune source are spliced into the structure. Finally, the term also includes antibodies selected from an combinatorial expression library.

A "primatized® antibody" is a recombinant antibody containing primate variable sequences or antigen binding portions, and human constant domain sequences. See Newman, *Biotechnology*, 1992, 10: 1455-60. Primatization of antibodies results in the generation of antibodies that contain monkey variable domains and human constant sequences. For more details see U.S. Pat. No. 6,113,898. This technique modifies antibodies such that they are not antigenically rejected upon administration in humans. This technique relies on immunization of cynomolgus monkeys with human antigens or receptors. This technique was developed to create high affinity monoclonal antibodies directed to human cell surface antigens.

In particular, according to the method described below, production of such antibodies includes the steps of (i) generating in mice monoclonal antibodies specific to a *Candida* wall protein; (ii) isolating antibody-producing cells, such as splenic lymphocytes, for production of hybridomas; (iii) cloning from the hybridomas the antibody variable region coding regions; (iv) combining the variable region coding regions with human antibody constant region coding regions in a recombinant cell; and (v) expressing the hybrid human-mouse antibodies.

Mouse anti-cell wall antibodies can be generated according to standard techniques, using as antigen a selected cell wall protein compositions described herein. Alternatively, recombinant polypeptides including polypeptides derived from a cell protein can be prepared and antibodies generated thereto. For purposes of production of monoclonal antibodies, the immunogen can, but need not be a purified protein fraction such as described in Section II above, but will preferably be at least an enriched fraction.

For example, a BALB/c female mice can be immunized on days 1, 8, 15, 32 and 46 with 10 µg denatured cell wall fraction containing substantially pure preferred cell wall protein or with 10 µg purified recombinant or synthetic protein. Animals are exsanguinated and the antibody titers of sera are determined according to standard methods by enzyme-linked immunosorbent assays (ELISA), using as solid phase coating in the microtiter wells semi-enriched target protein at a concentration of 10 µg/ml (0.1 ml/well).

Following the development of high titer antibodies, mouse spleen cells are fused with, for example, a NSI mouse myeloma line, according to standard procedures known in the art. Clones are selected for their ability to synthesize anti-*C. albicans* cell wall antibodies, as determined by ELISA with the desired cell wall protein as the antigen. Positive clones should exhibit values in the ELISA assay that are at least twice those of control samples. Western blot analysis can be used to confirm positive results. Positive hybridoma clones can then be expanded in culture according to standard procedures.

Ascites tumors can be produced by injecting $10^6$ hybridoma cells into, for example, pristane-primed BALB/c male mice, according to standard methods. Ascites fluid is recovered daily with a 25-gauge needle following the development of an ascites tumor. Typically, 15 ml of ascites fluid can be collected over a period of 7 to 10 days.

Antigenic specificity of antibodies formed in accordance with the present invention can be determined using one or more of techniques well known in the art. Such techniques are used to screen antibodies for specificity to the cell wall protein antigen. Screening techniques include but are not limited to ELISA, Western blot analysis, agglutination assays between the antigen and the antibody specific thereto.

For example, monoclonal antibodies can be tested for antigenic specificity using Western blot analysis of the immunogen or antigen preparation of interest. According to standard procedures known in the art, the cell wall preparation is separated on SDS PAGE, then transferred to nitrocellulose. The nitrocellulose strips are then incubated with test antiserum or antibody preparation, then with a species-specific anti-immunoglobulin to which is conjugated a reporter molecule, such as goat anti-mouse heavy- and light-chain IgG-alkaline phosphatase conjugate, for detecting mouse monoclonal antibodies specifically bound to antigen on the nitrocellulose. Comparison of the position on the original gel of the bound protein with known molecular weight or antigen standards is then made, to determine the specificity of the antibody preparation.

Additional support for such antibodies have been reported by other including monoclonal antibodies directed against hsp90 (Mycograb) that have entered clinical trials for the treatment of systemic candidiasis (Mathews R and Burnie J. 2001. *Curr Opi in Inves Drugs* 2: 472-476). No serious adverse events have been reported in the first stage of its double-blind Phase II trial, and the product will now progress to the next larger, stage of study. Another example of the same include, antibodies directed against *Candida albicans* aspartyl proteases (one of which is in our list of targets) are protective against vaginal candidiasis in rats (De Bernardis et al., 1997. Infect Immun 65: 3399-3405).

Additional methods of preparing and testing antibodies are well known in the art. See E. Harlow et al., *Antibodies: A Laboratory Manual* (Cold Spring Harbor Press 1989) and E. Harlow et al., *Using Antibodies: A Laboratory Manual* (Cold Spring Harbor Press 1998).

4.1 Hybrid Antibodies

In a preferred embodiment, hybrid antibodies useful in the therapeutic treatment methods of the invention are constructed to include constant regions from human antibodies and to include variable regions from antibodies of the non-human animal species, such as from the mouse described herein. According to methods now established in the art, such hybrid antibodies may be simple chimeric structures, where the entire cloned mouse heavy and light chain variable regions are attached to the constant domains of human heavy and light chains, respectively.

Alternatively, and preferably, humanized versions of such antibodies are constructed according to a method that recognizes the fact that antibody variable regions consist of relatively constant regions, the framework regions (FRs), and hypervariable regions, the so-called complementarity determining regions (CDRs). By grafting the variable regions of the mouse antibodies into human framework regions (FRs) of the antibodies, the potential for unwanted immune reactions is reduced.

In accordance with the present invention, antibodies useful in the therapeutic or diagnostic methods of the invention will bind *Candida* cell wall proteins, and preferably block binding of *Candida* cell wall proteins to human cells, or block virulence of the *Candida* spp. Antibodies that bind *Candida* cell wall proteins, but have no effect on virulence or adhesion, may also prove useful in prophylactic treatment by facilitating clearance of fungal organisms from the bloodstream and tissues of an infected animal.

One method of preparing humanized antibodies can be as follows. Total RNA is prepared from a hybridoma cell line according to a standard guanidinium cesium chloride method. cDNA is prepared from the total RNA, and an oligo dG tail is added to the 3' terminus of the cDNA with terminal deoxynucleotidyl transferase. According to methods well known in the art, H and L chain variable (V) region segments are amplified from the cDNA by polymerase chain reaction (PCR) using primers that (i) anneal to the dG tail and to the gamma or kappa constant regions located 5' to the heavy and light chain variable regions, respectively, and (ii) introduce appropriate restriction sites. The 5' primers are constructed according to known sequences of mouse gamma and kappa constant regions. PCR products are purified according to standard methods, such as by gel purification, digested with restriction endonuclease and ligated into a vector such as pUC18 (Clontech, Palo Alto, Calif.) for DNA sequence analysis.

A cell line is selected for transfection with the cloned heavy and light chain genes, according to criteria known in the art. One particularly useful cell line is the Sp2/0 cell line (ATCC, Rockville, Md.). About $10^7$ Sp2/0 cells can be transfected, by electroporation or by another suitable transfection method. When electroporation is used, about 20 μg each of linearized L and H chain plasmid DNA should be electroporated into the cells using a commercial apparatus, such as a "GENE PULSER" apparatus (BioRad, Richmond, Calif.) at 360 V and 25 microfarad capacitance, following the manufacturer's instructions. Cells from an entire transfection are plated in a 96-well tissue culture plate in non-selective medium (DMEM; GIBCO BRL, Grand Island, N.Y.) supplemented with 10% Fetal Calf Serum. After a suitable time, generally about 48 hours, spent medium is replaced with selective medium (DMEM with 10% FCS, HT media supplement; Sigma, St. Louis, Mo. supplemented with xanthine, and mycophenolic acid). Culture medium can be assayed for the presence of human IgG according to standard methods by ELISA.

5. Vaccines

One embodiment of the invention is vaccines which can be used to treat or prophylactically prevent or inhibit *Candida* infections. These vaccines can be in the form of subunit vaccines, vaccines based semi-purified proteins from *Candida* cell cultures, vaccines using recombinant or synthetically produced *Candida* proteins either alone or in combination, conjugate vaccines, and attenuated vaccines. In the instance of recombinant or synthetically produced *Candida* proteins used as antigen in vaccines, these polypeptides also can be glycosylated.

The antigenic proteins derived from *Candida albicans* (either via purification, recombinant or synthetic means) possess vaccine activity against infectious diseases caused by *Candida albicans* (or other related *Candida* species) or possess allergen activity useful in the prevention and therapy of allergic symptoms caused by *Candida albicans*.

The term "vaccine activity," as used herein means that the vaccine prepared exhibits a pharmacological action effective as a vaccine. The term "allergen activity" means that an abnormally high value is obtained in an IgE antibody titer measurement test against the fungal antigen of the present invention by RAST assay and the like using serum from a patient with allergosis, or a positive reaction is shown in a skin test using the fungal antigen of the present invention. Furthermore, functional equivalents possessing properties immunologically equivalent to those of isolated antigenic proteins as described above are also encompassed in the scope of the fungal antigen of the present invention. For example, functional equivalents of various strains of *Candida albicans*, and fungi of *Candida* other than *Candida albicans*, are also encompassed in the present invention.

The phrase "functional equivalent possessing immunologically equivalent properties," as used herein, is defined as a protein with substitution, insertion, deletion, or addition of one or more amino acids of which the immunological properties, such as vaccine activity and/or allergen activity, are equivalent to the above.

Also, an antigenic fragment can also be prepared based on an isolated antigenic protein. An antigenic fragment can, for example, be prepared by cleaving an isolated antigenic protein as the starting material by enzymatic digestion with a protease, such as lysyl endopeptidase or trypsin, or by chemical treatment with cyanogen bromide etc., and then isolating and purifying a fragment possessing the desired antigenicity by a known method for protein purification. It is also possible to produce an antigenic fragment by chemical synthesis using peptide synthesis technology, on the basis of the information on the chemical structure of the antigenic fragments. The antigenic fragment of the present invention includes fragments of a fungi-derived antigenic protein that cause immune responses in mammals, especially in humans, including for instance, minimal level of IgE stimulation, IgE binding, and induction of IgG and IgM antibody production, or T cell responses, such as proliferation, and/or lymphokine secretion and/or T cell anergy induction. Some of the polypeptide and peptide fragments will preferably also be glycosylated.

The antigenicity of an antigenic fragment can also be evaluated in vitro using, e.g., RAST, ELISA, and histamine release tests, in addition to skin tests and intradermal tests in human volunteers.

Incidentally, for the purpose of increasing fungal antigen stability and/or increasing desired reactivity, i.e., enhancing the induction of individual protective immunity, attenuating allergic reactions, or inactivating enzymes, for therapeutic purposes, and enhancing specific antigen-antibody binding for diagnostic purposes, it is possible to modify an antigenic protein or antigenic fragment to a derivative thereof, or to bind it with polyethylene glycol (PEG) using the PEG method (Wie et al., 1981 *Int. Arch. Allergy Appl. Immunol.* 64: 84-99). Protein modifications include pyridylethylation, reduction, alkylation, acylation, chemical coupling to appropriate carriers, mild formalin treatment, and guanidine hydrochloride treatment.

5.1 Subunit Vaccines

Preferable vaccines are those that are based on one or more isolated and/or purified *Candida* polypeptides. These polypeptides can be isolated either from the *Candida* organism or produced recombinantly. In the instance where haptens are being used, the haptens can be produced either from *Candida* isolated proteins, recombinantly produced *Candida* proteins, or synthetically manufactured *Candida* proteins and polypeptides.

5.1.1 Production from *Candida* Cells

Proteins produced and purified from *Candida* cells can be performed, for examples, as follows. Briefly, *C. albicans* cells are cultured and harvested according to standard methods.

For example, the method can comprise obtaining living fungal cells. More specifically, the method comprises culturing a fungus in a culture medium suitable for its growth, and obtaining fresh living fungal cells. First, fungal cultivation can be carried out under temperature and other conditions in which fungi can grow in a nutrient medium containing carbon sources, nitrogen sources, and other nutrient sources suitable for each fungus. As the nutrient media usually usable for fungal cultivation, Sabouraud medium, Potato-Dextrose medium, Czapek-Dox medium, malt medium, yeast nitrogen base glucose chemically defined medium, and the like can be widely used, and serum and/or serum albumin may be added as necessary. Although the culturing temperature is usually from about 15° C. to about 45° C., some fungi show morphological changes depending on the culturing temperature (many of which are known as dimorphic fungi), and an appropriate selection of a culturing temperature is necessitated. For instance, in the case of *Candida albicans*, for which preferably employable culturing temperature is in the range from 25 C to 37 C, yeast-phase growth takes place at about 30 C when cultured in usual media, whereas mycelial-phase growth is likely to take place around 37 C. For dimorphic fungi, culturing conditions may be altered according to the purpose, since changes also occur in cell wall components, and protein components, such as intracellular proteins, including membrane proteins.

Cell wall proteins can be treated enzymatically or with certain chemicals to release the cell wall proteins or polypeptides from the fungal cells. Chemical agents include, but are not limited to, β-mercaptoethanol, dithiothreitol, sodium dodecyl sulfate (SDS), or sodium hydroxide. Alternatively, cells can be exposed to enzymatic digestion that would release polypeptides.

There are various cell wall lytic enzymes known to date, commercial products including ZYMOLYASE (manufactured by Seikagaku Corporation), Lyticase (manufactured by Sigma), yatalase (manufactured by Ozeki Corporation-Takara Shuzo Co., Ltd.), chitinase (manufactured by Takara Shuzo Co., Ltd.), *Trichoderma* Lysing Enzyme (manufactured by Novo-Sigma), snail intestinal digestion enzyme β-glucuronidase (manufactured by Sigma), and Laminariase (manufactured by Sigma). These enzymes comprise lytic enzymes for various cell wall polysaccharides (chitin, β-1, 3-glucan, mannan, galactomannan, xyloglucan, etc.), many of which further contain proteases.

In addition, when the released proteins or polypeptides are dialyzed against a solubilizer-free buffer, a portion of hydrophobic components, including lipids, is obtained as precipitates. These precipitate components and solution components are all encompassed in the scope of the solubilized fraction in the present specification.

In the present invention, the released proteins or polypeptides of interest may be further purified by conventional means of separation and purification according to its purpose, including, for instance, means of separation and purification based on differences in component affinity, charged states, molecular weights, hydrophobicity, and the like as desired. For example, the proteins/polypeptides can be purified by fractionation based on differences in the sugar residues contained in the glycoprotein with a sugar group-specific affinity medium. The sugar group-specific affinity media include, for example, immobilized lectin media. In particular, preference is given to ConA-bound resins for the separation of a component having a ConA-binding sugar residue (e.g., α-D-glucose residue and α-D-mannose residue of which C-3, C-4, and C-6 hydroxyl groups are unsubstituted), e.g., a glycoprotein, which can be found in many fungi, rich in ConA-binding mannose residues. For purification, it is desirable to use a buffer according to its purpose, and a surfactant, an organic solvent, and the like may be also added. The degree of purification may be increased using an ion exchange resin or gel filtration carrier.

Also, in the present invention, the fungal antigen of the present invention can easily be produced by general genetic engineering techniques using a nucleic acid encoding the fungal antigen of the present invention described above.

5.1.2. Recombinant Proteins

When the open reading frames (ORFs) encoding the desired protein are identified and verified, these can be inserted into preferred vectors. These vectors can then be transformed into desired hosts (e.g., *Pichia pastoris, S. cerevisiae* and the like) to express the protein. In the event that the protein is glycosylated, it is preferred to express the protein heterologously in another fungus or perhaps in an insect cell lines (e.g., Sf9) or mammalian cell line such that the glycosylation is maintained. Alternatively, if the protein is not believed to be glycosylated, then the protein can be expressed perhaps in bacteria, such as *E. coli.*

Alternatively, based on the information of a partial amino acid sequence for the above isolated antigenic protein, nucleic acids encoding the antigen can be isolated by PCR and the like. An example thereof is described as follows:

First, cDNA library is prepared from cells expressing a desired antigenic protein. Next, PCR is carried out with genomic DNA for the cell expressing the antigenic protein as a template, by using an oligonucleotide usable for an amplification primer which is designed based on the nucleotide sequence of the nucleic acid which is deduced to encode a partial amino acid sequence of an antigenic protein; and another suitable oligonucleotide capable of forming an amplification primer pair with the above oligonucleotide for the above nucleic acid. A DNA encoding the desired antigenic protein can be selected from the cDNA library by hybridization using, for example, as a probe a DNA fragment obtained by the above PCR. Additional methods of preparing recombinant proteins would be known to the skilled artisan.

As a side note, *C. albicans* is known for a unique usage of the CTG codon. Typically, CTG is translated as a leucine, but *C. albicans* translates CTG as a serine, which will have an impact on the serine-threonine content of a polypeptide. This unique codon is also used in other species of *Candida* as would be known to the skilled artisan. Thus, when preparing recombinant forms of *C. albicans* proteins in organisms other than *C. albicans*, the nucleic acid encoding these proteins will preferably be altered by site-directed mutagenesis to change the codon to another codon universally recognized as encoding a serine residue (e.g., a CTG to UCG mutation).

In a preferred embodiment, the proteins can be expressed in a truncated form, wherein the extracellular domains of the protein are the portions expressed and then can be used to prepare antibodies or in vaccines. These truncated recombinant proteins preferably further contains the same post-translational modifications (e.g., glyosylation groups) that are present in the native protein. The proteins can be expressed as truncated proteins or in the form of fusion proteins as would be known in the art. In a similar fashion, the N-terminal antigenic domain of Hwp1 was isolated for the purpose of adhesion experiments (Staab et al., 1999 *Science* 283: 1535-8).

5.2 Conjugate Vaccines

In another embodiment, conjugate vaccines can be prepared. These conjugate vaccines comprise antigens which are joined (i.e., conjugated) to another compound to enhance the antigenicity, generally, of the antigen. In one method, instead of removing the unconjugated or free protein that remains after producing the protein-polysaccharide conjugates, only certain reagents and low molecular weight polysaccharides are removed from the reaction mixture. The free unconjugated protein remains in solution with the protein-polysaccharide conjugate. By this improved process, the resulting conjugate vaccine can have improved immune response due to the free protein while reducing production costs, equipment costs, and time expenditure in conjugate production.

In addition to the protein and polysaccharide components, during conjugate production, various reagents and low molecular weight components typically are present in the reaction mixture (e.g., cross-linking reagents, buffering components, low molecular weight oligosaccharides, etc.). These excess reagents and low molecular weight components can be removed from the reaction mixture by any suitable process known in the art, such as through dialysis, ultrafiltration, or desalting columns. Typically, at least any materials having a molecular weight below 10,000 are removed, and preferably, materials having a molecular weight below 30,000 are removed. This removal provides a purified mixture including the protein-polysaccharide conjugate and the free protein. Preferably, little or no free protein is removed from the mixture during this initial purification step. The purified mixture preferably contains protein-polysaccharide conjugate and free protein in a weight ratio of 0.95 mg conjugated protein per 0.05 mg free protein to 0.1 mg conjugated protein per 0.9 mg free protein, and advantageously this ratio is in the range of 0.7 mg conjugated protein per 0.3 mg free protein to 0.95 mg conjugated protein per 0.05 mg free protein. These ratios correspond to 5-90% free protein, and preferably 5-30% free protein, by weight, based on the entire protein content.

While these free protein ratios are preferred, with high conjugate yield during the conjugation reaction, the free protein content can be as low as 1% in the invention, such that the purified mixture contains 1-90% free protein, with 1-30% free protein preferred (based on the entire protein content). In one embodiment of the invention, the ratio of conjugated to free protein is about 1:1 by weight.

The purified mixture, including the free protein and the protein-polysaccharide conjugate, can be combined with a pharmaceutically acceptable medium or delivery vehicle. As will be discussed in more detail below, the pharmaceutically acceptable medium or delivery vehicle can include at least one member selected from the group consisting of water, petroleum oil, animal based oil, vegetable oil, peanut oil, soybean oil, mineral oil, sesame oil, saline, aqueous dextrose, and glycerol solutions.

In accordance with the process of the invention, the polysaccharide can be activated, for example, using an organic cyanylating reagent during the step of producing the conjugate. Suitable cyanylating reagents include 1-cyano-4-(dimethylamino)-pyridinium tetrafluoroborate ("CDAP"), N-cyanotriethyl-ammonium tetrafluoroborate ("CTEA"), and p-nitrophenylcyanate. As noted above, the use of such organic cyanylating reagents is described in U.S. Pat. No. 5,651,971. CDAP is particularly preferred as an organic cyanylating reagent.

The protein and polysaccharide also can be conjugated together via a spacer in the process according to the invention. As one example, a thio-ether spacer can be used in this process. Homobifunctional or heterobifunctional vinylsulfones can be used as spacers in the protein-polysaccharide conjugate. The protein and/or the polysaccharide can be derivatized or functionalized prior to the conjugation reaction procedure (e.g., with thiols, amines, or hydrazides).

In another aspect of the invention, a hapten-protein-polysaccharide conjugate can be prepared using a mixture including a protein-polysaccharide conjugate and free protein produced in the manner described above. After the purified mixture containing the conjugate and the free protein is prepared, a hapten is reacted with the purified mixture to thereby provide a conjugate mixture including a hapten-protein conjugate and a hapten-protein-polysaccharide conjugate. This conjugate mixture can be treated further to remove the free hapten to thereby provide a purified conjugate mixture. This purified conjugate mixture can be mixed with a pharmaceutically acceptable medium or delivery vehicle. Preferable haptens are those exposed at the cell surface of the organism, versus, for example being embedded in the transmembrane portion of the protein.

The excess hapten can be removed from the conjugate mixture by any suitable process known in the art. As one specific example, the excess peptide is removed by dialysis to provide the purified conjugate mixture. Peptides are the particularly preferred haptens for use in this embodiment of the invention.

An alternative procedure for producing a conjugate mixture including a hapten-protein-polysaccharide conjugate and a hapten-protein conjugate is described below. A hapten-protein conjugate first is produced by reacting a hapten (e.g., a peptide) with a protein. The excess free protein and/or free hapten optionally (and preferably) is removed at this stage. Thereafter, this conjugate is reacted with a polysaccharide to form a hapten-protein-polysaccharide conjugate. In this reaction, the hapten-protein conjugate is used in excess to produce a conjugate mixture including the excess hapten-protein conjugate and a hapten-protein-polysaccharide conjugate. The purified conjugate mixture includes the hapten-protein conjugate and the hapten-protein-polysaccharide conjugate. This conjugate mixture can be combined with a pharmaceutically acceptable medium or delivery vehicle.

While any amount of protein can be included in the conjugates according to the invention, generally about 0.1 to 1.0 mg protein is present per mg polysaccharide in the conjugate mixture. Also, in conjugates that include peptides, generally there will be about 5-30 moles peptides per mole of protein.

The processes in accordance with the invention can be used on any suitable protein. Where a peptide or other hapten is included in the conjugate, any suitable peptide or other hapten can be used. This invention is particularly suitable for conjugation methods where the unconjugated protein is unmodified or minimally modified by the conjugation reaction procedure. CDAP coupling to produce the protein-polysaccharide conjugate is one such conjugation technique where the method according to the invention may be used. The method according to the invention, however, also may be used with other conjugation techniques where there are minimal modifications in the uncoupled protein. The unconjugated protein fraction in the protein-polysaccharide conjugate vaccine can be just as immunogenic as the native protein.

The process of the invention also can be used in producing a combination vaccine. As another alternative, the process of the invention also can be used in the preparation of peptide-protein-polysaccharide conjugates or other hapten-protein-polysaccharide conjugates. Typically, when making such conjugates, a protein-polysaccharide conjugate first is prepared, and thereafter, a peptide is coupled to this conjugate. Alternatively, the protein-polysaccharide conjugate can be produced, and the free protein allowed to remain with the protein-polysaccharide conjugate. Thereafter, the peptide is reacted with this conjugate mixture, including the protein-polysaccharide conjugate and the free protein, to thereby produce a conjugate mixture including a peptide-protein-polysaccharide conjugate and a peptide-protein conjugate. The free peptide can be removed by dialysis to provide a purified conjugate mixture including the peptide-protein conjugate and the peptide-protein-polysaccharide conjugate. By eliminating the free protein removing step, the peptide-protein-polysaccharide conjugate can be produced in a more cost effective manner, and the resulting purified conjugate mixture produces enhanced anti-protein and anti-peptide responses.

5.3 Attenuated Vaccines

Another embodiment contemplates preparing recombinant forms of *Candida* and preferably *C. albicans*, which are attenuated. These attenuated forms can then be prepared in the form of live, attenuated vaccines.

5.4 Pharmaceutically Acceptable Vaccine Carriers

Suitable carriers for administration of vaccines are well known in the art and can include buffers, gels, microparticles, implantable solids, solvents, other adjuvants or any other means by which the antigen of the vaccine can be introduced into a patient and be made sufficiently available to produce an immune response to the antigen. In the preferred embodiments of the present invention the carrier is a lactose-containing solution of Lactated Ringers Solution (or other isotonic solution), aluminum hydroxide gel and formaldehyde. Formaldehyde is added to the preferred embodiments to serve as an agent that will kill fungi and prevent contamination of non-specific organisms. Other such agents can also be employed in formulating antigen preparations and vaccines of the present invention.

A method of producing such a *Candida* vaccine is also disclosed. The method comprises making a *Candida* antigen preparation comprising a *Candida* antigen described above and combining the antigen preparation with a suitable carrier. The antigen preparation can be prepared by any available means for obtaining antigen in a form that can be added to the carrier. The preferred embodiments also aspirate or filter the homogenized culture before it is added to the carrier. Finally, the antigen preparation is added to the carrier such that antigen is present in a concentration sufficient to produce an immune response and/or confer resistance upon administration of the vaccine to a patient.

When the fungal antigen of the present invention is used as a vaccine composition, in order to get more potent humoral and/or cellular immunity, it is preferable to administer the fungal antigen in the form of preparation of a suspension or solution containing an adjuvant as described below. Although the adjuvant is usually administered together with the antigen, the adjuvant may be administered before or after antigen administration. The adjuvants suitable for vaccination for mammals include complete or incomplete Freund's adjuvant; gels made of inorganic substances such as aluminum hydroxide and alum; surfactants, such as lysolecithin, dimethyloctadecyl ammonium bromide and lysolecithin; polyanions, such as dextran sulfate and poly-IC; peptides, such as muramyl dipeptide and tuftsin; Monophosphoryl Lipid A (MPL) manufactured by Ribi; TiterMax, manufactured by CytRx; cholera toxin (CT); B subunit of CT; heat-labile toxin (LT), without being limited thereto. The antigen can also be administered by incorporating it in a liposome or other microcarriers. As a matter of course, antigens of some different fungi can also be used in admixture, whereby protective immunity against a plurality of mycotic infectious diseases is induced. Preferably, immunity is against a plurality of *Candida* species.

The vaccine composition of the present invention may be used in combination with antifungal agents, such as fluconazole and amphotericin B, and β-lactam antibiotics and other various antibacterial antimicrobial agents. Additional reagents and their methods of administration are discussed infra.

Vertebrates are fish, amphibians, reptiles, birds, humans, and mammals except humans, which produce antibodies in reaction with antigens, so that all vertebrates are capable of reacting with vaccines. Although vaccines are generally applied to mammals, such as humans or domestic animals, vertebrates, e.g., fish cultured for commercial purposes, are encompassed in the scope of the present invention, as long as they possess the above-described properties.

As the route of administration, the fungal antigen of the present invention may be administered orally, transmucosally (e.g., nasally, intravaginally), percutaneously (e.g., subcutaneously or intracutaneously), or intravenously. Representative initial doses are 0.001 to 5 mg/kg body weight as an amount of protein, and depending upon to the degree of prevention or therapy required the dose can be increased, or the number of administration can be increased.

The fungal antigen of the present invention is administered, potent cellular immunity and/or humoral immunity can be induced, whereby fungal infection can be prevented or treated. The protective effects and therapeutic effects can be induced not only against the fungus of interest for protection or therapy but also against other fungi though with some insufficiency. This is presumably due to the fact that certain antigens in the *Candida* family, and even among other species of fungi, are conserved In addition, the present invention provides 1) a pharmaceutical composition for inducing protective immunity against fungi or exhibiting therapeutic effects by administering to individuals, characterized in that the pharmaceutical composition contains the fungal antigen described above, or a fungal antigen produced by the process described above; 2) a vaccine composition for inducing protective immunity against fungi, preferably *Candida*, or exhibiting therapeutic effects by administering to individuals, characterized in that the vaccine composition contains the fungal antigen described above, or a fungal antigen produced by the process described above; 3) a method of stimulating an immune responses against fungi, preferably *Candida*, in a vertebrate, comprising the step of administering the above vaccine composition; and 4) a method of stimulating an immune responses against fungi, preferably *Candida*, in a vertebrate, wherein proliferation of fungi used in the preparation of the vaccine composition and/or fungal strains closely related thereto is suppressed by the immune responses in a vertebrate to which the vaccine composition is administered, to prevent or treat diseases caused by the fungi.

The fungal cell wall antigens of the present invention can be used in the form of a biologic product, such as an allergen composition usable for desensitization therapy for allergoses and other purposes, as well as the above-described vaccine composition. Further, the fungal antigen of the present invention can also be used for in vivo diagnosis and/or laboratory diagnosis for determination of past history of infection by skin reactions, allergosis diagnosis by scratch tests, and for other purposes. Preparations used for laboratory diagnosis include, for example, immunological diagnostic agents, such as microtiter reagents, latex agglutination reagents, immunonephelometric reagents, and enzyme immunoassay reagents.

When the allergen composition of the present invention is administered to a patient for the purpose of preventing or treating allergosis, the allergen composition can be used in the form of an appropriate salt solution or suspension, and may be supplemented with polyethylene glycol or phenol. Further, it can also be administered as the suspension or solution containing an adjuvant usable for making vaccine preparations for mammals as described above. The adjuvant can be usually administered together with an antigen, and it may be given before or after antigen administration. The antigen can also be administered by incorporating it in a liposome or other microcarriers.

As the route of administration, it may be administered percutaneously (subcutaneously or intracutaneously), nebulized via intrapulmonary, administered transmucosally (e.g., via nose, eye, vagina, or the like), orally, subglossally, or intravenously. A representative initial dose for treating depends upon the route of administration, and is, for example, 0.2 ng to 0.1 mg/kg per administration, and depending upon the degree of prevention and therapy required the dose can be increased, or the number of administration can be increased.

When the fungal antigen of the present invention is used in an individual for the purpose of in vivo diagnosis, e.g., in inhalation challenging test, skin test, or nasal or eye mucosal test, it can be used in the form of a lyophilized powder or an appropriate salt solution or suspension, and polyethylene glycol and/or phenol may be added thereto. For patch tests, it is possible to use a solution of the above-mentioned antigenic component in a mixture of white petrolatum as a base material supplemented with a surfactant, such as sodium lauryl sulfate.

The fungal antigen of the present invention can also be used for laboratory diagnoses, e.g., diagnostic methods based on antigen-antibody reactions, such as agglutination, precipitation reaction, and neutralization reaction; diagnostic methods using labeled antibody; histamine release test; lymphocyte transformation test; and leukocyte migration inhibition test. For example, when used as an antigen for IgE antibody titer, the above-described antigen component can be used by immobilizing it on a solid phase, such as a paper disc, cellulose sponge, or microplate.

The present invention also provides 1) a diagnostic composition for a disease caused by fungi, characterized in that the diagnostic composition contains the fungal antigen described above, or a fungal antigen produced by the process described above; and 2) a method for diagnosing a disease caused by fungi in a vertebrate, comprising using the diagnostic composition above

6. Chemical Compounds Targeting Cell Wall Proteins

6.1 Virulence Targets

*C. albicans* expresses several virulence factors that contribute to pathogenesis. These factors include, but are not limited to host recognition biomolecules (e.g., adhesins), morphogenesis (i.e. the reversible transition between unicellular yeast cells and filamentous, growth forms), secreted aspartyl proteases, proteins involved in phenotypic switching, and secreted enzymes (e.g., including secreted aspartyl proteases and phospholipases). For target proteins that are shown to be involved in virulence by a particular one of these mechanisms, high-throughput screens could be designed for the compounds that prevent that activity (e.g., prevent a particular enzymatic activity). For example, the *Candida albicans* protein geranylgeranyltransferase type I was expressed in *E. coli*, purified and used to screen for compounds which inhibit its activity (Smalera et al., 2000, *Biochim. Biophys. Acta* 1480: 132-44). Alternatively, compounds can be screen similar to how inhibitors of the sirtuin family of NAD-dependent deactylases in *S. cerevisease* were identified (Grozinger et al., 2001 *J. Biol. Chem.* 276: 38837-43).

6.2 Adhesion Targets

The ability to adhere to host tissue is considered a prerequisite for the early stages of colonization and tissue invasion. Adherence is achieved by a combination of specific (ligand-receptor interactions) and non-specific mechanisms which allow the fungi to attach to a wide range of tissue types and inanimate surfaces (Cotter et al., 2000 *Br. J. Biomed. Sci.* 57: 241-9).

For adhesion targets identified by the methods described herein, assays can be performed which screen compounds in wild-type *C. albicans* or in a heterologous *S. cerevisiae* which expresses a *C. albicans* protein wherein the compound or composition prevents cell adhesion or which can dislodge previously adhered cells. For example, compounds could be assayed for adhesion of the fungal cells to plastic (Reynolds et al., 2001 *Science* 291: 878-81), plastic coated with appropriate proteins (e.g., collagen or fibronectin) (Gaur et al., 1997 *Infection & Immunity* 65: 5289-94), bioprosthetic materials (Chandra et al., 2001 *J. Bacteriol.* 183: 5385-94), synthetic matrixes (Watts et al., 1998 *FEMS Microbiol. Lett.* 159: 129-135), mammalian cells in culture, tissue sections, or appropriate tissue models (Bernhardt et al., 2001 *J. Infect. Dis.* 184: 1170-5).

Cell wall targets identified by methods described herein could also be screened to identify compounds which prevent maturation to a biofilm-like state or that disrupt an existing biofilm. Several in vitro models exist for fungal biofilms grown on different types of supports (e.g., Chandra et al., 2001 *J. Bacteriol.* 183: 5385-94; Hawser et al., 1995 *Antimicrob. Agents Chemother.* 39: 2128-31). These fungal biofilm assays could be modified for 96-well plates such that rapid screening of compounds could be performed. Screening for compounds and compositions that affect adhesion or biofilms could be accomplished directly in *C. albicans* strains.

Secondary screening could then be performed to ascertain which cell surface proteins were the target of the compound. Such secondary screening could be done, for example, by comparing deletion and wild-type *C. albicans* strains or by comparing strains that alter the expression level of the protein of interest under specific conditions (e.g., conditional mutants). See, e.g., Giaever et al., 1999 *Nat. Genet.* 21: 278-83; and Launhardt et al., 1998 *Yeast* 14: 935-942.

7. Pharmaceutical Formulations

The pharmaceutical formulation used will depend on whether the *Candida* infection is systemic or superficial. In the event the infection is systemic, then drugs would be administered either systemically (e.g., intravenously) or topically. If the infection is superficial, it may only be treated topically, although today it may also be treated systemically depending on the needs of the patient.

The agents identified which affect cell wall proteins could be formulated alone or in combination with other antifungal agents. If the anti-cell wall agent was to be administered systemically, then the drug could be administered alone or in combination with other systemic antifungal agents. Systemic antifungal agents include amphotericin B (FUNGIZONE, ABCD, AMPHOTEC, AMPHOCIL, AMBIZOME, ABELCET, ABLC), flucytosine, imidazoles, triazoles, ketoconazole, itraconazole, fluconazole, and terbinafine. Others include: Lipid based formulation of antifungal drugs (including Amphotericin B—nystatin) Arikan S., 2002 *Cell Mol Biol Lett* 7(3):919-22) and antifungal agents based on echinocandin B which target cell wall biosynthesis and inhibit β-D-glucan synthase (Barrett D., 2002 *Biochim Biophys Acta* 18; 1587(2-3):224-33).

In the event the anti-cell wall agent is to be administered topically, then the agent may applied alone or in combination with another antifungal agent. Other topical antifungal agents include, but are not limited to imidazoles, triazoles, butoconazole, ciclopirox olamine, haloprogin, tolnaftate, naftifine, terbinafine, butenafine, polyene antifungal antibiotics (e.g., nystatin and amphotericin B), and miscellaneous antifungal agents (e.g., undecylenic acid, benzoic acid, salicylic acid, propionic acid, caprylic acid, and potassium iodide).

Although the present invention has been described in detail with reference to examples above, it is understood that various modifications can be made without departing from the spirit of the invention, and would be readily known to the skilled artisan. The following Examples are provided to specifically illustrate the invention.

EXAMPLES

Example 1

Method of Identifying Proteins

Targets are identified by compiling from genome wide scans from known databases based on known properties of cell-surface proteins, as discussed herein and from known data. These genome wide scans would include scans of open reading frames (ORFs) from PathoGenome™ and Stanford genome databases. Other databases, such as EST and cDNA databases can also be searched as discussed herein. The search is based on the presence of one or more of the following criteria: (1) Ser-Thr rich regions, (2) signal peptides, (3) GPI motifs, (4) large size, (5) predicted cell wall protein, i.e., not soluble, (6) number of Cys residues.

The "known data" includes literature and annotated sequences regarding various cell surface proteins both in *Candida* and in related species, such as *S. cerevisiae*. Such known data will include proteins described as related to cell adhesion, virulence, with a GPI anchor, or involved in cell wall maintenance, to name a few. The targets identified in this manner would include cell surface proteins, adhesion proteins, biofilm proteins, proteins involved in making the cell wall, proteins distributed throughout the entire cell and incorrectly annotated proteins. This search method could also potentially miss uncharacterized proteins from *S. cerevisiae* and *C. albicans*, some *Candida* proteins with no homologs in other related species. Today the *Candida* genome still has not been completed and many of the proteins described to date are not complete (e.g., potentially missing the N-terminus, signal peptides, C-terminus, GPI signals, and the like).

The proteins identified using the above method include the following, which had been previously identified in the Proteome Bioknowledge database (Incyte Genomics, Palo Alto, Calif.).

TABLE 2

| Gene Name* | Protein Name | Description |
|---|---|---|
| ALS1 | Adhesin | Agglutinin-like cell surface glycoprotein; may be involved in adhesion and pathogenesis |
| ALS3 | Adhesin | Agglutinin-like cell surface glycoprotein, hyphal-specific |
| ALS8 | Adhesin | Agglutinin-like cell surface protein, hyphal-specific |
| ALS5 | Adhesin | Agglutinin-like adhesin, involved in adhesion to extracellular matrix proteins |
| CHT2 | Hydrolase | Chitinase 2, involved in cell wall biosynthesis |
| HYR1 | Unknown | Hypahl-specific cell wall protein |
| PHR1 | Transferase | 1,3-β-gluanosyltransferase, involved in cell wall maintenance, morphogenesis and virulence, expression is induced at alkaline pH |
| PHR2 | Transferase | 1,3-β-gluanosyltransferase, involved in morphogenesis and virulence, expression is induced at acid pH |
| ALS4 | Adhesin | Agglutinin-like cell surface protein |
| ALS6 | Adhesin | Agglutinin-like cell surface protein |
| RBT1 | Unknown | Putative cell wall protein with a role in virulence, transcriptionally repressed by Tup1p |

*ALS = agglutinin-like sequence; CHT = chitinase; HYR = hyphally regulated; PHR = pH responsive; RPT = repressed by Tup1p The above method also identified a series of unnamed sequences, which are provided below:

TABLE 3

| ORF No. | Protein Name | Description |
|---|---|---|
| orf6.162 | Unknown | Protein of unknown function having a region of low similarity to *C. albicans* Hwp1p, which is a hyphal-specific cell wall protein with a role in attachment to host epithelial cells. |
| orf6.1331 | | |
| orf6.1377 | Adhesin | Protein with high similarity to *C. albicans* Als1p, which is an agglutinin-like cell surface glycoprotein that may be involved in adhesion and pathogenesis. |
| orf6.2071 | Unknown | Protein with high similarity to *S. cerevisiae* Sim1p, which is involved in the agining process and in regulation of the cell cycle |

TABLE 3-continued

| ORF No. | Protein Name | Description |
|---|---|---|
| orf6.2344 | Hydrolase | Protein apparently identical to *C. albicans* Cht2p[1], which is involved in cell wall biosynthesis, member of the alternate chitin synthase family which includes enzymes other than chitinase |
| orf6.3143 | Unknown | Protein of unknown function having low similarity to a region of aggrecan (murine Agc), which is a large aggregating chondroitin sulfate proteoclybcan that has a critical role in the formation of cartilage |
| orf6.3288 | | |
| orf6.3591 | Unknown | Protein of unknown function having a region of low similarity to a region of *C. albicans* Hwp1p, which is a hyphal-specific cell wall protein with a role in attachment to host epithelial cells. |
| orf6.3873 | Transferase | Protein of unknown function having moderate similarity to *C. albicans* Phr1p, which is a 1,3-β-glucanosyltransferase involved in cell wall maintenance, morphogenesis and virulence and induced in alkaline pH |
| orf6.4149 | | |
| orf6.4915 | Adhesin | Protein with strong similarity to *C. albicans* Als5p, which is agglutinin-like adhesin involved in adhesion to extracellular matrix proteins |
| orf6.5354 | Unknown | Protein of unknown function having low similarity to *C. albicans* Hwp1p, which is a hyphal-specific cell wall protein with a role in attachment to host epithelial cells. |
| orf6.6260 | | |
| orf6.7524 | | |
| orf6.7977 | Unknown | Protein with high similarity to *S. cerevisiae* Uth1p, which is a protein involved in the aging process |
| orf6.8574 | Adhesin | Protein with high similarity to *C. albicans* Als5p, which is an agglutinin-like adhesin involved in adhesion to extracellular matrix proteins. |

By "unknown" is meant that the protein has not been previously characterized by others in the public domain.

As used herein, an open reading frame containing the nucleotide sequence is designated with the prefix "orf." Is in some instances, the designator is italized, indicating nucleotide sequence such as "6.162". The corresponding proteins contain a 'p' is used as the suffix; for example 6.162p. These designations are interchangeable throughout the specification.

Figure 8:
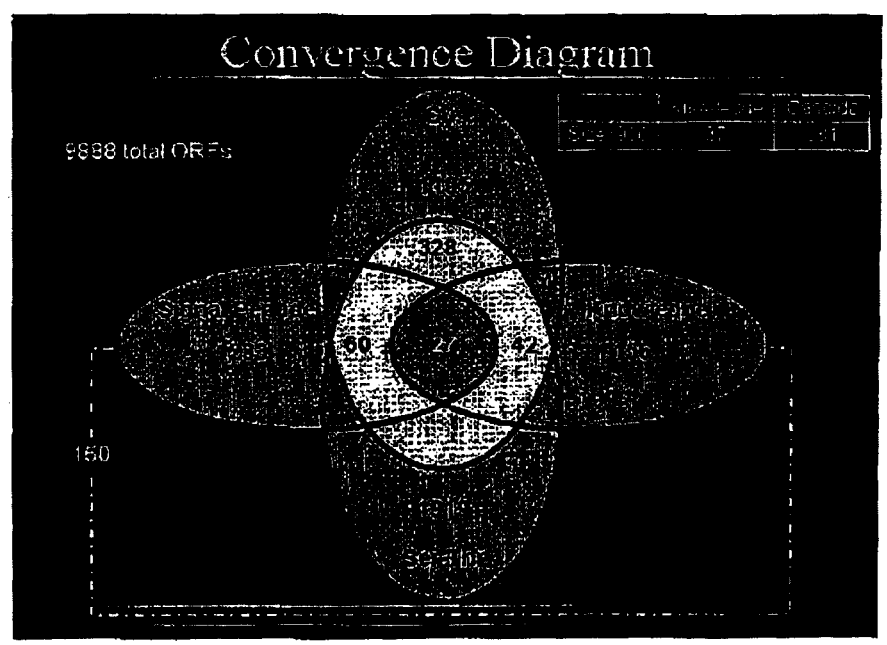
FIG. 8. Representation of sequences identified based on the convergence of factors.

The sequences all identified based on the convergence of the factors described above. The convergence is represented in FIG. 8.

These proteins were identified based on the data obtained from their individual sequences. Specifically, sequences were based on their likelihood of having a signal sequence, as determined in this instance by their PSG and GvH scores obtained using the program PSORT2. PSORT first predicts the presence of signal sequences using McGeoch's method (McGeoch, 1985 *Virus Res.* 3: 271) as modified (http://psort.nibb.acjp/helpwww.html). PSORT2 considers the N-terminal positively-charged region (N-region) and the central hydrophobic region (H-region) of signal sequences. A discriminant score is calculated from the three values: length of H-region, peak value of H-region and net charge of N-region. These results are summarized in "PSG" (formerly known as "mcG"). A large positive discriminant score means a high possibility to posses a signal sequence, but it is unrelated to the possibility of the protein being cleaved. The sequences are further analyzed for their likelihood of a GPI anchor (GPI), likelihood of a transmembrane domain (TM), number of cysteines present (CYS), number of serines and threonines (ST), and the size of the protein in amino acids (Size).

Next, PSORT applies von Heijne's method of signal sequence recognition (Heijne, 1986 *Nucl. Acids Res.* 14: 4683). Heijne's method is a weight-matrix method and incorporates the information of consensus pattern around the cleavage cites (i.e. the "(−3,−1) rule"), and the feature of the H-region. Thus, it can be used to detect signal-anchor sequences. The output score of this "GvH" is the original weight-matrix score (for eukaryotes) subtracted by 3.5. A large positive output means a high possibility that it has a cleavable signal sequence. The position of possible cleavage site, i.e. the most C-terminal position of a signal sequence, is also reported.

In contrast, all proteins linked to the glycosyl-phosphatidylinositol (GPI) moiety is thought to be anchored at the extracellular surface of the plasma membrane or to the cell wall. In addition, GPI anchor plays some roles on the protein sorting in polarized cells. Although much is known about the biosynthesis of GPI-anchor (see for example the review by Takeda et al., 1995 *Trends Biochem. Sci.*, 20: 367), PSORT predicts GPI-anchored proteins by empirical knowledge that many of them are the type Ia membrane proteins with very short cytoplasmic tail (i.e., within 10 residues). A prediction of a GPI anchor by PSORT does increase the likelihood of it being present in the protein of interest, but does not preclude others from having it when they are not predicted to have one.

This data is presented Table 4 below:

TABLE 4

| PROT. fasta.psort | PSG | GvH | GPI | TM | CYS | ST | Size |
|---|---|---|---|---|---|---|---|
| orf6.358 | −4.4 | −11.26 | 0 | 0 | 6 | 14.49 | 849 |
| orf6.1732 | −10.62 | −8.09 | 0 | 0 | 6 | 16.76 | 1659 |
| orf6.3968 | −10.62 | −8.09 | 0 | 0 | 0 | 20.85 | 283 |
| orf6.8118 | 3.86 | 0.46 | 0 | 0 | 4 | 26.94 | 271 |
| orf6.3713 | 4.81 | −0.24 | 0 | 2 | 4 | 21.26 | 701 |
| LIP5 | 6.43 | −0.27 | 0 | 0 | 4 | 12.96 | 463 |
| AAF1 | −2.84 | −9.11 | 0 | 0 | 3 | 20.26 | 612 |
| ALS1 | 5.59 | 1.3 | 0 | 0 | 10 | 36.9 | 1260 |
| ALS3 | 4.39 | 0.32 | 0 | 0 | 11 | 34.23 | 1119 |
| ALS8 | 4.39 | 0.32 | 0 | 0 | 11 | 34.29 | 1047 |
| ALS5 | 5.59 | 1.69 | 0 | 0 | 11 | 38.2 | 1419 |
| BGL2 | 4.54 | −1.96 | 0 | 0 | 4 | 16.23 | 308 |
| CHS1 | −4.4 | −12.51 | 0 | 7 | 13 | 15.98 | 1026 |
| CHS2 | −11.53 | −9.72 | 0 | 5 | 12 | 13.97 | 1009 |
| CHS3 | −17.63 | −12.95 | 0 | 6 | 21 | 14.26 | 1213 |
| CHT1 | 6.18 | 1.98 | 1 | 1 | 8 | 22.51 | 462 |
| CHT2 | 4.6 | 0.32 | 0 | 0 | 13 | 25.04 | 583 |
| CHT3 | 5.95 | 2.05 | 0 | 0 | 6 | 35.8 | 567 |
| CSA1 | 5.81 | 0 | 0 | 9 | 44 | 28.6 | 1203 |
| EFG1 | −4.4 | −11.99 | 0 | 0 | 1 | 17.75 | 552 |
| FKS1 | −4.4 | −18.18 | 0 | 15 | 26 | 11.33 | 1897 |
| FKS2 | −0.9 | −0.89 | 0 | 11 | 20 | 14.13 | 1090 |
| FKS3 | −4.4 | −7.96 | 0 | 15 | 27 | 12.8 | 1640 |
| HEX1 | 5.38 | −3.28 | 0 | 1 | 8 | 13.17 | 562 |
| HWP1 | 4.13 | −4.5 | 0 | 1 | 17 | 28.86 | 634 |
| HYR1 | 6.9 | −1.71 | 1 | 1 | 11 | 31.48 | 937 |
| LIP1 | 7.22 | 3.08 | 0 | 0 | 4 | 15.81 | 468 |
| PHR1 | 5.32 | 1.16 | 1 | 1 | 14 | 20.44 | 548 |
| PHR2 | 4.6 | −0.66 | 1 | 1 | 14 | 21.79 | 546 |
| PLB99 | 4.75 | −3.52 | 0 | 1 | 9 | 17.02 | 605 |
| SAP1 | 6.39 | −0.59 | 0 | 0 | 4 | 16.37 | 391 |
| SAP2 | 6.39 | −2.03 | 0 | 0 | 4 | 17.59 | 398 |
| SAP3 | 6.39 | −1.91 | 0 | 0 | 4 | 18.09 | 398 |
| SAP4 | 6.59 | 1.67 | 0 | 0 | 4 | 16.07 | 417 |
| SAP5 | 6.59 | 1.67 | 0 | 0 | 4 | 16.03 | 418 |
| SAP6 | −0.21 | −0.58 | 0 | 0 | 5 | 15.79 | 418 |

TABLE 4-continued

| PROT. fasta.psort | PSG | GvH | GPI | TM | CYS | ST | Size |
|---|---|---|---|---|---|---|---|
| SAP7 | 3.54 | 2.92 | 0 | 0 | 5 | 19.56 | 588 |
| SAP8 | 5.59 | 1.57 | 0 | 0 | 4 | 23.21 | 405 |
| SAP9 | 4.7 | 2.64 | 1 | 1 | 4 | 22.06 | 544 |
| XOG1 | 5.54 | −2.89 | 0 | 1 | 4 | 10.5 | 438 |
| KRE9 | 6.44 | −1.6 | 0 | 0 | 3 | 26.2 | 271 |
| ALS2 | 6.11 | 5.35 | 0 | 0 | 9 | 27.78 | 468 |
| ALS4 | 6.11 | 5.35 | 0 | 0 | 11 | 34.73 | 1523 |
| PLB98 | 6.49 | −1.38 | 0 | 0 | 9 | 14.8 | 608 |
| MP65 | 5.75 | −1.73 | 0 | 0 | 6 | 20.58 | 379 |
| PLB97 | 5.86 | 0.34 | 1 | 1 | 9 | 22.28 | 754 |
| ALS6 | 5.27 | −1.86 | 0 | 0 | 12 | 38.67 | 1443 |
| ALS7 | 4.39 | 2 | 0 | 0 | 9 | 37.4 | 2297 |
| PHR3 | 6.75 | −2.89 | 0 | 1 | 8 | 11.91 | 487 |
| LIP2 | 6.74 | 4.21 | 0 | 0 | 4 | 14.16 | 466 |
| SAP10 | −4.4 | −0.68 | 0 | 1 | 5 | 17.69 | 441 |
| LIP3 | 5.85 | 4.34 | 0 | 0 | 5 | 13.16 | 471 |
| LIP4 | 8.56 | 4.12 | 0 | 0 | 4 | 11.98 | 459 |
| LIP8 | 6.26 | 1.19 | 0 | 0 | 5 | 15.43 | 460 |
| LIP6 | 6.79 | 4.16 | 0 | 0 | 4 | 14.9 | 463 |
| LIP7 | 8 | 0.01 | 0 | 0 | 7 | 13.85 | 426 |
| LIP9 | 6.43 | 1.27 | 0 | 0 | 4 | 14.35 | 453 |
| LIP10 | 7.79 | 4.2 | 0 | 0 | 4 | 15.48 | 465 |
| RBT1 | 1.94 | −5.77 | 0 | 0 | 16 | 31.6 | 750 |
| WAP1 | 5.81 | 0 | 0 | 6 | 36 | 28.98 | 1018 |
| orf6.162 | 3.88 | −0.67 | 0 | 0 | 20 | 41.35 | 1122 |
| orf6.288 | 8.56 | 4.12 | 0 | 0 | 4 | 11.76 | 459 |
| orf6.474 | 5.6 | −0.19 | 0 | 0 | 4 | 21.04 | 385 |
| orf6.553 | −4.4 | −12.55 | 0 | 0 | 10 | 17.98 | 684 |
| orf6.708 | 5.75 | −1.73 | 0 | 0 | 6 | 20.63 | 378 |
| orf6.795 | 6.31 | 3.38 | 0 | 0 | 5 | 18.78 | 394 |
| orf6.796 | −2.74 | −9.14 | 0 | 0 | 7 | 17.11 | 304 |
| orf6.799 | 5.69 | 3.04 | 0 | 0 | 8 | 23.18 | 384 |
| orf6.857 | −4.4 | −5.89 | 0 | 1 | 7 | 38.45 | 515 |
| orf6.1059 | 6.31 | 3.38 | 0 | 0 | 2 | 18.44 | 358 |
| orf6.1114 | 7.42 | 1.57 | 0 | 0 | 8 | 32.89 | 894 |
| orf6.1115 | −6.91 | −8.29 | 0 | 0 | 2 | 45.18 | 467 |
| orf6.1231 | 4.7 | −0.58 | 0 | 0 | 2 | 29.36 | 453 |
| orf6.1293 | 5.29 | −1.49 | 1 | 1 | 9 | 14.6 | 452 |
| orf6.1310 | 2.72 | −6.23 | 0 | 0 | 3 | 37.12 | 1029 |
| orf6.1331 | 4.71 | −1.53 | 0 | 0 | 10 | 38.02 | 434 |
| orf6.1377 | 6.11 | 5.35 | 0 | 0 | 12 | 35.06 | 1586 |
| orf6.1488 | −4.4 | −12.19 | 0 | 1 | 6 | 15.89 | 428 |
| orf6.1614 | 4.39 | 0.32 | 0 | 0 | 8 | 32.28 | 886 |
| orf6.1639 | 5.01 | −1.74 | 1 | 1 | 9 | 22.77 | 470 |
| orf6.1902 | 5.91 | 0.58 | 0 | 0 | 5 | 15.43 | 363 |
| orf6.1967 | 1.14 | −7.39 | 0 | 0 | 3 | 24.07 | 162 |
| orf6.1985 | 6.49 | −1.38 | 0 | 0 | 9 | 14.61 | 609 |
| orf6.2069 | −1.72 | −11.8 | 0 | 0 | 5 | 11.99 | 392 |
| orf6.2071 | 4.96 | −0.82 | 0 | 0 | 11 | 22.49 | 418 |
| orf6.2204 | 6.59 | 1.67 | 0 | 0 | 4 | 15.79 | 418 |
| orf6.2346 | −4.4 | −7.43 | 0 | 0 | 6 | 25 | 324 |
| orf6.2395 | 5.44 | −9.02 | 0 | 1 | 5 | 13.33 | 525 |
| orf6.2398 | 6.75 | 3.58 | 0 | 0 | 4 | 15.81 | 468 |
| orf6.2643 | 8.56 | 2.98 | 0 | 0 | 4 | 15.22 | 460 |
| orf6.2688 | 5.59 | 1.57 | 0 | 0 | 4 | 23.21 | 405 |
| orf6.2920 | 5.95 | 5.19 | 0 | 0 | 9 | 32.88 | 952 |
| orf6.2929 | −3.04 | −0.2 | 0 | 0 | 7 | 38.42 | 367 |
| orf6.2978 | −4.4 | −8.31 | 0 | 1 | 3 | 17.14 | 525 |
| orf6.3000 | 6.11 | 5.35 | 0 | 0 | 9 | 34.23 | 1756 |
| orf6.3074 | 6.11 | 5.35 | 0 | 0 | 9 | 34.97 | 1593 |
| orf6.3097 | 4.54 | −1.96 | 0 | 0 | 4 | 16.23 | 308 |
| orf6.3143 | 6.9 | −1.71 | 1 | 1 | 11 | 31.48 | 937 |
| orf6.3288 | 4.6 | −1.56 | 1 | 0 | 11 | 26.45 | 533 |
| orf6.3499 | −4.4 | −12.51 | 0 | 7 | 13 | 15.89 | 1026 |
| orf6.3505 | 7.74 | 1.31 | 1 | 1 | 4 | 19.44 | 504 |
| orf6.3591 | 4.71 | −1.53 | 1 | 1 | 10 | 39.46 | 517 |
| orf6.3600 | 7.49 | −5.62 | 0 | 1 | 7 | 12.03 | 424 |
| orf6.3624 | 6.59 | 1.67 | 0 | 0 | 4 | 15.55 | 418 |
| orf6.3635 | 3.54 | 2.92 | 0 | 0 | 4 | 19.56 | 588 |
| orf6.3690 | 4.75 | −3.52 | 0 | 1 | 9 | 17.02 | 605 |
| orf6.3785 | −4.4 | −18.18 | 0 | 15 | 26 | 11.28 | 1897 |
| orf6.3803 | 6.59 | 1.67 | 0 | 0 | 4 | 16.07 | 417 |
| orf6.3873 | 6.95 | −2.92 | 0 | 1 | 20 | 13.73 | 641 |
| orf6.3969 | 5.03 | 0.4 | 1 | 1 | 4 | 23.73 | 413 |
| orf6.4005 | 5.12 | −2 | 0 | 1 | 5 | 20.76 | 578 |
| orf6.4037 | 5.86 | 0.34 | 1 | 1 | 9 | 22.41 | 754 |
| orf6.4068 | −9.47 | −12.32 | 0 | 2 | 6 | 16.6 | 717 |
| orf6.4149 | 4.28 | 0.31 | 0 | 0 | 10 | 23.08 | 468 |
| orf6.4388 | 6.01 | 1.76 | 1 | 1 | 6 | 36.23 | 1311 |
| orf6.4501 | 2.45 | −10 | 0 | 0 | 4 | 13.78 | 283 |
| orf6.4590 | 4.39 | −0.62 | 1 | 1 | 4 | 34.7 | 219 |
| orf6.4644 | 6.39 | −0.59 | 0 | 0 | 4 | 16.37 | 391 |
| orf6.4725 | 5.69 | −0.62 | 1 | 1 | 6 | 36.43 | 1249 |
| orf6.4883 | 4.13 | −4.5 | 0 | 1 | 17 | 28.86 | 634 |
| orf6.4889 | 1.94 | −5.77 | 0 | 1 | 16 | 31.09 | 714 |
| orf6.4915 | 5.59 | 1.69 | 0 | 0 | 10 | 38.01 | 1347 |
| orf6.5053 | 6.44 | −1.6 | 0 | 0 | 3 | 26.57 | 271 |
| orf6.5153 | 5.6 | −0.19 | 0 | 0 | 4 | 21.97 | 346 |
| orf6.5166 | −4.4 | −10.13 | 0 | 0 | 10 | 29.16 | 511 |
| orf6.5210 | 6.74 | 4.21 | 0 | 0 | 4 | 13.95 | 466 |
| orf6.5227 | −4.4 | −12.55 | 0 | 0 | 10 | 17.86 | 683 |
| orf6.5306 | 6.39 | −2.03 | 0 | 0 | 4 | 17.59 | 398 |
| orf6.5354 | 3.88 | −0.67 | 0 | 0 | 12 | 35.22 | 653 |
| orf6.5940 | 5.22 | −3.19 | 0 | 0 | 26 | 44.05 | 1176 |
| orf6.6053 | −4.4 | −16.26 | 0 | 6 | 21 | 13.68 | 1111 |
| orf6.6176 | −3.93 | −10.48 | 0 | 16 | 26 | 12.48 | 1571 |
| orf6.6206 | −4.4 | −2.45 | 0 | 2 | 9 | 17.41 | 632 |
| orf6.6260 | 4.6 | −0.66 | 1 | 1 | 14 | 21.88 | 544 |
| orf6.6348 | 5.86 | 0.34 | 0 | 0 | 1 | 24.59 | 305 |
| orf6.6575 | 4.28 | 0.31 | 0 | 0 | 5 | 27.62 | 286 |
| orf6.6664 | 6.95 | −1.06 | 1 | 1 | 7 | 13.57 | 479 |
| orf6.6782 | 5.38 | −3.28 | 0 | 1 | 8 | 13.17 | 562 |
| orf6.6957 | 6.43 | −0.27 | 0 | 0 | 4 | 12.96 | 463 |
| orf6.6963 | −4.4 | −4.84 | 0 | 0 | 4 | 13.89 | 252 |
| orf6.6964 | 6.43 | 1.27 | 0 | 0 | 1 | 15.84 | 221 |
| orf6.7314 | 4.7 | 2.64 | 1 | 1 | 4 | 22.61 | 544 |
| orf6.7355 | 5.85 | 4.34 | 0 | 1 | 6 | 13.59 | 471 |
| orf6.7448 | 3.81 | −0.91 | 1 | 1 | 8 | 18.18 | 451 |
| orf6.7480 | 6.11 | 0.81 | 1 | 1 | 12 | 14.19 | 451 |
| orf6.7524 | 5.85 | 2.08 | 1 | 1 | 14 | 20.62 | 548 |
| orf6.7534 | −4.4 | −0.68 | 0 | 2 | 6 | 19.43 | 453 |
| orf6.7977 | 4.38 | 0.92 | 0 | 0 | 11 | 20.16 | 372 |
| orf6.8114 | −12.97 | −10.36 | 0 | 0 | 4 | 11.55 | 502 |
| orf6.8269 | −4.4 | −7.96 | 0 | 4 | 9 | 14.36 | 780 |
| orf6.8270 | −5.56 | −8.85 | 0 | 11 | 19 | 11.57 | 864 |
| orf6.8379 | −11.53 | −9.72 | 0 | 5 | 12 | 13.97 | 1009 |
| orf6.8560 | 4.39 | 2 | 0 | 0 | 9 | 35.4 | 2000 |
| orf6.8574 | 5.27 | −1.86 | 0 | 0 | 11 | 38.8 | 1366 |
| orf6.8620 | −16.17 | −12.6 | 0 | 6 | 11 | 12.85 | 1105 |
| orf6.8724 | 6.54 | −2.25 | 0 | 2 | 9 | 34.93 | 1526 |
| orf6.8769 | 6.18 | 1.98 | 1 | 1 | 8 | 22.51 | 462 |
| ALS9 | 7.42 | 1.57 | 0 | 0 | 8 | 29.7 | 468 |
| Ca20C1.17 | 3.06 | −0.36 | 0 | 0 | 16 | 16.58 | 597 |
| orf6.129 | 6.38 | −3.23 | 0 | 0 | 34 | 28.24 | 687 |
| orf6.848 | 8.57 | 0.79 | 1 | 0 | 15 | 18.07 | 559 |
| orf6.1030 | 7.05 | −0.41 | 0 | 0 | 12 | 45.16 | 713 |
| orf6.1249 | 5.44 | 1.58 | 0 | 0 | 22 | 29.32 | 590 |
| orf6.1759 | 2.46 | 1.42 | 1 | 1 | 12 | 27.45 | 765 |
| orf6.1922 | 5.44 | 1.58 | 0 | 0 | 22 | 28.43 | 598 |
| orf6.2030 | −6.61 | −9.72 | 0 | 1 | 17 | 13.2 | 356 |
| orf6.2101 | 3.06 | −0.36 | 0 | 0 | 16 | 16.58 | 597 |
| orf6.2332 | 7.95 | −2.02 | 0 | 1 | 15 | 14.34 | 1332 |
| orf6.2415 | −4.4 | 0.14 | 0 | 1 | 12 | 35.64 | 101 |
| orf6.3431 | 7.84 | 3.04 | 1 | 1 | 17 | 24.44 | 311 |
| orf6.3558 | 4.11 | −6.42 | 0 | 1 | 11 | 14.06 | 690 |
| orf6.3897 | −4.4 | −13.53 | 0 | 1 | 21 | 15.01 | 1432 |
| orf6.3954 | 6.64 | 2.14 | 0 | 1 | 11 | 17.59 | 1393 |
| orf6.4050 | 5.22 | 0.73 | 0 | 0 | 16 | 26.07 | 399 |
| orf6.4229 | −4.4 | −10.39 | 0 | 1 | 15 | 15.13 | 1441 |
| orf6.4292 | 5.71 | −1.29 | 1 | 1 | 18 | 46.22 | 753 |
| orf6.4430 | 2.46 | 1.42 | 1 | 1 | 12 | 27.84 | 765 |
| orf6.5138 | 3.4 | −2.79 | 0 | 0 | 16 | 18.4 | 413 |
| orf6.5529 | 5.01 | −1.04 | 1 | 1 | 13 | 33.26 | 872 |
| orf6.7401 | 3.91 | −2.65 | 0 | 0 | 18 | 28.35 | 575 |
| orf6.7594 | 5.7 | −1.87 | 0 | 1 | 11 | 23.24 | 370 |
| orf6.7959 | 1.03 | −7.49 | 0 | 0 | 19 | 19.03 | 1077 |

TABLE 4-continued

| PROT. fasta.psort | PSG | GvH | GPI | TM | CYS | ST | Size |
|---|---|---|---|---|---|---|---|
| orf6.8067 | -4.4 | -4.46 | 0 | 0 | 13 | 22.56 | 266 |
| orf6.8151 | 5.7 | 2.48 | 0 | 1 | 12 | 34.62 | 491 |
| orf6.8214 | 5.96 | -0.87 | 0 | 0 | 10 | 30.99 | 142 |
| orf6.8265 | 0.36 | -6.49 | 0 | 0 | 10 | 12.05 | 556 |
| orf6.8457 | 6.91 | -2.12 | 0 | 1 | 11 | 15.27 | 976 |
| orf6.8635 | 4.34 | -1.82 | 0 | 0 | 15 | 24.46 | 511 |
| orf6.8640 | 6.95 | 2.74 | 0 | 0 | 10 | 24.33 | 563 |
| orf6.8725 | -4.4 | -3.59 | 0 | 1 | 10 | 19.15 | 757 |
| orf6.9090 | -4.4 | -16.69 | 0 | 1 | 24 | 15.39 | 1839 |
| [AI:7500742175] | 4.96 | -0.82 | 0 | 0 | 11 | 22.8 | 421 |
| [AI:7500742368] | -1.26 | 0.32 | 0 | 0 | 10 | 23.06 | 464 |
| [AI:7500743848] | 8.85 | -7.27 | 0 | 1 | 11 | 17.86 | 336 |
| [AI:7500744875] | 3.46 | -1.71 | 0 | 1 | 21 | 28.76 | 452 |
| [AI:7500746723] | -6.56 | 4.13 | 0 | 1 | 11 | 20.39 | 716 |
| [AI:7500748186] | 4.34 | -7.77 | 0 | 0 | 13 | 19.15 | 564 |
| [AI:7500749610] | 5.59 | 1.3 | 0 | 0 | 11 | 33.08 | 1191 |
| [AI:7500758296] | -4.83 | -3.61 | 0 | 1 | 16 | 13.51 | 348 |
| [AI:7500758378] | 6.31 | 3.38 | 0 | 0 | 11 | 17.79 | 714 |
| [AI:7500760864] | 4.44 | -2.37 | 0 | 0 | 17 | 36.28 | 317 |
| [AI:7500763321] | 4.11 | -3.89 | 0 | 1 | 11 | 13.4 | 694 |
| [AI:7500764518] | 4.34 | -4.26 | 0 | 0 | 13 | 18.17 | 644 |
| [AI:7500766693] | 3.91 | -2.65 | 0 | 0 | 18 | 27.71 | 581 |
| [AI:7500767653] | 6.54 | -0.72 | 0 | 0 | 12 | 30.92 | 262 |
| [AI:7500768951] | -2.1 | -0.41 | 0 | 1 | 13 | 34.22 | 491 |
| [AI:7500770709] | 5.96 | -4.33 | 0 | 1 | 16 | 17.45 | 1060 |
| [AI:7500771688] | 6.9 | -4.37 | 0 | 1 | 11 | 16.47 | 759 |
| [AI:7500772763] | 2.29 | -5.53 | 0 | 0 | 14 | 17.04 | 493 |
| orf6.6934.prot | 8.16 | 1.82 | 0 | 0 | 9 | 19 | 300 |

The serines and threonines (ST) is represented in percent of total amino acids present in the polypeptide. "TM" means transmembrane domain. One could readily determine the percent similarity and percent identity between the above sequences and any description identified with a related sequence. However, the description and percent similarity and percent identity must be weighed with the other factors, such as cysteine content, serine/threonine content, size and the like.

Those proteins that passed one or two of the sets of the knowledge mining or had sequence properties were then amassed and are listed in Table 5. Table 5 contains the listing of open reading frames (ORFs) from the 210 targets identified as compared to a database of known sequences. This comparison was done using the BLAST algorithm and the top hit of the analysis is described for each protein. The orf or protein designation is in the first column. The second and third columns contain the SEQ ID NO for the nucleotide and amino acid sequences, respectively. The length of the nucleotide and amino acid sequence is described in the fifth and sixth columns, respectively. The BLAST score and probability are listed in the seventh and eighth columns. The description of the orf is the ninth column. One skilled in the art would appreciate these BLAST hits in the ninth column describes the function of the target. In some cases, the sequences in Table 5 would be considered orthologs, proteins having the same function in different species.

| ORF | NT Seq ID | AA Seq ID | NT ORF Length | AA ORF Length | Score | Probability | Description |
|---|---|---|---|---|---|---|---|
| AAF1 | 1 | 211 | 2913 | 612 | 3200 | 0 | sp:[LN:ADF1_CANAL] [AC:P46589] [GN:ADF1:AAF1:AAF1] [OR:*Candida albicans*] [SR:,Yeast] [DE:Adherence factor (Adhesion and aggregation mediating surface antigen)] [SP:P46589] [DB:swissprot] >gp:[GI:1177215] [LN:CAU44747] [AC:U44747] [PN:AAF1] [GN:AAF1] [FN:surface antigen mediating adhesion and] [OR:*Candida albicans*] [DB:genpept-pln4] [DE:*Candida albicans* adhesion and aggregation mediating surface antigen(AAF1) gene, complete cds.] [LE:815] [RE:2653] [DI:direct] |
| ALS1 | 2 | 212 | 3786 | 1260 | 6495 | 0 | sp:[LN:ALS1_CANAL] [AC:P46590] [GN:ALS1] [OR:*Candida albicans*] [SR:,Yeast] [DE:Agglutinin-like; protein 1 precursor] [SP:P46590] [DB:swissprot] >gp:[GI:7687905] [LN:YSAALS1] [AC:L25902] [PN:agglutinin-like protein] [GN:ALS1] [OR:*Candida albicans*] [DB:genpept-pln5] [DE:*Candida albicans* agglutinin-like sequence (ALS1) gene, complete cds.] [LE:1] [RE:3783] [DI:direct] |
| ALS2 | 3 | 213 | 1404 | 468 | 2437 | 3.30E-255 | gp:[GI:3598675] [LN:CANALS2S1] [AC:AF024582] [PN:agglutinin-like protein] [GN:ALS2] [OR:*Candida albicans*] [DB:genpept-pln4] [DE:*Candida albicans* agglutinin-like protein (ALS2) gene, 5' partial cds.] [LE:1] [RE:>1404] [DI:direct] |
| ALS3 | 4 | 214 | 3360 | 1119 | 5896 | 0 | sp:[LN:ALS3_CANAL] [AC:O74623] [GN:ALS3] [OR:*Candida albicans*] [SR:,Yeast] [DE:Agglutinin-like protein 3 precursor] [SP:O74623] [DB:swissprot] >gp:[GI:3273415] [LN:CAU87956] [AC:U87956] [PN:agglutinin-like protein] [GN:ALS3] [OR:*Candida albicans*] [DB:genpept-pln4] [DE:*Candida albicans* agglutinin-like protein (ALS3) gene, complete cds.] [LE:1] [RE:3360] [DI:direct] |
| ALS4 | 5 | 215 | 4569 | 1523 | 8002 | 0 | gp:[GI:10952736] [LN:AF272027] [AC:AF272027] [PN:agglutinin-like protein] [OR:*Candida albicans*] [DB:genpept-pln2] [DE:*Candida albicans* agglutinin-like protein mRNA, partial cds.] [LE:1] [RE:>4569] [DI:direct] |
| ALS5 | 6 | 216 | 4723 | 1419 | 7131 | 0 | sp:[LN:ALA1_CANAL] [AC:O13368] [GN:ALA1:ALS5] [OR:*Candida albicans*] [SR:,Yeast] [DE:Agglutinin-like protein ALA1 precursor (Agglutinin-like adhesin)] [SP:O13368] [DB:swissprot] >pir:[LN:T30531] [AC:T30531] [PN:agglutinin-like adhesin] [GN:ALA1] [CL:yeast glucan 1,4-alpha-glucosidase homolog:glucan 1,4-alpha-glucosidase homology] [OR:*Candida albicans*] [DB:pir2] >gp:[GI:2522219] [LN:AF025429] [AC:AF025429] [PN:agglutinin-like adhesin] [GN:ALA1] [FN:cell adhesion protein] [OR:*Candida albicans*] [DB:genpept-pln1] [DE:*Candida albicans* agglutinin-like adhesin (ALA1) gene, complete cds.] [LE:327] [RE:4586] [DI:direct] |

-continued

| ORF | NT Seq ID | AA Seq ID | NT ORF Length | AA ORF Length | Score | Probability | Description |
|---|---|---|---|---|---|---|---|
| ALS6 | 7 | 217 | 4332 | 1443 | 7240 | 0 | gp:[GI:5326752] [LN:AF075293] [AC:AF075293] 8 PN:agglutinin-like protein 6] [GN:ALS6] [OR:*Candida albicans*] [DB:genpept-pln2] [DE:*Candida albicans* strain 1161 agglutinin-like protein 6 (ALS6) gene, complete cds.] [LE:1] [RE:4332] [DI:direct] |
| ALS7 | 8 | 218 | 6897 | 2297 | 11410 | 0 | gp:[GI:9754771] [LN:AF201684] [AC:AF201684] [PN:agglutinin-like protein Als7p] [GN:ALS7] [OR:*Candida albicans*] [DB:genpept-pln2] [DE:*Candida albicans* agglutinin-like protein Als7p (ALS7) gene, complete cds.] [LE:1] [RE:6894] [DI:direct] |
| ALS8 | 9 | 219 | 3782 | 1047 | 5512 | 0 | gp:[GI:4105851] [LN:AF051313] [AC:AF051313] [PN:agglutiin-like cell surface protein] [GN:ALS8] [FN:involved in cell-cell adhesion] [OR:*Candida albicans*] [DB:genpept-pln1] [DE:*Candida albicans* agglutinin-like cell surface protein (ALS8) gene, complete cds.] [NT:hypha-specific cell surface glycoprotein; similar] [LE:697] [REL3840] [DI:direct] |
| ALS9 | 10 | 220 | 1404 | 468 | 2444 | 6.00E-256 | gp:[GI:12656146] [LN:AF229989S1] [AC:AF229989] [PN:agglutinin-like protein] [GN:ALS9] [OR:*Candida albicans*] [DB:genpept-pln2] [DE:*Candida albicans* agglutinin-like protein (ALS9) gene, partial cds.] [LE:1] [RE:>1404] [DI:direct] |
| BGL2 | 11 | 221 | 1149 | 308 | 1614 | 8.20E-168 | sp:[LN:BGL2_CANAL] [AC:P43070] [GN:BGL2] [OR:*Candida albicans*] [SR:,Yeast] [EC:3.2.1.58] [DE:glucanase)] [SP:P43070] [DB:swissprot] >gp:[GI:532776] [LN:CAU12975] [AC:U12975] [PN:beta-1,3 glucan transferase] [GN:BGL2] [OR:*Candida albicans*] [DB:genpept-pln4] [DE:*Candida albicans* ATCC 10261 beta-1,3 glucan transferase (BGL2) gene, complete cds.] [NT:secreted, cell wall] [LE:122] [RE:1048] [DI:direct] |
| CHS1 | 12 | 222 | 42565 | 1026 | 5391 | 0 | pir:[LN:T18220] [AC:T18220] [PN:chitin synthase] [GN:Chs1] [CL:chitin synthase chsA] [OR:*Candida albicans*] [DB:pir2] >gp:[GI:3850147] [LN:CAC35A5] [AC:AL033396] [PN:chitin synthase] [GN:Chs1] [OR:*Candida albicans*] [DB:genpept-pln4] [DE:*C. albicans* cosmid Ca35A5.] [NT:Ca35A5.04, Chs1 gene, len: 1026 aa, CHS1_CANAL] [LE:20808] [RE:23888] [DI:direct] |
| CHS2 | 13 | 223 | 3885 | 1009 | 5308 | 0 | sp:[LN:CHS2_CANAL] [AC:P30572] [GN:CHS2] [OR:*Candida albicans*] [SR:,Yeast] [EC:2.4.1.16] [DE:transferase 2)] [SP:P30572] [DB:swissprot] >gp:[GI:7687906] [LN:YSACS2A] [AC:M82937] [PN:chitin synthase 2] [GN:CHS2] [OR:*Candida albicans*] [DB:genpept-pln5] [DE:*Candida albicans* chitin synthase 2 (CHS2) gene, complete cds.] [LE:703] [RE:3732] [DI:direct] |
| CHS3 | 14 | 224 | 4610 | 1213 | 6416 | 0 | sp:[LN:CHS3_CANAL] [AC:P30573] [GN:CHS3] [OR:*Candida albicans*] [SR:,Yeast] [EC:2.4.1.16] [DE:transfearse 3) (Class-IV chitin synthase 3)] [SP:P30573] [DB:swissprot] >gp:[GI:218362] [LN:YSACACHS3] [AC:D13454] [PN:chitin synthase III] [GN:CACHS3] [OR:*Candida albicans*] [SR:*Candida albicans* (strain:IFO1060) DNA] [DB:genpept-pln5] [DE:*Candida albicans* CACHS3 gene for chitin synthase III.] [LE:268] [RE:3909] [DI:direct] |
| CHT1 | 15 | 225 | 2420 | 462 | 2397 | 5.80E-251 | gp:[GI:15530178] [LN:CAU36490] [AC:U36490] [PN:chitinase] [GN:CHT1] [OR:*Candida albicans*] [DB:genprpt-pln4] [DE:*Candida albicans* chitinase (CHT1) gene, complete cds.] [LE:444] [RE:1832] [DI:direct] |
| CHT2 | 16 | 226 | 2348 | 583 | 2987 | 0 | sp:[LN:CHI2_CANAL] [AC:P40953] [GN:CHT2] [OR:*Candida albicans*] [SR:,Yeast] [EC:3.2.1.14] [DE:Chitinase 2 precursor,] [SP:P40953] [DB:swissprot] >gp:[GI:571427] [LN:CAU15800] [AC:U15800] [PN:chitinase] [GN:cht2] [OR:*Candida albicans*] [DB:genpept-pln4] [DE:*Candida albicans* chitinase (cht2) gene, complete cds.] [LE:201] [RE:1952] [DI:direct] |
| CHT3 | 17 | 227 | 2138 | 567 | 2881 | 0 | sp:[LN:CHI3_CANAL] [AC:P40954] [GN:CHT3] [OR:*Candida albicans*] [SR:,Yeast] [EC:3.2.1.14] [DE:Chitinase 3 precursor,] [SP:P40954] [DB:swissprot] >gp:[GI:571429] [LN:CAU15801] [AC:U15801] [PN:chitinase] [GN:cht3] [OR:*Candida albicans*] [DB:genpept-pln4] [DE:*Candida albicans* chitinase (cht3) gene, complete cds.] [LE:140] [RE:1843] [DI:direct] |
| CSA1 | 18 | 228 | 4291 | 1203 | 6073 | 0 | pir:[LN:T17415] [AC:T17415] [PN:mycelial surface antigen CSA1 precursor] [GN:CSA1] [OR:*Candida albicans*] [DB:pir2] >gp:[GI:3406798] [LN:AF080221] [AC:AF080221] [PN:mycelial surface antigen precursor] [GN:CSA1] [OR:*Candida albicans*] [DB:genpept-pln2] [DE:*Candida albicans* mycelial surface antigen precursor (CSA1) gene, complete cds.] [NT:cell wall protein; Csa1p; differential expression] [LE:515] [RE:4126] [DI:direct] |
| Ca20C1.17 | 19 | 229 | 37968 | 597 | 3253 | 0 | gp:[GI:3850137] [LN:CAC20C1] [AC:AL033391] [PN:conserved hypothetical protein] [GN:Ca20C1.17] [OR:*Candida albicans*] [DB:genpept-pln4] [DE:*C. albicans* cosmid Ca20C1.] [NT:Ca20C1.17, unknown, len: 597 aa, hydrophobic region] [LE:24641] [RE:26434] [DI:direct] |
| EFG1 | 20 | 230 | 2517 | 552 | 2900 | 0 | sp:[LN:EFG1_CANAL] [AC:P43064] [GN:EFG1:EFG] [OR:*Candida albicans*] [SR:,Yeast] [DE:Enhanched filamentous growth protein] [SP:P43064] [DB:swissprot] >gp:[GI:832907] [LN:CAEFGTF] [AC:Z32687] [PN:putative transcription factor] [GN:EFG] [OR:*Candida albicans*] [DB:genpept-pln4] [DE:*Candida albicans* EFG gene for putative transcription factor.] [SP:P43064] [LE:4449] [RE:6107] [DI:direct] |
| FKS1 | 21 | 231 | 6473 | 1897 | 10070 | 0 | gp:[GI:2274847] [LN:D88815] [AC:D88815] [PN:beta-1,3-glucan synthase catalytic subunit 1] [GN:GSC1] [OR:*Candida albicans*] [SR:*Candida albicans* DNA] [DB:genpept-pln4] [DE:*Candida albicans* GSC1 gene for beta-1,3-glucan synthase catalytic subunit 1, complete cds.] [LE:708] [RE:6401] [DI:direct] |

-continued

| ORF | NT Seq ID | AA Seq ID | NT ORF Length | AA ORF Length | Score | Probability | Description |
|---|---|---|---|---|---|---|---|
| FKS2 | 22 | 232 | 4358 | 1090 | 5661 | 0 | pir:[LN:T30576] [AC:T30576] [PN:glucan synthase] [GN:GSL1] [OR:*Candida albicans*] [DB:pir2] >gp:[GI:2274849] [LN:D88816] [AC:D88816] [PN:glucan synthase] [GN:GSL1] [OR:*Candida albicans*] [SR:*Candida albicans* DNA] [DB:genpept-pln4] [DE:*Candida albicans* GSL1 gene for glucan synthase, complete cds.] [LE:1053] [RE:4325] [DI:direct] |
| FKS3 | 23 | 233 | 4923 | 1640 | 8603 | 0 | gp:[GI:2274776] [LN:AB001077] [AC:AB001077] [PN:glucan synthase] [GN:GSL2] [OR:*Candida albicans*] [SR:*Candida albicans* DNA] [DB:genpept-pln1] [DE:*Candida albicans* GSL2 gene for glucan synthase, complete cds.] [LE:1] [RE:4923] [DI:direct] |
| HEX1 | 24 | 234 | 2541 | 562 | 2999 | 0 | sp:[LN:HEX1_CANAL] [AC:P43077] [GN:HEX1] [OR:*Candida albicans*] [SR:,Yeast] [EC:3.2.1.52] [DE:glucosaminidase) (Beta-GLCNACASE) (Beta-N-acetylhexosaminidase)] [SP:P43077] >gp:[GI:7547263] [LN:YSAHEX1A] [AC:L26488] [PN:hexosaminidase precursor] [GN:HEX1] [OR:*Candida albicans*] [DB:genpept-pln5] [EC:3.2.1.52] [DE:*Candida albicans* hexosaminidase precursor (HEX1) gene, complete cds.] [NT:beta-N-acetylglucosaminidase] [LE:422] [RE:2110] [DI:direct] |
| HWP1 | 25 | 235 | 2188 | 634 | 3346 | 0 | gp:[GI:2275336] [LN:AF001978] [AC:AF001978] [GN:ECE2] [OR:*Candida albicans*] [DB:genpept-pln1] [DE:*Candida albicans* ECE2 gene, complete cds.] [NT:differentially expressed in relation to the extent] [LE:151] [RE:2055] [DI:direct] |
| HYR1 | 26 | 236 | 3000 | 937 | 4787 | 0 | sp:[LN:HYR1_CANAL] [AC:P46591] [GN:HYR1] [OR:*Candida albicans*] [SR:,Yeast] [DE:Hyphally regulated protein precursos] [SP:P46591] [DB:swissprot] >gp:[GI:1052565] [LN:CAHYR1GN] [AC:Z50123] [PN:hyphally regulated protein] [GN:HYR1] [FN:unknown] [OR:*Candida albicans*] [DB:genpept-pln4] [DE:*Candida albicans* HYR1 gene and promoter region.] [SP:P46591] [LE:1890] [RE:4073] [DI:direct] |
| KRE9 | 27 | 237 | 816 | 271 | 1414 | 1.50E-146 | sp:[LN:KRE9_CANAL] [AC:O74226] [GN:KRE9] [OR*Candida albicans*] [SR:,Yeast] [DE:Cell wall synthase protein KRE9 precursor] [SP:O74226] [DB:swissprot] >gp:[GI:345198] [LN:AF069763] [AC:AF069763] [PN:cell wall synthesis protein Kre9p] [GN:KRE9] [FN:cell wall beta-1,6-glucan synthase] [OR:*Candida albicans*] [DB:genpept-pln1] [DE:*Candida albicans* cell wall synthesis protein Kre9p (KRE9) gene, complete cds.] [LE:1] [RE:816] [DI:direct] |
| LIP1 | 28 | 238 | 1961 | 468 | 2429 | 2.30E-254 | gp:[GI:7012685] [LN:AF188894] [AC:AF188894] [PN:secretory lipase 1] [GN:LIP1] [OR:*Candida albicans*] [DB:genpept-pln2] [EC:3.1.1.3] [DE:*Candida albicans* secretory lipase 1 (LIP1) gene, complete cds.] [LE:366] [RE:1772] [DI:direct] |
| LIP10 | 29 | 239 | 1915 | 465 | 2393 | 1.50E-250 | gp:[GI:8809749] [LN:AF:191323] [AC:AF191323] [PN:secretory lipase 10] [GN:Lip10] [OR:*Candida albicans*] [DB:genpept-pln2] [EC:3.1.1.3] [DE:*Candida albicans* secretory lipase 10 (Lip10) gene, complete cds.] [NT:LIP] [LE:331] [RE:1728] [DI:direct] |
| LIP2 | 30 | 240 | 1978 | 466 | 2450 | 1.40E-256 | gp:[GI:6978036] [LN:AF189152] [AC:AF189152] [PN:secretory lipase] [GN:LIP2] [OR:*Candida albicans*] [DB:genpept-pln2] [EC:3.1.1.3] [DE:*Candida albicans* secretory lipase (LIP2) gene, complete cds.] [NT:lipase] [LE:369] [RE:1769] [DI:direct] |
| LIP3 | 31 | 241 | 1901 | 471 | 2465 | 3.60E-258 | gp:[GI:7769752] [LN:AF191316] [AC:AF191316] [PN:secretory lipase 3] [GN:LIP3] [OR:*Candida albicans*] [DB:genpept-pln2] [EC:3.1.1.3] [DE:*Candida albicans* secretory lipase 3 (LIP3) gene, complete cds.] [NT:Lip3; LIP] [LE:332] [RE:1747] [DI:direct] |
| LIP4 | 32 | 242 | 1951 | 459 | 2382 | 2.30E-249 | gp:[GI:7769754] [LN:AF191317] [AC:AF191317] [[PN:secretory lipase 4] [GN:LIP4] [OR:*Candida albicans*] [DB:genpept-pln2] [EC:3.1.1.3] [DE:*Candida albicans* secretory lipase 4 (LIP4) gene, complete cds.] [NT:Lip4; LIP] [LE:375] [RE:1754] [DI:direct] |
| LIP5 | 33 | 243 | 1389 | 463 | 2408 | 4.00E-252 | pir:[LN:T18225] [AC:T18225] [PN:hypothetical protein] [CL:*Mycobacterium tuberculosis* hypothetical protein Rv1592c] [OR:*Candida albicans*] [DB:pir2] >gp:[GI:3850152] [LN:CAC35A5] [AC:AL033396] [PN:hypothetical protein] [GN:Ca35A5.09] [OR:*Candida albicans*] [DB:genpept-pln4] [DE:*C. albicans* cosmid Ca35A5.] [NT:Ca35A5.09c, unknown, len:463 aa, similar to O06598] [LE:37185] [RE:38576] [DI:complement] |
| LIP6 | 34 | 244 | 1816 | 463 | 2419 | 2.70E-253 | gp:[GI:8809743] [LN:AF191319] [AC:AF191319] [PN:secretory lipase 6] [GN:Lip6] [OR:*Candida albicans*] [DB:genpept-pln2] 8 EC:3.1.3.3] [DE:*Candida albicans* secretory lipase 6 (Lip6) gene, complete cds.] [NT:LIP] [LE:266] [RE:1657] [DI:direct] |
| LIP7 | 35 | 245 | 1787 | 426 | 2238 | 4.50E-234 | gp:[GI:8809745] [LN:AF191320] [AC:AF191320] [PN:secretory lipase 7] [GN:Lip7] [OR:*Candida albicans*] [DB:genpept-pln2] [EC:3.1.1.3] [DE:*Candida albicans* secretory lipase 7 (Lip7) gene, complete cds.] [NT:LIP; belongs to lipase gene family; signal peptide] [LE:295] [RE:1575] [DI:direct] |
| LIP8 | 36 | 246 | 2000 | 460 | 2385 | 1.10E-249 | gp:[GI:7769758] [LN:AF191321] [AC:AF191321] [PN:secretory lipase 8] [GN:LIP8] [OR:*Candida albicans*] [DB:genpept-pln2] [EC:3.1.1.3] [DE:*Candida albicans* secretory lipase 8 (LIP8) gene, complete cds.] [NT:Lip8; LIP] [LE:366] [RE:1748] [DI:direct] |
| LIP9 | 37 | 247 | 1829 | 453 | 2347 | 1.20E-245 | gp:[GI:8809747] [LN:AF191322] [AC:AF191322] [PN:secretory lipase 9] [GN:Lip9] [OR:*Candida albicans*] [DB:genpept-pln2] [EC:3.1.1.3] [DE:*Candida albicans* secretory lipase 9 (Lip9) gene, complete cds.] [NT:LIP] [LE:288] [RE:1649] [DI:direct] |

-continued

| ORF | NT Seq ID | AA Seq ID | NT ORF Length | AA ORF Length | Score | Probability | Description |
|---|---|---|---|---|---|---|---|
| MP65 | 38 | 248 | 1415 | 379 | 1939 | 2.40E-202 | gp:[GI:12057031] [LN:CAL010064] [AC:AJ010064] [PN:mannoprotein MP65] [GN:mp65] [OR:*Candida albicans*] [DB:genpept-pln4] [DE:*Candida albicans* mRNA for MP65 mannoprotein.] [LE:90] [RE:1229] [DI:direct] |
| PHR1 | 39 | 249 | 2026 | 548 | 2836 | 1.50E-297 | sp:[LN:PHR1_CANAL] [AC:P43076] [GN:PHR1] [OR:*Candida albicans*] [SR:,Yeast] [DE:PH responsive protein 1 precursor (PH-regulated protein 1)] [SP:P43076] [DB:swissprot] >gp:[GI:857672] [LN:YSAPHR1A] [AC:M90812] [PN:pH responsive protein] [GN:PHR1] [OR:*Candida albicans*] [SR:*Candida albicans* (strain SC5314) DNA] [DB:genpept-pln5] [DE:*Candida albicans* pH responsive protein (PHR1) gene, complete cds.] [NT:shows 56% identity to GPI-anchored gp115 from S.] [LE:262] [RE:1908] [DI:direct] |
| PHR2 | 40 | 250 | 1942 | 546 | 2827 | 1.30E-296 | sp:[LN:PHR2_CANAL] [AC:O13318] [GN:PHR2] [OR:*Candida albicans*] [SR:,Yeast] [DE:PH responsive protein 2 precursor (PH-regulatd protein 2)] [SP:O13318] [DB:swissprot] >gp:[GI:2293530] [LN:AF011386] [AC:AF011386] [PN:pH-regulated protein 2] [GN:PHR2] [OR:*Candida albicans*] [DB:genpept-pln1] [DE:*Candida albicans* pH-regulated protein 2 (PHR2) gene, complete cds.] [LE:52] [RE:1692] [DI:direct] |
| PHR3 | 41 | 251 | 1764 | 487 | 2591 | 1.50E-271 | gp:[GI:6911253] [LN:AF221545] [AC:AF221545] [PN:PHR3p] [OR:*Candida albicans*] [DB:genpept-pln2] [DE:*Candida albicans* PHR3p gene, complete cds.] [NT:similar to PHR1 and PHR2 of *Candida albicans*] [LE:51:215] [RE:161:1567] [DI:directJoin] |
| PLB97 | 42 | 252 | 38874 | 754 | 3928 | 0 | pir:[LN:T18238] [AC:T18238] [PN:lysophospholipase,] [OR:*Candida albicans*] [EC:3.1.1.5] [DB:pir2] >gp:[GI:3859722] [LN:CAC41C10] [AC:AL033501] [PN:lysophospholipase] [GN:Ca41c10.12] [OR:*Candida albicans*] [DB:genpept-pln4] [DE:*C. albicans* cosmid Ca41C10.] [NT:Ca41C10.12, phospholipase, len: 754 aa, similar to] [LE:34742] [RE:37006] [DI:direct] |
| PLB98 | 43 | 253 | 2326 | 608 | 3190 | 0 | gp:[GI:4062848] [LN:AB010809] [AC:AB010809] [PN:phospholipase B] [OR:*Candida albicans*] [SR:*Candida albicans* DNA] [DB:genpept-pln1] [DE:*Candida albicans* gene for phospholipase B, complete cds.] [LE:127] [RE:1953] [DI:direct] |
| PLB99 | 44 | 254 | 2847 | 605 | 3193 | 0 | gp:[GI:3228524] [LN:AF045558] [AC:AF045558] [PN:phospholipase B] [GN:PLB] [FN:lysophospholipase] [OR:*Candida albicans*] [DB:genpept-pln1] [DE:*Candida albicans* phospholipase B (PLB) gene, complete cds.] [LE:339] [RE:2156] [DI:direct] |
| RBT1 | 45 | 255 | 3168 | 750 | 3789 | 0 | gp:[GI:9963982] [LN:AF254142] [AC:AF254142] [PN:repressed by TUP1 protein 1] [GN:RBT1] [OR:*Candida albicans*] [DB:genpept-pln2] [DE:*Candida albicans* repressed by TUP1 protein 1 (RBT1) gene, complete cds.] [NT:cell wall protein; GPI modified; predicted] [LE:617] [RE:2869] [DI:direct] |
| SAP1 | 46 | 256 | 1480 | 391 | 1995 | 2.70E-208 | gp:[GI:578121] [LN:CASAP] [AC:X56867] [PN:microbial aspartic proteinases] [OR:*Candida albicans*] [DB:genpept-pln4] [EC:3.4.23.6] [DE:*C. albicans* gene for secretory aspartate proteinase.] [SP:P28872] [LE:129] [RE:1304] [DI:direct] |
| SAP10 | 47 | 257 | 1715 | 441 | 2288 | 2.20E-239 | gp:[GI:7673038] [LN:AF146440] [AC:AF146440] [PN:secretory aspartyl proteinase] [GN:SAP10] [OR:*Candida albicans*] [DB:genpept-pln2] [DE:*Candida albicans* secretory aspartyl proteinase (SAP10) gene, complete cds.] [NT:secreted aspartyl protease; secreted acid] [LE:130] [RE:1455] [DI:direct] |
| SAP2 | 48 | 258 | 1341 | 398 | 2020 | 6.00E-211 | sp:[LN:CAR2_CANAL] [AC:P28871:P43097] [GN:SAP2:PRA11:PRA2] [OR:*Candida albicans*] [SR:,Yeast] [EC:3.4.23.24] [DE:(ACP2) (Secreted aspartic protease 2)] [SP:P28871:P43097] [DB:swissprot] >pir:[LN:A45280] [AC:A45280:A60342] [PN:candidapepsin, 2 precursor [validated]:*Candida albicans* aspartic proteinase:secretory acid proteinase 2 (SAP2)] [GN:PRA11] [CL:pepsin] [OR:*Candida albicans*] [EC:3.4.23.24] [DB:pir2] gp:[GI:170841] [LN:YSACPA] [AC:M83663] [PN:aspartyl proteinase] [GN:PrA2] [OR:*Candida albicans*] [SR:*Candida albicans* (library: lambda-EMBL4; ATCC 10261) DNA] [DB:genpept-pln5] [DE:*Candida albicans* secreted aspartyl proteinase gene, complete cds.] [NT:pre-pro peptide] [LE:126] [RE:1322] [DI:direct] |
| SAP3 | 49 | 259 | 1556 | 398 | 2041 | 3.60E-213 | sp:[LN:CAR3_CANAL] [AC:P43092] [GN:SAP3] [OR:*Candida albicans*] [SR:,Yeast] [EC:3.4.23.24] [DE:(ACP3) (Secreted aspartic protease 3)] [SP:P43092] [DB:swissprot] >pir:[LN:A36926] [AC:A36926] [PN:aspartyl proteinase SAP3, precursor] [GN:SAP3] [CL:pepsin] [OR:*Candida albicans*] [EC:3.4.23.—] [DB:pir2] >gp:[GI:408091] [LN:YSASAP3] [AC:L22358] [PN:secreted aspartyl proteinase 3] [GN:SAP3] [OR:*Candida albicans*] [SR:*Candida albicans* (strain) DNA] [DB:genpept-pln5] [DE:*Candida albicans* secreted aspartyl proteinase (SAP3) gene, complete cds.] [LE:230] [RE:1426] [DI:direct] |
| SAP4 | 50 | 260 | 1618 | 417 | 2138 | 1.80E-223 | sp:[LN:CAR4_CANAL] [AC:P43093] [GN:SAP4] [OR:*Candida albicans*] [SR:,Yeast] [EC:3.4.23.24] [DE:(ACP4) (Secreted aspartic protease 4)] [SP:P43093] [DB:swissprot] >pir:[LN:A55524] [AC:A55524] [PN:aspartic proteinase, secreted] [GN:SAP4] [CL:pepsin] [OR:*Candida albicans*] [EC:3.4.—.—] [DB:pir2] >gp:[GI:466346] [LN:YSASAP4] [AC:L25388] [PN:secreted aspartyl proteinase 4] [GN:SAP4] [OR:*Candida albicans*] [SR:*Candida albicans* (strain WO1) DNA] [DB:genpept-pln5] [DE:*Candida albicans* secreted aspartyl proteinase (SAP4) gene, complete cds.] [LE:138] RE:1391] [DI:direct] |

-continued

| ORF | NT Seq ID | AA Seq ID | NT ORF Length | AA ORF Length | Score | Probability | Description |
|---|---|---|---|---|---|---|---|
| SAP5 | 51 | 261 | 1611 | 418 | 2144 | 4.10E-224 | sp:[LN:CAR5_CANAL] [AC:P43094] [GN:SAP5] [OR:*Candida albicans*] [SR:,Yeast] [EC:3.4.23.24] [DE:(ACP5) (Secreted aspartic protease 5)] [SP:P43094] [DB:swissprot] >pir:[LN:S42072] [AC:S49056:S42072] [PN:aspartic proteinase, SAP5] [CL:pepsin] [OR:*Candida albicans*] [EC:3.4.23.—] [DB:pir2] >gp:[GI:456249] [LN:CASAP4G] [AC:Z30191] [PN:aspartyl protease] [OR:*Candida albicans*] [DB:genpept-pln4] [DE:*Candida albicans* Ca74 of SAP5 gene encoding aspartyl protease.] [SP:P43094] [LE:268] [RE:1524] [DI:direct] |
| SAP6 | 52 | 262 | 1846 | 418 | 2147 | 2.00E-224 | sp:[LN:CAR6_CANAL] [AC:P43095] [GN:SAP6] [OR:*Candida albicans*] [SR:,Yeast] [EC:3.4.23.24] [DE:(ACP6) (Secreted aspartic protease 6)] [SP:P43095] [DB:swissprot] >pir:[LN:S42073] [AC:S49057:S42073] [PN:aspartic proteinase, SAP6] [CL:pepsin] [OR:*Candida albicans*] [EC:3.4.23.—] [DB:pir2] >gp:[GI:456252] [LN:CASAP5G] [AC:Z30192] [PN:aspartyl protease] [GN:SAP6] [OR:*Candida albicans*] [DB:genpept-pln4] [DE:*C. albicans* (Ca74) SAP6 gene for aspartyl protease.] [SP:P43095] [LE:224] [RE:1480] [DI:direct] |
| SAP7 | 53 | 263 | 2317 | 588 | 3041 | 0 | sp:[LN:CAR7_CANAL] [AC:P43096] [GN:SAP7] [OR:*Candida albicans*] [SR:,Yeast] [EC:3.4.23.24] [DE:(ACP7) (Secreted aspartic protease 7)] [SP:P43096] [DB:swissprot] >gp:[GI:578123] [LN:CASAP6G] [AC:Z30193] [PN:aspartyl protease] [GN:SAP7] [OR:*Candida albicans*] [DB:genpept-pln4] [DE:*C. albicans* (Ca74) SAP7 gene for aspartyl protease.] [SP:P43096] [LE:283] [RE:2049] [DI:direct] |
| SAP8 | 54 | 264 | 1641 | 405 | 2041 | 3.50E-213 | sp:[LN:CAR8_CANAL] [AC:O42778] [GN:SAP8] [OR:*Candida albicans*] [SR:,Yeast] [EC:3.4.23.24] [DE:(ACP8) (Secreted aspartic protease 8)] [SP:O42778] [DB:swissprot] >gp:[GI:2811288] [LN:AF043330] [AC:AF043330] [PN:secreted aspartyl proteinase] [GN:SAP8] [OR:*Candida albicans*] [DB:genpept-pln1] [DE:*Candida albicans* secreted aspartyl proteinase (SAP8) gene, complete cds.] [NT:Sap8p] [LE:250] [RE:1467] [DI:direct] |
| SAP9 | 55 | 265 | 2117 | 544 | 2740 | 2.20E-287 | sp:[LN:CAR9_CANAL] [AC:O42779] [GN:SAP9] [OR:*Candida albicans*] [SR:,Yeast] [EC:3.4.23.24] [DE:(ACP9) (Secreted aspartic protease 9)] [SP:O42779] [DB:swissprot] >gp:[GI:2811290] [LN:AF043331] [AC:AF043331] [PN:secreted aspartyl proteinase] [GN:SAP9] [OR:*Candida albicans*] [DB:genpept-pln1] [DE:*Candida albicans* secreted aspartyl proteinase (SAP9) gene, complete cds.] [NT:Sap9p] [LE:255] [RE:1889] [DI:direct] |
| WAP1 | 56 | 266 | 4792 | 1018 | 5108 | 0 | gp:[GI:9963992] [LN:AF254147] [AC:AF254147] [PN:putative cell wall protein] [GN:WAP1] [OR:*Candida albicans*] [DB:genpept-pln2] [DE:*Candida albicans* putative cell wall protein (WAP1) gene, complete cds.] [NT:contains predicted signal sequence and GPI addition] [LE:1175] [RE:4231] [DI:direct] |
| XOG1 | 57 | 267 | 39568 | 438 | 2425 | 6.60E-254 | sp:[LN:EXG_CANAL] [AC:P29717] [GN:XOG1:XOG] [OR:*Candida albicans*] [SR:,Yeast] [EC:3.2.1.58] [DE:glucanase)] [SP:P29717] [DB:swissprot] >gp:[GI:578126] [LN:CAXOG] [AC:X56556:S55517] [PN:glucan 1,3-beta-glucosidase] [GN:XOG] [OR:*Candida albicans*] [DB:genpept-pln4] [EC:3.2.1.58] [DE:*C. albicans* XOG gene for exo-1,3-beta-glucanase.] [SP:P29717] [LE:227] [RE:1543] [DI:direct] |
| [AI:7500742175] | 58 | 268 | 1263 | 420 | 1250 | 2.20E-129 | gp:[GI:944922] [LN:CWU31091] [AC:U31091] [PN:beta-glucosidase] [GN:bgIA] [OR:*Candida wickerhamii*] [DB:genpept-pln4] [EC:3.2.1.21] [DE:*Candida wickerhamii* putative beta-glucosidase (bglA) gene, complete cds.] [NT:putative] [LE:27] [RE:1289] [DI:direct] |
| [AI:7500742368] | 59 | 269 | 1392 | 463 | 2279 | 1.50E-238 | sp:[LN:CHI2_CANAL] [AC:P40953] [GN:CHT2] [OR:*Candida albicans*] [SR:,Yeast] [EC:3.2.1.14] [DE:Chitinase 2 precursor,] [SP:P40953] [DB:swissprot] >gp:[GI:571427] [LN:CAU15800] [AC:U15800] [PN:chitinase] [GN:cht2] [OR:*Candida albicans*] [DB:genpept-pln4] [DE:*Candida albicans* chitinase (cht2) gene, complete cds.] [LE:201] [RE:1952] [DI:direct] |
| [AI:7500743848] | 60 | 270 | 1008 | 335 | 202 | 1.30E-15 | sp:[LN:QUTA_EMENI] [AC:P10563] [GN:QUTA] [OR:*Emericella nidulans*] [SR:,*Aspergillus nidulans*] [DE:Quinic acid utilization activator] [SP:P10563] [DB:swissprot] >pir:[LN:A26983] [AC:A26983] [PN:regulatory protein QUTA] [GN:QUTA] [CL:unassigned GAL4-type zinc cluster protein:GAL4 zinc binuclear cluster homology] [OR:*Emericella nidulans:Aspergillus nidulans*] [DB:pir2] >gp:[GI:2397] [LN:ANQUTA] [AC:X06252] [OR:*Emericella nidulans*] [DB:genpept-pln2] [DE:*Aspergillus nidulans* regulatory gene QUTA for quinic acidutilization.] [NT:QUTA protein (AA 1-825)] [SP:P10563] [LE:298] (RE:2775] [DI:direct] |
| [AI:7500744875] | 61 | 271 | 1356 | 452 | 2065 | 4.00E-216 | gp:[GI:9963992] [LN:AF254147] [AC:AF254147] [PN:putative cell wall protein] [GN:WAP1] [OR:*Candida albicans*] [DB:genpept-pln2] [DE:*Candida albicans* putative cell wall protein (WAP1) gene, complete cds.] [NT:contains predicted signal sequence and GPI addition] [LE:1175] [RE:4231] [DI:direct] |
| [AI:7500746723] | 62 | 272 | 2148 | 715 | 3338 | 0 | gp:[GI:3859666] [LN:CAC38F10] [AC:AL033502] [PN:kinesin-like protein] [GN:Ca38F10.07] [OR:*Candida albicans*] [DB:genpept-pln4] [DE:*C. albicans* cosmid Ca38F10.] [NT:Ca38F10.07, kinesin-like protein, len: 665, similar] [LE:25257] [RE:27254] [DI:direct] |

-continued

| ORF | NT Seq ID | AA Seq ID | NT ORF Length | AA ORF Length | Score | Probability | Description |
|---|---|---|---|---|---|---|---|
| [AI:7500748 186] | 63 | 273 | 1692 | 563 | 1012 | 2.00E-130 | sp:[LN:NPR1_YEAST] [AC:P22211] [GN:NPR1:YNL183C:N1631] [OR:*Saccharomyces cerevisiae*] [SR:,Baker's yeast] [EC:2.7.1.—] [DE:Nitrogen permease reactivator protein,] [SP:P22211] [DB:swissprot] >pir:[LN:S63138] [AC:S63138:S11183] [PN:probable protein kinase NPR1,:nitrogen permease reactivator 1:protein N1631:protein YNL183c] [GN:NPR1] [CL:unassigned Ser/Thr or Tyr-specific protein kinases:protein kinase homology] [OR:*Saccharomyces cerevisiae*] [EC:2.7.1.—] [DB:pir2] [MP:14L] >gp:[GI:1302168] [LN:SCYNL183C] [AC:Z71459:Y13139] [GN:NPR1] [OR:*Saccharomyces cerevisiae*] [SR:baker's yeast] [DB:genpept-pln5] [DE:*S. cerevisiae* chromosome XIV reading frame ORF YNL183c.] [NT:ORF YNL183c] [SP:P22211] [LE:254] [RE:2626] [DI:complement] |
| [AI:7500749 610] | 64 | 274 | 3573 | 1191 | 4871 | 0 | gp:[GI:10952736] [LN:AF272027] [AC:AF272027] [PN:agglutinin-like protein] [OR:*Candida albicans*] [DB:genpept-pln2] [DE:*Candida albicans* agglutinin-like protein mRNA, partial cds.] [LE:1] [RE:>4569] [DI:direct] |
| [AI:7500758 296] | 65 | 275 | 1044 | 347 | 166 | 1.10E-13 | sp:[LN:CIS3_YEAST] [AC:P47001] [GN:CIS3:CCW11:YJL158C:J0561] [OR:*Saccharomyces cerevisiae*] [SR:,Baker's yeast] [DE:Covalently-linked cell wall protein 11 precursor (CIS3 protein)] [SP:P47001] [DB:swissprot] >pir:[LN:S56941] [AC:S56941] [PN:heat shock protein PIR2 homolog YJL158c:protein J0561] [GN:CIS3] [OR:*Saccharomyces cerevisiae*] [DB:pir2] [MP:10L] >gp:[GI:1015581] [LN:SCYJL158C] [AC:Z49433:Y13136] [OR:*Saccharomyces cerevisiae*] [SR:baker's yeast] [DB:genpept-pln5] [DE:*S. cerevisiae* chromosome X reading frame ORF YJL158c.] [NT:ORF YJL158c] [SP:P47001] [LE:586] [RE:1269] [DI:complement] |
| [AI:7500758 378] | 66 | 276 | 2142 | 713 | 1111 | 7.80E-115 | sp:[LN:PLB1_TORDE] [AC:Q11121] [OR:*Torulaspora delbrueckii*] [SR:,Yeast:*Saccharomyces rosei*] [EC:3.1.1.5] [DE:Lysophospholipase precursor, (Phospholipase B)] [SP:Q11121] [DB:swissprot] >gp:[GI:1020416] [LN:YSCBGENE] [AC:D32134] [PN:phospholipase B] [OR:*Torulaspora delbrueckii*] [SR:*Saccharomyces rosei* (strain YL-32) (library: Charomid 9-36) DNA] [DB:genpept-pln5] [DE:*Saccharomyces rosei* gene for phospholipase B, complete cds.] [LE:388] [RE:2337] [DI:direct] |
| [AI:7500760 864] | 67 | 277 | 951 | 316 | 307 | 1.20E-28 | pir:[LN:T22696] [AC:T22696] [PN:hypothetical protein F55B11.3] [GN:F55B11.3] [OR:*Caenorhabditis elegans*] [DB:pir2] [MP:4] >gp:[GI:3877698] [LN:CEF55B11] [AC:Z83318] [GN:F55B11.3 [OR:*Caenorhabditis elegans*] [DB:genpept-inv4] [DE:*Caenorhabditis elegans* cosmid F55B11, complete sequence.] [NT:predicted using Genefinder] [LE:24426:24649:24927:26086] [RE:24572:24870:25233:26255] [DI:directJoin] |
| [AI:7500763 321] | 68 | 278 | 2082 | 693 | 192 | 3.60E-13 | pir:[LN:T18501] [AC:T18501] [PN:hypothetical protein C0760c] [OR:*Plasmodium falciparum*] [DB:pir2] [MP:3] >gp:[GI:3758855] [LN:PFMAL3P6] [AC:Z98551:AL010161:AL010170:A:010212:AL010213:AL022222:AL139179: Z98553] [PN:hypothetical protein, PFC0760c] [GN:MAL3P6.11] [OR:*Plasmodium falciparum*] [SR:malaria parasite *P. falciparum*] [DB:genpept-inv4] [DE:*Plasmodium falciparum* MAL3P6, complete sequence.] [NT:PFC0760c, (MAL3P6.11), hypothetical protein, len:] [LE:53772] [RE:63956] [DI:complement] |
| AI:7500764 518] | 69 | 279 | 1932 | 643 | 1351 | 3.10E-140 | sp:[LN:SAT4_YEAST] [AC:P25333] [GN:SAT4:YCR008W:YCR8W:YCR101:YCR046] [OR:*Saccharomyces cerevisiae*] [SR:,Baker's yeast] [EC:2.7.1.—] [DE:Serine/threonine-protein kinase SAT4,] [SP:P25333] [DB:swissprot] >pir:[LN:OKBY8W] [AC:S17470:S19505:S26737:S19768:S20183] [PN:probable protein kinase YCR008w,:protein YCR046:protein YCR101] [GN:SAT4:YCR008w] [CL:probable protein kinase YCR008W:protein kinase homology] [OR:*Saccharomyces cerevisiae*] [EC:2.7.1.—] [DB:pir1] 8 MP:3R] >gp:[GI:242395] [LN:S76380] [AC:S76380] [GN:YCR101] [OR:*Saccharomyces cerevisiae*] [SR:baker's yeast] [DB:genpept-pln4] [DE:YCR101 = putative protein kinase [*Saccharomyces cerevisiae*, Genomic, 2580 nt].] [NT:putative protein kinase; This sequence comes from] [LE:481] [RE:2292] [DI:direct] >gp:[GI:1907151] [LN:SCCHRIII] [AC:X59720:S43845:S49180:S58084:S93798] 8 PN:hypothetical protein] [GN:SAT4] [OR:*Saccharomyces cerevisiae*] [SR:baker's yeast] [DB:genpept-pln4] [DE:*S. cerevisiae* chromosome III complete DNA sequence.] [NT:ORF YCR008w - similarity to serine/threonine-] [SP:P25333] [LE:128464] [RE:130275] [DI:direct] |
| [AI:7500766 693] | 70 | 280 | 1743 | 580 | 195 | 3.90E-14 | pir:[LN:T45463] [AC:T45463] [PN:membrane glycoprotein [imported]] [CL:*equine herpesvirus* glycoprotein X:*equine herpesvirus* 1 glycoprotein homology] [OR:*equine herpesvirus* 1] [DB:pir2] >gp:[GI:2114323] [LN:D88734] [AC:D88734] [PN:membrane glycoprotein] [GN:ORF71] [OR:*Equine herpesvirus* 1] [SR:*Equine herpesvirus* 1 (strain:BK343, isolate:3F clone) DNA] [DB:genpept-vrl2] [DE:*Equine herpesvirus* 1 DNA for membrane glycoprotein, complete cds.] [LE:118] [RE:2721] [DI:direct] |

-continued

| ORF | NT Seq ID | AA Seq ID | NT ORF Length | AA ORF Length | Score | Probability | Description |
|---|---|---|---|---|---|---|---|
| [AL7500767 653] | 71 | 281 | 786 | 261 | 227 | 3.70E-20 | sp:[LN:HWP1_CANAL] [AC:P46593:P87019:O13424] [GN:HQP1:ECE2] [OR:*Candida albicans*] [SR:,Yeast] [DE:Hyphal wall protein 1 (Cell elongation protein 2)] [SP:P46593:P87019:O13424] [DB:swissprot] >gp:[GI:1915979] [LN:CAU64206] [AC:U64206] [PN:hyphal wall protein 1] [GN:HWP1] [OR:*Candida albicans*] [DB:genpept-pln4] [DE:*Candida albicans* hyphal wall protein 1 (HWP1) gene, complete cds.] [NT:hyphal surface protein] [LE:503] [RE:2407] [DI:direct] |
| [AI:7500768 951] | 72 | 282 | 1473 | 490 | 392 | 1.80E-38 | pir:[LN:T45525] [AC:T45525] [PN:WSC4 homolog [imported]] [GN:wsc4] [OR:*Kluyveromyces marxianus* var. *lactis*:*Candida sphaerica*] [DB:pir2] >gp:[GI:5531272] [LN:KLA243803] [AC:AJ243800] [PN:WSC4 homologue] [GN:wsc4] [OR:*Kluyveromyces lactis*] [DB:genpept-pln4] [DE:*Kluyveromyces lactis* rim101 (partial), wsc4, ubi4 and ecm29 (partial) genes.] [LE:2272] [RE:3612] [DI:complement] |
| [AI:7500770 709] | 73 | 283 | 3180 | 1059 | 356 | 1.90E-37 | sp:[LN:YK70_YEAST] [AC:P36166] [GN:YKR090W] [OR:*Saccharomyces cerevisiae*] [SR:,Baker's yeast] [DE:Hypothetical 79.4 kDa protein in PRP16-SRP40 intergenic region] [SP:P36166] [DB:swissprot] >gp:GI:486577] [LN:SCYKR090W] [AC:Z28315:Y13137] [OR:*Saccharomyces cerevisiae*] [SR:baker's yeast] [DB:genpept-pln5] [DE:*S. cerevisiae* chromosome XI reading frame ORF YKR090w.] [NT:ORF YKR090w] [SP:P36166] [LE:581] [RE:2701] [DI:direct] |
| [AI:7500771 688] | 74 | 284 | 2277 | 758 | 126 | 1.60E-14 | pir:[LN:S66755] [AC:S66755:S66756] [PN:probable membrane protein YOL063c:hypothetical protein O1207] [CL:*Saccharomyces cerevisiae* probable membrane protein YOL063c] [OR:*Saccharomyces cerevisiae*] [DB:pir2] [MP:15L] >gp:[GI:1419881] [LN:SCYOL063C] [AC:Z74805:Y13140] [OR:*Saccharomyces cerevisiae*] [SR:baker's yeast] [DB:genpept-pln5] [DE:*S. cerevisiae* chromosome XV reading frame ORF YOL063c.] [NT:ORF YOL063c] [LE:216] [RE:3089] [DI:complement] |
| [AI:7500772 763] | 75 | 285 | 1479 | 492 | 441 | 6.20E-75 | sp:[LN:YHB0_YEAST] [AC:P38748] [GN:YHL010C] [OR:*Saccharomyces cerevisiae*] [SR:,Baker's yeast] [DE:Hypothetical 67.5 kDa protein in PRPS4-STE20 intergenic region] [SP:P38748] [DB:swissprot] >pir:[LN:S46825] [AC:S46825] [PN:hypothetical protein YHL010c] [GN:YHL010c] [CL:RING finger homology] [OR:*Saccharomyces cerevisiae*] [DB:pir2] 8 MP:8L] |
| orf6.1030 | 76 | 286 | 2139 | 713 | 479 | 7.50E-45 | gp:[GI:13810411] [LN:SPAPJ4664] [AC:AL590884] [PN:hypothetical protein; sequence orphan; low] [OR:*Schizosaccharomyces pombe*] [SR:fission yeast] [DB:genpept-pln5] [DE:*S. pombe* chromosome I cosmid c4664.] [LE:2430] [RE:14345] [DI:direct] >gp:[GI:14018379] [LN:SPBPJ4664] [AC:AL591302] [PN:hypothetical protein; sequence orphan; low] [GN:SPBPJ4664.02] [OR:*Schizosaccharomyces pombe*] [SR:fission yeast] [DB:genpept-pln5] [DE:*S. pombe* chromosome II cosmid c4664.] [LE:2430] [RE:14345] [DI:direct] |
| orf6.1059 | 77 | 287 | 1074 | 358 | 417 | 1.00E-40 | sp:[LN:PLB2_YEAST] [AC:Q03674] [GN:PLB2:YMR006C:YM8270.08C] [OR:*Saccharomyces cerevisiae*] [SR:,Baker's yeast] [EC:3.1.1.5] [DE:Lysophospholipase 2 precursor, (Phospholipase B2)] [SP:Q03674] [DB:swissprot] >pir:[LN:S53035] [AC:S53035] [PN:probable membrane protein YML006c:hypothetical protein YM8270.08c] [GN:YML006c] [CL:yeast lysophospholipase] [OR:*Saccharomyces cerevisiae*] [DB:pir2] [MP:13R] >gp:[GI:4732121] [LN:AF129165] [AC:AF129165] [PN:phospholipase B/lysophospholipase precursor] [GN:PLB2] [OR:*Saccharomyces cerevisiae*] [SR:baker's yeast] [DB:genpept-pln2] [DE:*Saccharomyces cerevisiae* phospholipase B/lysophospholipase precursor (PLB2) gene, complete cds.] [LE:1] [RE:2121] [DI:direct] >gp:[GI:728653] [LN:SC8270] [AC:Z48613:Z71257] [PN:unknown] [OR:*Saccharomyces cerevisiae*] [SR:baker's yeast] [DB:genpept-pln4] [DE:*S. cerevisiae* chromosome XIII cosmid 8270.] [NT:YM8270.08c, putative lysophosholipase, similar to] [SP:Q03674] [LE:12275] [RE:14395] [DI:complement] |
| orf6.1114 | 78 | 288 | 2685 | 894 | 3342 | 0 | gp:[GI:10952736] [LN:AF272027] [AC:AF272027] [PN:agglutinin-like protein] [OR:*Candida albicans*] [DB:genpept-pln2] [DE:*Candida albicans* agglutinin-like protein mRNA, partial cds.] [LE:1] [RE:>4569] [DI:direct] |
| orf6.1115 | 79 | 289 | 1404 | 467 | 2283 | 2.60E-239 | sp:[LN:ALS1_CANAL] [AC:P46590] [GN:ALS1] [OR:*Candida albicans*] [SR:,Yeast] [DE:Agglutnin-like protein 1 precursor] [SP:P46590] [DB:swissprot] >gp:[GI:7687905] [LN:YSAALS1] [AC:L25902] [PN:agglutinin-like protein] [GN:ALS1] [OR:*Candida albicans*] [DB:genpept-pln5] [DE:*Candida albicans* agglutinin-like sequence (ALS1) gene, complete cds.] [LE:1] [RE:3783] [DI:direct] |
| orf6.1231 | 80 | 290 | 1362 | 453 | 1055 | 8.60E-109 | sp:[LN:YG46_YEAST] [AC:P53301] [GN:YGR189C:G7553] [OR:*Saccharomyces cerevisiae*] [SR:,Baker's yeast] [DE:Hypothetical 52.8 kDa protein in BUB1-HIP1 intergenic region] [SP:P53301] [DB:swissprot] >pir[LN:S64507] [AC:S64507] [PN:probable membrane protein YGR189c:hypothetical protein G7553] [GN:YGR189c] [OR:*Saccharomyces cerevisiae*] [DB:pir2] [MP:7R] >gp:[GI:1430955] [LN:SC23KB] [AC:X99074] [OR:*Saccharomyces cerevisiae*] [SR:baker's yeast] [DB:genpept-pln4] [DE:*S. cerevisiae* 23Kb DNA segment from right arm of chromosome VII.] [NT:G7553] [SP:P53301] [LE:20321] [RE:21844] [DI:complement] |

-continued

| ORF | NT Seq ID | AA Seq ID | NT ORF Length | AA ORF Length | Score | Probability | Description |
|---|---|---|---|---|---|---|---|
| orf6.1249 | 81 | 291 | 1773 | 590 | 386 | 3.20E-40 | >gp:[GI:1323336] [LN:SCYGR189C] [AC:Z72974:Y13135] [OR:*Saccharomyces cerevisiae*] [SR:baker's yeast] [DB:genpept-pln5] [DE:*S. cerevisiae* chromosome VII rading frame ORF YGR189c.] [NT:ORF YGR189c] [SP:P53301] [LE:1560] [RE:3083] [DI:complement] pir:[LN:JH0204] [AC:JH0204] [PN:hypothetical 30.5K protein precursor] [CL:probable pheromone-responsive protein] [OR:*Enterococcus faecalis*] [DB:pir2] >gp:[GI:3023044] [LN:AF007787] [AC:AF007787:X17092] [OR:*Enterococcus faecalis*] [DB:genpept-bct2] [DE:*Enterococcus faecalis* plasmid pAM-beta-1 copy number repressor (copF), RepE (repE), resolvase (res beta), and type Itopoisomerase (top beta) genes, complete cds and unknown genes.] [NT:orfC] [LE:933] [RE:1799] [DI:direct] |
| orf6.129 | 82 | 292 | 2064 | 687 | 295 | 8.70E-25 | gp:[GI:7228476] [LN:AF163151] [PN:dentin sialophosphoprotein precursor] [GN:DSPP] [OR:*Homo sapiens*] [SR:human] [DB:genpept-pri9] [DE:*Homo sapiens* dentin sialophosphoprotein precursor (DSPP) gene, complete cds.] [LE:4130:5320:5537:7000] [RE:4180:5403:6523:9639] [DI:directJoin] |
| orf6.1293 | 83 | 293 | 1359 | 452 | 1462 | 7.20E-152 | sp:[LN:YKE6_YEAST] [AC:P36091] [GN:YKL046C:YKL259] [OR:*Saccharomyces cerevisiae*] [SR:,Baker's yeast] [DE:Hypothetical 49.6 kDa protein in ELM1-PRI2 intergenic region] [SP:P36091] 8 DB:swissprot] >pir:[LN:S37867] [AC:S37867:S40654] [PN:hypothetical protein YKL046c precursor:hypothetical protein YKL259] [CL:*Schizosaccharomyces pombe* hypothetical protein SPCC970.02] [OR:*Saccharomyces cerevisiae*] [DB:pir2] [MP:11L] >gp:[GI:486062] [LN:SCYKL046C] [AC:Z28046:Y13137] [OR:*Saccharomyces cerevisiae*] [SR:baker's yeast] [DB:genpept-pln5] [DE:*S. cerevisiae* chromosome XI reading frame ORF YKL046c.] [NT:ORF YKL046c] [SP:P36091] [LE:262] [RE:1611] [DI:complement] |
| orf6.1310 | 84 | 294 | 3090 | 1029 | 5282 | 0 | gp:[GI:10952736] [LN:AF272027] [AC:AF272027] [PN:agglutinin-like protein] [OR:*Candida albicans*] [DB:genpept-pln2] [DE:*Candida albicans* agglutinin-like protein mRNA, partial cds.] [LE:1] [RE:>4569] [DI:direct] |
| orf6.1331 | 85 | 295 | 1305 | 434 | 374 | 6.20E-36 | gp:[GI:9963982] [LN:AF254142] [AC:AF254142] [PN:repressed by TUP1 protein 1] [GN:RBT1] [OR:*Candida albicans*] [DB:genpept-pln2] [DE:*Candida albicans* repressed by TUP1 protein 1 (RBT1) gene, complete cds.] [NT:cell wall protein; GPI modified; predicted] [LE:617] [RE:2869] [DI:direct] |
| orf6.1377 | 86 | 296 | 4761 | 1586 | 5318 | 0 | gp:[GI:10952736] [LN:AF272027] [AC:AF272027] [PN:agglutinin-like protein] [OR:*Candida albicans*] [DB:genpept-pln2] [DE:*Candida albicans* agglutinin-like protein mRNA, partial cds.] [LE:1] [RE:>4569] [DI:direct] |
| orf6.1488 | 87 | 297 | 1287 | 428 | 634 | 3.80E-64 | sp:[LN:YCE8_YEAST] [AC:P25380] [GN:YCL048W:YCL48W] [OR:*Saccharomyces cerevisiae*] [SR:,Baker'yeast] [DE:region] [SP:P25380] [DB:swissprot] >pir:[LN:S19377] [AC:S19377] [PN:probable membrane protein YCL048w] [GN:YCL048w] [OR:*Saccharomyces cerevisiae*] [DB:pir2] [MP:3L] >gp:[GI:5313] [LN:SCCHRIII] [AC:X59720:S43845:S49180:S58084:S93798] [PN:hypothetical protein] [OR:*Saccharomyces cerevisiae*] [SR:baker's yeast] [DB:genpept-pln4] [DE:*S. cerevisiae* chromosome III complete DNA sequence.] [NT:ORF YCL048w - strong similarity to sporulation-] [SP:P25380] [LE:42165] [RE:43556] [DI:direct] |
| orf6.1614 | 88 | 298 | 2658 | 886 | 4265 | 0 | sp:[LN:ALS3_CANAL] [AC:O74623] [GN:ALS3] [OR:*Candida albicans*] [SR:,Yeast] [DE:Agglutinin-like protein 3 precursor] [SP:O74623] [DB:swissprot] >gp[GI:3273415] [LN:CAU87956] [AC:U87956] [PN:agglutinin-like protein] [GN:ALS3] [OR:*Candida albicans*] [DB:genpept-pln4] [DE:*Candida albicans* agglutinin-like protein (ALS3) gene, complete cds.] [LE:1] [RE:3360] [DI:direct] |
| orf6.162 | 89 | 299 | 3366 | 1121 | 1410 | 1.60E-145 | gp:[GI:13810411] [LN:SPAPJ4664] [AC:AL590884] 8 PN:hypothetical protein; sequence orphan; low] [GN:SPBPJ4664.02] [OR:*Schizosaccharomyces pombe*] [SR:fission yeast] [DB:genpept-pln5] [DE:*S. pombe* chromosome I cosmid c4664.] [LE:2430] [RE:14345] [DI:direct] >gp:[GI:14018379] [LN:SPBPJ4664] [AC:AL591302] [PN:hypothetical protein; sequence orphan; low] [GN:SPBPJ4664.02] [OR:*Schizosaccharomyces pombe*] [SR:fission yeast] [DB:genpept-pln5] [DE:*S. pombe* chromosome II cosmid c4664.] [LE:2430] [RE:14345] [DI:direct] |
| orf6.1639 | 90 | 300 | 1413 | 470 | 1028 | 6.80E-106 | pir:[LN:S30839] [AC:S30839:S50504:S38545] [PN:UTR2 protein:protein YEL040w] [GN:UTR2] [OR:*Saccharomyces cerevisiae*] [DB:pir2] [MP:5L] >gp:[GI:603639] [LN:SCE8199] [AC:U18779:L10830:U00092] [PN:Utr2p] [GN:UTR2] [OR:*Saccharomyces cerevisiae*] [SR:baker's yeast] [DB:genpept-pln4] [DE:*Saccharomyces cerevisiae* chromosome V cosmid 8199, 8334, and 9871.] [NT:YEL040W; similar to CDS number 20 of cosmid 8167.] [LE:25027] [RE:26430] [DI:direct] |
| orf6.1732 | 91 | 301 | 4980 | 1659 | | | |
| orf6.1759 | 92 | 302 | 2298 | 765 | 344 | 5.90E-30 | gp:[GI:18447198] [LN:AY075323] [AC:AY075323] [PN:GH09355p] [GN:CG6004] [OR:*Drosophila melanogaster*] [SR:fruit fly] [DB:genpept-inv3] [DE:*Drosophila melanogaster* GH09355 full length cDNA.] [NT:Longest ORF] [LE:4] [RE:4548] [DI:direct] |

-continued

| ORF | NT Seq ID | AA Seq ID | NT ORF Length | AA ORF Length | Score | Probability | Description |
|---|---|---|---|---|---|---|---|
| orf6.1902 | 93 | 303 | 1092 | 363 | 297 | 2.30E-28 | sp:[LN:CAR8__CANAL] [AC:O42778] [GN:SAP8] [OR:*Candida albicans*] [SR:,Yeast] [EC:3.4.23.24] [DE:(ACP8) (Secreted aspartic protease 8)] [SP:O42778] [DB:swissprot] >gp:[GI:2811288] [LN:AF043330] [AC:AF043330] [PN:secreted aspartyl proteinase] [GN:SAP8] [OR:*Candida albicans*] [DB:genpept-pln1] [DE:*Candida albicans* secreted aspartyl proteinase (SAP8) gene, complete cds.] [NT:Sap8p] [LE:250] [RE:1467] [DI:direct] |
| orf6.1922 | 94 | 304 | 1797 | 598 | 386 | 1.70E-39 | pir:[LN:JH0204] [AC:JH0204] [PN:hypothetical 30.5K protein precursor] [CL:probable pheromone-responsive protein] [OR:*Enterococcus faecalis*] [DB:pir2] >gp:[GI:3023044] [LN:AF007787] [AC:AF007787:X17092] [OR:*Enterococcus faecalis*] [DB:genpept-bct2] [DE:*Enterococcus faecalis* plasmid pAM-beta-1 copy number repressor (copF), RepE (repE), resolvase (res beta), and type Itopoisomerase (top beta) genes, complete cds and unknown genes.] [NT:orfC] [LE:933] [RE:1799] [DI:direct] |
| orf6.1967 | 95 | 305 | 489 | 162 | 388 | 5.30E-38 | sp:[LN:YJR1__YEAST] [AC:P46992] [GN:YJL171C:J0512] [OR:*Saccharomyces cerevisiae*] [SR:,Baker's yeast] [DE:Hypothetical 43.0 kDa protein in CPS1-FPP1 intergenic region] [SP:P46992] [DB:swissprot] >pir[LN:S56954] [AC:S56954] [PN:protein YBR162c homolog YJL171c:probable membrane protein YJL171c:protein J0512] [GN:YJL171c] [OR:*Saccharomyces cerevisiae*] [DB:pir2] [MP:10L] >gp:[GI:1008365] [LN:SCYJL171C] [AC:Z49446:Y13136] [OR:*Saccharomyces cerevisiae*] [SR:baker's yeast] [DB:genpept-pln5] [DE:*S. cerevisiae* chromosome X reading frame ORF YJL171c.] [NT:ORF YJL171c] [SP:P46992] [LE:237] [RE:1427] [DI:complement] |
| orf6.1985 | 96 | 306 | 1830 | 609 | 3128 | 0 | gp:[GI:4062848] [LN:AB010809] [AC:AB010809] [PN:phospholipase B] [OR:*Candida albicans*] [SR:*Candida albicans* DNA] [DB:genpept-pln1] [DE:*Candida albicans* gene for phospholipase B, complete cds.] [LE:127] RE:1953] [DI:direct] |
| orf6.2030 | 97 | 307 | 1071 | 356 | 169 | 3.70E-12 | pir:[LN:S37788] [AC:S37788:S37993:S44565:S33652:C47165:S30797] [PN:PIR3 protein:protein p155:protein YKL163w:protein YKL163w:protein YKL617] [GN:PIR3] [OR:*Saccharomyces cerevisiae*] [DB:pir2] [MP:11L] >gp:[GI:407485] [LN:SCDCHR11] [AC:Z26877] [PN:unknown] [OR:*Saccharomyces cerevisiae*] [SR:baker's yeast] [DB:genpept-pln4] [DE:*S. cerevisiae* (S288C) 36.2kb DNA fragment from chromosome 11.] [SP:Q03180] [LE:8494] [RE:9471] [DI:direct] >gp:[GI:486285] [LN:SCYKL163W] [AC:Z28163:Y13137] [GN:PIR3] [OR:*Saccharomyces cerevisiae*] [SR:baker's yeast] [DB:genpept-pln5] [DE:*S. cerevisiae* chromosome XI reading frame ORF YKL163w.] [NT:ORF YKL163w] [SP:Q03180] [LE:1582] [RE:2559] [DI:direct] |
| orf6.2069 | 98 | 308 | 1179 | 392 | 2092 | 1.20E-218 | gp:[GI:6911253] [LN:AF221545] [AC:AF221545] [PN:PHR3p] [OR:*Candida albicans*] [DB:genpept-pln2] [DE:*Candida albicans* PHR3p gene, complete cds.] [NT:similar to PHR1 and PHR2 of *Candida albicans*] [LE:51:215] [RE:161:1567] [Di:directJoin] |
| orf6.2071 | 99 | 309 | 1257 | 418 | 1246 | 6.00E-129 | gp:[GI:944922] [LN:CWU31091] [AC:U31091] [PN:beta-glucosidase] [GN:bglA] [OR:*Candida wickerhamii*] [DB:genpept-pln4] [EC:3.2.1.21] [DE:*Candida wickerhamii* putative beta-glucosidase (bglA) gene, complete cds.] [NT:putative] [LE:27] [RE:1289] [DI:direct] |
| orf62101 | 100 | 310 | 1794 | 597 | 3229 | 0 | gp:[GI:3850137] [LN:CAC20C1] [AC:AL033391] [PN:conserved hypothetical protein] [GN:Ca20C1.17] [OR:*Candida albicans*] [DB:genpept-pln4] [DE:*C. albicans* cosmid Ca20C1.] [NT:Ca20C1.17, unknown, len: 597 aa, hydrophobic region] [LE:24641] [RE:26434] [DI:direct] |
| orf6.2204 | 101 | 311 | 1257 | 418 | 2111 | 1.30E-220 | sp:[LN:CAR6__CANAL] [AC:P43095] [GN:SAP6] [OR:*Candida albicans*] [SR:,Yeast] [EC:3.4.23.24] [DE:(ACP6) (Secreted aspartic protease 6)] [SP:P43095] [DB:swissprot] >pir:[LN:S42073] [AC:S49057:S42073] [PN:aspartic proteinase, SAP6] [CL:pepsin] [OR:*Candida albicans*] [EC:3.4.23.—] [DB:pir2] >gp:[GI:456252] [LN:CASAP5G] [AC:Z30192] [PN:aspartyl protease] [GN:SAP6] [OR:*Candida albicans*] [DB:genpept-pln4] [DE:*C. albicans* (Ca74) SAP6 gene for aspartyl protease.] [SP:P43095] [LE:224] [RE:1480] [DI:direct] |
| orf6.2332 | 102 | 312 | 3999 | 1332 | 2310 | 3.40E-242 | sp:[LN:RA50__YEAST] [AC:P12753] [GN:RAD50:YNL250W:N0872] [OR:*Saccharomyces cerevisiae*] [SR:,Baker's yeast] [DE:DNA repair protein RAD50 (153 kDa protein)] [SP:P12753] 8 DB:swissprot] >pir:[LN:BWBYDL] [AC:S05808:S63223]][PN:RAD50 protein:protein N0872:protein YNL250w] [GN:RAD50:YNL250w] [CL:RAD50 protein] [OR:*Saccharomyces cerevisiae*] [DB:pir1] [MP:14L] >gp:[GI:1255968] [LN:SCCHXIVL] [AC:X96722] [GN:RAD50] [OR:*Saccharomyces cerevisiae*] [SR:baker's yeast] [DB:genpept-pln4] [DE:*S. cerevisiae* DNA region from chromosome XIV, left arm.] [NT:ORF N0872] [SP:P12753] [LE:20533] [RE:24471] [DI:direct] >gp:[GI:4273] [LN:SCRAD50] 8 AC:X14814] [OR:*Saccharomyces cerevisiae*] [SR:baker's yeast] [DB:genpept-pln4] [DE:Yeast RAD50 gene for 153 kD protein.] [NT:153 kD protein (AA1-1312)] [SP:P12753] [LE:558] [RE:4496] |

-continued

| ORF | NT Seq ID | AA Seq ID | NT ORF Length | AA ORF Length | Score | Probability | Description |
|---|---|---|---|---|---|---|---|
| orf6.2346 | 103 | 313 | 975 | 324 | 847 | 8.80E-87 | [DI:direct] >gp:[GI:1302293] [LN:SCYNL250W] 8 AC:Z71526:Y13139] [GN:RAD50] [OR:*Saccharomyces cerevisiae*] [SR:baker's yeast] [DB:genpept-pln5] [DE:*S. cerevisiae* chromosome XIV reading frame ORF YNL250w.] [NT:ORF YNL250w] [SP:P12753] [LE:1095] [RE:5033] [DI:direct] sp:[LN:YGC8_YEAST] [AC:P53189] [GN:YGL028C] [OR:*Saccharomyces cerevisiae*] [SR:,Baker's yeast] [DE:precursor] [SP:P53189] [DB:swissprot] >pir:[LN:S64030] [AC:S64030] [PN:probable membrane protein YGL028c:hypothetical protein G3661] [GN:YGL028c] [OR:*Saccharomyces cerevisiae*] [DB:pir2] [MP:7L] >gp:[GI:1322500] [LN:SCYGL028C] [AC:Z72550:Y13135] [OR:*Saccharomyces cerevisiae*] [SR:baker's yeast] [DB:genpept-pln4] [DE:*S. cerevisiae* chromosome VII reading frame ORF YGL028c.] [NT:ORF YGL028c] [SP:P53189] [LE:856] [RE:2484] [DI:complement] |
| orf6.2395 | 104 | 314 | 1578 | 525 | 783 | 6.80E-80 | gp:[GI:4007667] [LN:PIA222862] [AC:AJ222862] [PN:exo-beta-1,3-glucanase] [GN:PAEXG2] [OR:*Pichia anomala*] [DB:genpept-pln4] [EC:3.2.1.58] [DE:*Pichia anomala* PAEXG2 gene, strain K.] [LE:313] [RE:1596] [DI:direct] |
| orf6.2398 | 105 | 315 | 1407 | 468 | 2423 | 1.00E-253 | gp:[GI:7012685] [LN:AF188894] [AC:AF188894] [PN:secretory lipase 1] [GN:LIP1] [OR:*Candida albicans*] [DB:genpept-pln2] [EC:3.1.1.3] [DE:*Candida albicans* secretory lipase 1 (LIP1) gene, complete cds.] [LE:366] [RE:1772] [DI:direct] |
| orf6.2415 | 106 | 316 | 306 | 101 | 112 | 3.00E-08 | gp:[GI:2565091] [LN:HSU80761] [AC:U80761] [PN:CTG26 alternate open reading frame] [GN:CTG26] [OR:*Homo sapiens*] [SR:human] [DB:genpept-pri17] [DE:*Homo sapiens* CTG26 alternate open reading frame mRNA, complete cds.] [NT:cysteine rich] [LE:>1] [RE:375] [DI:direct] |
| orf6.2643 | 107 | 317 | 1383 | 460 | 2327 | 1.50E-243 | gp:[GI:7769758] [LN:AF191321] [AC:AF191321] [PN:secretory lipase 8] [GN:LIP8] [OR:*Candida albicans*] [DB:genpept-pln2] [EC:3.1.1.3] [DE:*Candida albicans* secretory lipase 8 (LIP8) gene, complete cds.] [NT:Lip8; LIP] [LE:366] [RE:1748] [DI:direct] |
| orf6.2688 | 108 | 318 | 1218 | 405 | 2040 | 4.50E-213 | sp:[LN:CAR8_CANAL] [AC:O42778] [GN:SAP8] [OR:*Candida albicans*] [SR:,Yeast] [EC:3.4.23.24] [DE:(ACP8) (Secreted aspartic protease 8)] [SP:O42778] [DB:swissprot] >gp:[GI2811288] [LN:AF043330] [AC:AF043330] [PN:secreted aspartyl proteinase] [GN:SAP8] [OR:*Candida albicans*] [DB:genpept-pln1] [DE:*Candida albicans* secreted aspartyl proteinase (SAP8) gene, complete cds.] [NT:Sap8p] [LE:250] [RE:1467] [DI:direct] |
| orf6.288 | 109 | 319 | 1380 | 459 | 2368 | 6.90E-248 | gp:[GI:7769754] [LN:AF191317] [AC:AF191317] 8 PN:secretory lipase 4] [GN:LIP4] [OR:*Candida albicans*] [DB:genpept-pln2] [EC:3.1.1.3] [DE:*Candida albicans* secretory lipase 4 (LIP4) gene, complete cds.] [NT:Lip4; LIP] [LE:375] [RE:1754] [DI:direct] |
| orf6.2920 | 110 | 320 | 2859 | 952 | 3599 | 0 | gp:[GI:10952736] [LN:AF272027] [AC:AF272027] [PN:agglutinin-like protein] [OR:*Candida albicans*] [DB:genpept-pln2] [DE:*Candida albicans* agglutinin-like protein mRNA, partial cds.] [LE:1] [RE:>4569] [DI:direct] |
| orf6.2929 | 111 | 321 | 1104 | 367 | 1019 | 3.80E-105 | gp:[GI:9963982] [LN:AF254142] [AC:AF254142] [PN:repressed by TUP1 protein 1] [GN:RBT1] [OR:*Candida albicans*] [DB:genpept-pln2] [DE:*Candida albicans* repressed by TUP1 protein 1 (RBT1) gene, complete cds.] [NT:cell wall protein; GPI modified; predicted] [LE:617] [RE:2869] [DI:direct] |
| orf6.2978 | 112 | 322 | 1578 | 525 | 2357 | 8.40E-247 | pir:[LN:S49338] [AC:S49338] [PN:transcription factor] [OR:*Candida albicans*] [DB:pir2] |
| orf6.3000 | 113 | 323 | 5271 | 1756 | 5273 | 0 | gp:[GI:10952736] [LN:AF272027] [AC:AF272027] [PN:agglutinin-like protein] [OR:*Candida albicans*] [DB:genpept-pln2] [DE:*Candida albicans* agglutinin-like protein mRNA, partial cds.] [LE:1] [RE:>4569] [DI:direct] |
| orf6.3074 | 114 | 324 | 4782 | 1593 | 6043 | 0 | gp:[GI:10952736] [LN:AF272027] [AC:AF272027] [PN:agglutinin-like protein] [OR:*Candida albicans*] [DB:genpept-pln2] [DE:*Candida albicans* agglutinin-like protein mRNA, partial cds.] [LE:1] [RE:>4569] [DI:direct] |
| orf6.3097 | 115 | 325 | 927 | 308 | 1595 | 8.50E-166 | sp:[LN:BGL2_CANAL] [AC:P43070] [GN:BGL2] [OR:*Candida albicans*] [SR:,Yeast] [EC:3.2.1.58] [DE:glucanase)] [SP:P43070] [DB:swissprot] >gp:[GI:532776] [LN:CAU12975] [AC:U12975] [PN:beta-1,3 glucan transferase] [GN:BGL2] [OR:*Candida albicans*] [DB:genpept-pln4] [DE:*Candida albicans* ATCC 10261 beta-1,3 glucan transferase (BGL2) gene, complete cds.] [NT:secreted, cell wall] [LE:122] [ |
| orf6.3143 | 116 | 326 | 2814 | 937 | 4766 | 0 | sp:[LN:HYR1_CANAL] [AC:P46591] [GN:HYR1] [OR:*Candida albicans*] [SR:,Yeast] [DE:Hyphally regulated protein precursor] [SP:P46591] [DB:swissprot] >gp:[GI:1052565] [LN:CAHYR1GN] [AC:Z50123] [PN:hyphally regulated protein] [GN:HYR1] [FN:unknown] [OR:*Candida albicans*] [DB:genpept-pln4] [DE:*Candida albicans* HYR1 gene and promoter region.] [SP:P46591] [LE:1890] [RE:4703] [DI:direct] |
| orf6.3288 | 117 | 327 | 1602 | 533 | 332 | 1.80E-29 | gp:[GI:9963982] [LN:AF254142] [AC:AF254142] [PN:repressed by TUP1 protein 1] [GN:RBT1] [OR:*Candida albicans*] [DB:genpept-pln2] [DE:*Candida albicans* repressed by TUP1 protein 1 (RBT1) gene, complete cds.] [NT:cell wall protein; GPI modified; predicted] [LE:617] [RE:2869] [DI:direct] |
| orf6.3431 | 118 | 328 | 936 | 311 | 117 | 3.10E-06 | gp:[GI:17946377] [LN:AY071600] [AC:AY071600] [PN:RE65123p] [GN:CG7290] [OR:*Drosophila melanogaster*] [SR:fruit fly] [DB:genpept-inv3] [DE:*Drosophila melanogaster* RE65123 full length cDNA.] [NT:Longest ORF] [LE:43] [RE:1302] [DI:direct] |

-continued

| ORF | NT Seq ID | AA Seq ID | NT ORF Length | AA ORF Length | Score | Probability | Description |
|---|---|---|---|---|---|---|---|
| orf6.3499 | 119 | 329 | 3081 | 1026 | 5378 | 0 | pir:[LN:T18220] [AC:T18220] [PN:chitin synthase] [GN:Chs1] [CL:chitin synthase chsA] [OR:*Candida albicans*] [DB:pir2] >gp:[GI:3850147] [LN:CAC35A5] [AC:AL033396] [PN:chitin synthase] [GN:Chs1] [OR:*Candida albicans*] [DB:genpept-pln4] [DE:*C. albicans* cosmid Ca35A5.] [NT:Ca35A5.04, Chs1 gene, len: 1026 aa, CHS1_CANAL] [LE:20808] [RE:23888] [DI:direct] |
| orf6.3505 | 120 | 330 | 1515 | 504 | 668 | 8.80E-68 | sp:[LN:YG46_YEAST] [AC:P53301] [GN:YGR189C:G7553] [OR:*Saccharomyces cerevisiae*] [SR:Baker's yeast] [DE:Hypothetical 52.8 kDa protein in BUB1-HIP1 intergenic region] [SP:P53301] [DB:swissprot] >pir:[LN:S64507] [AC:S64507] [AC:S64507] [PN:probable membrane protein YGR189c:hypothetical protein G7553] [GN:YGR189c] [OR:*Saccharomyces cerevisiae*] [DB:pir2] [MP:7R] >gp:[GI:1430955] [LN:SC23KB] [AC:X99074] [OR:*Saccharomyces cerevisiae*] [SR:baker's yeast] [DB:genpept-pln4] [DE:*S. cerevisiae* 23Kb DNA segment from right arm of chromosome VII.] [NT:G7553] [SP:P53301] [LE:20321] [RE:21844] [DI:complement] >gp:[GI:1323336] [LN:SCYCGR189C] [AC:Z72974:Y13135] [OR:*Saccharomyces cerevisiae*] [SR:baker's yeast] [DB:genpept-pln5] [DE:*S. cerevisiae* chromosome VII reading frame ORF YGR189c.] [NT:ORF YGR189c] [SP:P53301] [LE:1560] [RE:3083] [DI:complement] |
| orf6.3558 | 121 | 331 | 2073 | 690 | 183 | 1.20E-12 | pir:[LN:T18501] [AC:T18501] [PN:hypothetical protein C0760c] [OR:*Plasmodium falciparum*] [DB:pir2] [MP:3] >gp:[GI3758855] [LN:PFMAL3P6] [AC:Z98551:AL010161:AL010170:AL010212:AL010213:AL022222:AL139179: Z98553] [PN:hypothetical protein, PFC0760c] [GN:MAL3P6.11] [OR:*Plasmodium falciparum*] [SR:malaria parasite *P. falciparum*] [DB:genpept-inv4] [DE:*Plasmodium falciparum* MAL3P6, complete sequence.] [NT: PFC0760c, (MAL3P6.11), hypothetical protein, len:] [LE:53772] [RE:63956] [DI:complement] |
| orf6.358 | 122 | 332 | 2550 | 849 | | | |
| orf6.3591 | 123 | 333 | 1554 | 517 | 403 | 4.40E-39 | gp:[GI:9963982] [LN:AF254142] [AC:AF254142] [PN:repressed by TUP1 protein 1] [GN:RBT1] [OR:*Candida albcians*] [DB:genpept-pln2] [DE:*Candida albicans* repressed by TUP1 protein 1 (RBT1) gene, complete cds.] [NT:cell wall protein; GPI modified; predicted] [LE:617] [RE:2869] [DI:direct] |
| orf6.3600 | 124 | 334 | 1275 | 424 | 353 | 2.20E-38 | sp:[LN:PIR3_YEAST] [AC:Q03180] [GN:PIR3:CCW8:YKL163W:YKL617] [OR:*Saccharomyces cerevisiae*] [SR:,Baker's yeast] [DE:PIR3 protein precursor (Covalently-linked cell wall protein 8)] [SP:Q03180] [DB:swissprot] >gp:[GI:404129] [LN:YSCPIR3P] [AC:D13742] [PN:Saccharomyces Pir3p] [GN:PIR3] [OR:*Saccharomyces cerevisiae*] [SR:*Saccharomyces cerevisiae* DNA] [DB:genpept-pln5] [DE:*S. cerevisiae* Pir3p gene.] [LE:241] [RE:1326] [DI:direct] |
| orf6.3624 | 125 | 335 | 1257 | 418 | 2096 | 5.10E-219 | sp:[LN:CAR6_CANAL] [AC:P43095] [GN:SAP6] [OR:*Candida albicans*] [SR:,Yeast] [EC:3.4.23.24] [DE:(ACP6) (Secreted aspartic protease 6)] [SP:P43095] [DB:swissprot] >pir:[LN:S42073] [AC:S49057:S42073] [PN:aspartic proteinase, SAP6] [CL:pepsin] [OR:*Candida albicans*] [EC:3.4.23.—] [DB:pir2] >gp:[GI:456252] [LN:CASAP5G] [AC:Z30192] [PN:aspartyl protease] [GN:SAP6] [OR:*Candida albicans*] [DB:genpept-pln4] [DE:*C. albicans* (Ca74) SAP6 gene for aspartyl protease.] [SP:P43095] [LE:224] [RE:1480] [DI:direct] |
| orf6.3635 | 126 | 336 | 1767 | 588 | 2999 | 0 | sp:[LN:CAR7_CANAL] [AC *Candida albicans*] [SR:,Yeast] [EC:3.4.23.24] [DE:(ACP7) (Secreted aspartic protease 7)] [SP:P43096] [DB:swissprot] >gp:[GI:578123] [LN:CASAP6G] [AC:Z30193] [PN:aspartyl protease] [GN:SAP7] [OR:*Candida albicans*] [DB:genpept-pln4] [DE:*C. albicans* (Ca74) SAP7 gene for aspartyl protease.] [SP:P43096] [LE:283] [RE:2049] [DI:direct] |
| orf6.3690 | 127 | 337 | 1818 | 605 | 3192 | 0 | gp:[GI:3445504] [LN:CAU59710] [AC:U59710] [PN:phospholipase B precursor] [GN:PLB1] [OR:*Candida albicans*] [DB:genpept-pln4] [DE:*Candida albicans* phospholipase B precursor (PLB1) gene, complete cds.] [LE:1] [RE:1818] [DI:direct] |
| orf6.3713 | 128 | 338 | 2106 | 701 | 360 | 4.40E-34 | pir:[LN:S61146] [AC:S61146] [PN:probable membrane protein YDR349c:hypothetical protein D9476.8] [GN:YDR349c] [OR:*Saccharomyces cerevisiae*] [DB:pir2] [MP:4R] >gp:[GI:849178] [LN:YSCD9476] [AC:U28372:Z71256] [PN:Ydr349cp] [GN:YDR349C] [OR:*Saccharomyces cerevisiae*] [SR:baker's yeast] [DB:genpept-pln5] [DE:*Saccharomyces cerevisiae* chromosome IV cosmid 9476.] [NT:Similar to Yap1p (Swiss Prot. accession number] [LE:326] [RE:2116] [DI:complement] |
| orf6.3785 | 129 | 339 | 5694 | 1897 | 10054 | 0 | gp:[GI:2274847] [LN:D88815] [AC:D88815] [PN:beta-1,3-glucan synthase catalytic subunit 1] [GN:GSC1] [OR:*Candida albicans*] [SR:*Candida albicans* DNA] [DB:genpept-pln4] [DE:*Candida albicans* GSC1 gene for beta-1,3-glucan synthase catalytic subunit 1, complete cds.] [LE:708] [RE:6401] [DI direct] |
| orf6.3803 | 130 | 340 | 1254 | 417 | 2132 | 7.80E-223 | sp:[LN:CAR4_CANAL] [AC:P43093] [GN:SAP4] [OR*Candida albicans*] [SR:,Yeast] [EC:3.4.23.24] [DE:(ACP4) (Secreted aspartic protease 4)] [SP:P43093] [DB:swissprot] >pir:[LN:A55524] [AC:A55524] [PN:aspartic proteinase, secreted] [GN:SAP4] [CL:pepsin] [OR:*Candida albicans*] |

-continued

| ORF | NT Seq ID | AA Seq ID | NT ORF Length | AA ORF Length | Score | Probability | Description |
|---|---|---|---|---|---|---|---|
| | | | | | | | [EC:3.4.—.—] [DB:pir2] >gp:[GI:466346] [LN:YSASAP4] [AC:L25388] [PN:secreted aspartyl proteinase 4] [GN:SAP4] [OR:*Candida albicans*] [SR:*Candida albicans* (strain WO1) DNA] [DB:genpept-pln5] [DE:*Candida albicans* secreted aspartyl proteinase (SAP4) gene, complete cds.] [LE:138] [RE:1391] [DI:direct] |
| orf6.3873 | 131 | 341 | 1926 | 641 | 1198 | 5.60E-124 | gp:[GI:18073453] [LN:CGL302063] [AC:AJ302063] [PN:GAS-3 homologue] [GN:gas3] [OR:*Candida glabrata*] [DB:genpept-pln4] [DE:*Candida glabrata* gas3 gene for GAS-3 homologue.] [LE:151] [RE:1779] [DI:direct] |
| orf6.3897 | 132 | 342 | 4299 | 1432 | 1566 | 0 | sp:[LN:YHY6__YEAST] [AC:P38873] [GN:YHR186C] [OR:*Saccharomyces cerevisiae*] [SR:,Baker's yeast] [DE:intergenic region] [SP:P38873] [DB:swissprot] >pir:[LN:S46686] [AC:S46686] [PN:hypothetical protein YHR186c:hypothetical protein H9998.14] [OR:*Saccharomyces cerevisiae*] [DB:pir2] [MP:8R] >gp:[GI:458938] [LN:YSCH9998] [AC:U00030:U00093] [PN:Yhr186cp] [GN:YHR186c] [OR:*Saccharomyces cerevisiae*] [SR:baker's yeast] [DB:genpept-pln5] [DE:*Saccharomyces cerevisiae* chromosome VIII cosmid 9998.] [NT:Weak similarity to YCR93w (*S. cerevisiae*)] [LE:2827] [RE:7452] [DI:complement] |
| orf6.3954 | 133 | 343 | 4182 | 1393 | 387 | 3.90E-34 | pir:[LN:S64916] [AC:S64916] [PN:probable membrane protein YLR084c:hypothetical protein L2389] [GN:YLR084c] [OR:*Saccharomyces cerevisiae*] [DB:pir2] [MP:12R] >gp:[GI1360451] [LN:SCYLR084C] [AC:Z73256] [OR:*Saccharomyces cerevisiae*] [SR:baker's yeast] [DB:genpept-pln5] [DE:*S. cerevisiae* chromosome XII reading frame ORF YLR084c.] [NT:ORF YLR084c] [LE:495] [RE:4157] [DI:complement] >gp:[GI:1256886] [LN:YSCL9449] [AC:U53880:Y13138] [PN:Ylr084cp] [GN:YLR084C] [OR:*Saccharomyces cerevisiae*] [SR:baker's yeast strain = S288C (AB972)] [DB:genpept-pln5] [DE:*Saccharomyces cerevisiae* chromosome XII cosmid 9449.] [LE:12314] [RE:15976] [DI:complement] |
| orf6.3968 | 134 | 344 | 849 | 283 | | | |
| orf6.3969 | 135 | 345 | 1242 | 413 | 609 | 1.70E-61 | pir:[LN:S70297] [AC:S70297:S59711:S45474:S45942:S39229] [PN:SPS2 protein homolog YBR078w:hypothetical protein YBR0727] [GN:ECM33] [OR:*Saccharomyces cerevisiae*] [DB:pir2] [MP:2R] >gp:[GI:1872127] [LN:SCYBR078W] [AC:Z35947:Y13134] [GN:ECM33] [OR:*Saccharomyces cerevisiae*] [SR:baker's yeast] [DB:genpept-pln4] [DE:*S. cerevisiae* chromosome II reading frame ORF YBR078w.] [NT:ORF YBR078w] [SP:P38248] [LE:831:1219] [RE:888:2567] [DI:directJoin] |
| orf6.4005 | 136 | 346 | 1737 | 578 | 742 | 7.30E-80 | gp:[GI:12057031] [LN:CAL010064] [AC:AJ010064] [PN:mannoprotein MP65] [GN:mp65] [OR:*Candida albicans*] [DB:genpept-pln4] [DE:*Candida albicans* mRNA for MP65 mannoprotein.] [LE:90] [RE:1229] [DI:direct[ |
| orf6.4037 | 137 | 347 | 2265 | 754 | 3925 | 0 | gp:[GI:6453713] [LN:AF038128] [AC:AF038128] [PN:putative phosphilipase B precursor] [GN:PLB1] [OR:*Candida albicans*] [DB:genpept-pln1] [DE:*Candida albicans* putative phospholipase B precursor (PLB1) gene complete cds.] [LE:102] [RE:2366] [DI:direct] |
| orf64050 | 138 | 348 | 1200 | 399 | 640 | 1.50E-64 | sp:[LN:RNT2__ASPOR] [AC:P10281] [GN:RNTB] [OR:*Aspergillus oryzae*] [EC:3.1.27.1] [DE:Ribonuclease T2 precursor, (RNase T2)] [SP:P10281] [DB:swissprot] >pir:[LN:JU0205] [AC:JU0205:S01668] [PN:ribonuclease T2, precursor] [GN:rntB] [CL:*Enterobacter ribonuclease*] [OR:*Aspergillus oryzae*] [EC:3.1.27.1] [DB:pir1] >gp:[GI:2468] [LN:AORNTB] [AC:X61086] [PN:ribonuclease T2] [GN:rntB] [OR:*Aspergillus oryzae*] [DB:genpept-pln2] [DE:*A. oryzae* rntB gene for ribonuclease T2.] [SP:P10281] [LE:213:481:737:962:1217] [RE:430:659:852:1157:1338] [DI:directJoin] |
| orf6.4068 | 139 | 349 | 2154 | 717 | 354 | 2.50E-33 | gp:[GI:14269415] [LN:AF378556] [AC:AF378556] [PN:glucan 1,3 beta-glucosidase-like protein] [OR:*Ophiostoma novo-ulmi*] [DB:genpept-pln2] [DE:*Ophiostoma novo-ulmi* clone 34 glucan 1,3 beta-glucosidase-like protein mRNA, partial cds.] [LE:<1] [RE:709] [DI:direct] |
| orf6.4149 | 140 | 350 | 1407 | 468 | 1203 | 2.00E-124 | sp:[LN:YB12__YEAST] [AC:P38288] [GN:YBR162C:YBR1213] [OR:*Saccharomyces cerevisiae*] [SR:,Baker's yeast] [DE:precursor] [SP:P38288] [DB:swissprot] >pir:[LN:S46033] [AC:S46033:S47311:S55843] [PN:probable membrane protein YBR162c:hypothetical protein YBR1213] [OR:*Saccharomyces cerevisiae*] [DB:pir2] [MP:2R] >gp:[GI:535471] [LN:SCYBR 1212] [AC:X80224] [GN:YBR1213] [OR:*Saccharomyces cerevisiae*] [SR:baker's yeast] [DB:genpept-pln4] [DE:*S. cerevisiae* CDC28, YBR1212, and YBR1213 genes.] [SP:P38288] [LE:3785] [RE:5152] [DI:complement] >gp:[GI:536498] [LN:SCYBR162C] [AC:Z36031:Y13134] [OR:*Saccharomyces cerevisiae*] [SR:baker's yeast] [DB:genpept-pln4] [DE:*S. cerevisiae* chromosome II reading frame ORF YBR162c.] [NT:ORF YBR162c] [SP:P38288] [LE:442] [RE:1809] [DI:complement] |
| orf6.4229 | 141 | 351 | 4326 | 1441 | 168 | 1.30E-10 | pir:[LN:T18403] [AC:T18403] [AC:T18403] [PN:asparagine/aspartate rich protein] [GN:aarp2] [OR:*Plasmodium falciparum*] [DB:pir2] >gp:[GI:1632829] [LN:PFAARPS2] [AC:Y08924] [PN:AARP2 protein] [GN:aarp2] [OR:*Plasmodium falciparum*] [SR:malaria parasite *P. falciparum*] [DB:genpept-inv4] [DE:*P. falciparum* mRNA for AARP2 protein.] [LE:274] [RE:4356] [DI:direct] |

-continued

| ORF | NT Seq ID | AA Seq ID | NT ORF Length | AA ORF Length | Score | Probability | Description |
|---|---|---|---|---|---|---|---|
| orf6.4292 | 142 | 352 | 2262 | 753 | 596 | 3.00E-59 | gp:[GI:14973269] [LN:AE007470] [AC:AE007470:AE005672] [PN:cell wall surface anchor family protein] [GN:SP1772] [OR:*Streptococcus pneumoniae* TIGR4] [DB:genpept-bct1] [DE:*Streptococcus pneumoniae* TIGR4 section 153 of 194 of the complete genome.] [NT:identified by match to PFAM protein family HMM] [LE:2329] [RE:16659] [DI:complement] |
| orf6.4388 | 143 | 353 | 3936 | 1311 | 855 | 3.30E-87 | sp:[LN:HYR1_CANAL] [AC:P46591] [GN:HYR1] [OR:*Candida albicans*] [SR:,Yeast] [DE:Hyphally regulated protein precursor] [SP:P46591] [DB:swissprot] >gp:[GI:1052565] [LN:CAHYR1GN] [AC:Z50123] [PN:hyphally regulated protein] [GN:HYR1] [FN:unknown] [OR:*Candida albicans*] [DB:genpept-pln4] [DE:*Candida albicans* HYR1 gene and promoter region.] [SP:P46591] [LE:1890] [RE:4703] [DI:direct] |
| orf6.4430 | 144 | 354 | 2298 | 765 | 345 | 4.60E-30 | gp:[GI:18447198] [LN:AY075323] [AC:AY075323] [PN:GH09355p] [GN:CG6004] [OR:*Drosophila melanogaster*] [SR:fruit fly] [DB:genpept-inv3] [DE:*Drosophila melanogaster* GH09355 full length cDNA.] [NT:Longest ORF] [LE:4] [RE:4548] [DI:direct] |
| orf6.4501 | 145 | 355 | 852 | 283 | 1423 | 9.00E-148 | gp:[GI:6911253] [LN:AF221545] [AC:AF221545] [PN:PHR3p] [OR:*Candida albicans*] [DB:genpept-pln2] [DE:*Candida albicans* PHR3p gene, complete cds.] [NT:similar to PHR1 and PHR2 of *Candida albicans*] [LE:51:215] [RE:161:1567] [DI:directJoin] |
| orf6.4590 | 146 | 356 | 660 | 219 | 211 | 8.90E-19 | sp:[LN:CW12_YEAST] [AC:Q12127] [GN:CCW12:YLR110C:L9354.7] [OR:*Saccharomyces cerevisiae*] [SR:,Baker's yeast] [DE:Covalently-linked cell wall protein 12 precursor (Protein Alpha 0.6)] [SP:Q12127] [DB:swissprot] >pir:[LN:S64947] [AC:S64947] [PN:hypothetical protein YLR110c:hypothetical protein L2922] [GN:YLR110c] [OR:*Saccharomyces cerevisiae*] [DB:pir2] [MP:12R] >gp:[GI:1360502] [LN:SCYLR110C] [AC:Z73282] [OR:*Saccharomyces cerevisiae*] [SR:baker's yeast] [DB:genpept-pln5] [DE:*S. cerevisiae* chromosome XII reading frame ORF YLR110c.] [NT:ORF YLR110c; internal ORF extracted because of FLO1] [SP:Q12127] [LE:386] [RE:787] [DI:complement] >gp:[GI:1256873] [LN:YSCL9354] [AC:U53878:Y13138] [PN:Ylr110cp] [GN:YLR110C] [OR:*Saccharomyces cerevisiae*] [SR:baker's yeast strain = S288C (AB972)] [DB:genpept-pln5] [DE:*Saccharomyces cerevisiae* chromosome XII cosmid 9354.] [NT:Similar to *S. cerevisiae* Flocculation protein Flo1] [LE:4760] [RE:5161] [DI:complement] |
| orf6.4644 | 147 | 357 | 1176 | 391 | 2000 | 8.10E-209 | gp:[GI:7548425] [LN:YSASAP1S24] [AC:L12449] [PN:secreted aspartyl proteinase 1] [GN:SAP1] [OR:*Candida albicans*] [DB:genpept-pln5] [DE:*Candida albicans* secreted aspartyl proteinase 1 (SAP1) gene, SAP1-2.4 allele, complete cds.] [NT:aspartyl protease] [LE:1309] [RE:2484] [DI:direct] >gp:[GI:7548465] [LN:YSASAP1W24] [AC:L12451] [PN:secreted aspartyl proteinase 1] [GN:SAP1] [OR:*Candida albicans*] [DB:genpept-pln5] [DE:*Candida albicans* strain WO1 secreted aspartyl proteinase 1 (SAP1) gene, SAP1-2.4 allele, complete cds.] [NT:aspartyl protease] [LE:1313] [RE:2488] [DI:direct] |
| orf6.4725 | 148 | 358 | 3750 | 1249 | 1028 | 3.40E-106 | sp:[LN:HYR1_CANAL] [AC:P46591] [GN:HYR1] [OR:*Candida albicans*] [SR:,Yeast] [DE:Hyphally regulated protein precursor] [SP:P46591] [DB:swissprot] >gp:[GI:1052565] [LN:CAHYR1GN] [AC:Z50123] [PN:hyphally regulated protein] [GN:HYR1] [FN:unknown] [OR:*Candida albicans*] [DB:genpept-pln4] [DE:*Candida albicans* HYR1 gene and promoter region.] [SP:P46591] [LE:1890] [RE:4703] [DI:direct] |
| orf6.474 | 149 | 359 | 1158 | 385 | 701 | 3.40E-71 | gp:[GI:218459] [LN:YSCPIR2P] [AC:D13741] [PN:Pir2p] [GN:PIR2] [OR:*Saccharomyces cerevisiae*] [SR:*Saccharomyces cerevisiae* DNA] [DB:genpept-pln5] [DE:*S. cerevisiae* Pir2p gene.] [LE:134] [RE:1375] [DI:direct] |
| orf6.4883 | 150 | 360 | 1905 | 634 | 3342 | 0 | sp:[LN:HWP1_CANAL] [AC:P46593:P87019:O13424] [GN:HWP1:ECE2] [OR:*Candida albicans*] [SR:,Yeast] [DE:Hypha wall protein 1 (Cell elongation protein 2)] [SP:P46593:P87019:O13424] [DB:swissprot] >gp:[GI:1915979] [LN:CAU64206] [AC:U64206] [PN:hyphal wall protein 1] [GN:HWP1] [OR:*Candida albicans*] [DB:genpept-pln4] [DE:*Candida albicans* hyphal wall protein 1 (HWP1) gene, complete cds.] [NT:hyphal surface protein] [LE:503] [RE:2407] [DI:direct] |
| orf6.4889 | 151 | 361 | 2145 | 714 | 3208 | 0 | gp:[GI:9963982] [LN:AF254142] [AC:AF254142] [PN:repressed by TUP1 protein 1] [GN:RBT1] [OR:*Candida albicans*] [DB:genpept-pln2] [DE:*Candida albicans* repressed by TUP1 protein 1 (RBT1) gnee, complete cds.] [NT:cell wall protein; GPI modified; predicted] [LE:617] [RE:2869] [DI:direct] |
| orf6.4915 | 152 | 362 | 4044 | 1347 | 4335 | 0 | sp:[LN:ALA1_CANAL] [AC:O13368] [GN:ALA1:ALS5] [OR:*Candida albicans*] [SR:,Yeast] [DE:Agglutinin-like protein ALA1 precursor (Agglutinin-like adhesin)] [SP:O13368] [DB:swissprot] >pir:[LN:T30531] [AC:T30531] [PN:agglutinin-like adhesin] [GN:ALA1] [CL:yeast glucan 1,4-alpha-glucosidase homolog:glucan 1,4-alpha-glucosidase homology] [OR:*Candida albicans*] [DB:pir2] >gp:[GI:2522219] [LN:AF025429] [AC:AF025429] [PN:agglutinin-like adhesin] [GN:ALA1] [FN:cell adhesion protein] [OR:*Candida albicans*] [DB:genpept-pln1] [DE:*Candida albicans* agglutinin-like adhesin (ALA1) gene, complete cds.] [LE:327] [RE:4586] [DI:direct] |

-continued

| ORF | NT Seq ID | AA Seq ID | NT ORF Length | AA ORF Length | Score | Probability | Description |
|---|---|---|---|---|---|---|---|
| or-f6.5053 | 153 | 363 | 816 | 271 | 1403 | 2.10E-145 | sp:[LN:KRE9__CANAL] [AC:O74226] [GN:KRE9] [OR:*Candida ablicans*] [SR:,Yeast] [DE:Cell wall synthesis protein KRE9 precursor] [SP:O74226] [DB:swissprot] >gp:[GI:3435198] [LN:AF069763] [AC:AF069763] [PN:cell wall synthesis protein Kre9p] [GN:KRE9] [FN:cell wall synthesis protein beta-1,6-glucan synthesis] [OR:*Candida albicans*] [DB:genpept-pln1] [DE:*Candida albicans* cell wall synthesis protein Kre9p (KRE9) gene, complete cds.] [LE:1] [RE:816] [DI:direct] |
| orf6.5138 | 154 | 364 | 1242 | 413 | 561 | 2.20E-56 | pir:[LN:S61999] [AC:S61999] [PN:hypothetical protein YPL123c:hypothetical protein LPH4c] [GN:YPL123c] [CL:yeast hypothetical protein YPL123c] [OR:*Saccharomyces cerevisiae*] [DB:pir1] [MP:16L] >gp:[GI:1163091] [LN:SCU43503] [AC:U43503:U00094] [PN:Ypl123cp] [GN:YPL123C] [OR:*Saccharomyces cerevisiae*] [SR:baker's yeast] [DB:genpept-pln4] [DE:*Saccharomyces cerevisiae* chromosome XVI cosmid 8209/8002.] [NT:similar to *Aspergillus oryzae* encoded ribonuclease] [LE:7784] [RE:9088] [DI complement] |
| orf6.5153 | 155 | 365 | 1041 | 346 | 680 | 7.00E-69 | sp:[LN:PIR1__YEAST] [AC:Q03178] [GN:PIR1:CCW6:YKL164C:YKL618] [OR:*Saccharomyces cerevisiae*] [SR:,Baker's yeast] [DE:PIR1 protein precursor (Covalently-linked cell wall protein 6)] [SP:Q03178] [DB:swissprot] >pir:[LN:S33650] [AC:S33650:S37994:S37787:S44564:S30795] [PN:heat shock protein PIR1 [accepted]:protein YKL164c:protein YKL618] [GN:PIR1] [OR:*Saccharomyces cerevisiae*] [DB:pir2] [MP:11L] >gp:[GI:407484] [LN:SCDCHR11] [AC:Z26877] [PN:unknown] [OR:*Saccharomyces cerevisiae*] [SR:baker's yeast] [DB:genpept-pln4] [DE:*S. cerevisiae* (S288C) 36.2kb DNA fragment from chromosome 11.] [SP:Q03178] [LE:5887] [RE:6912] [DI:complement] >gp:[GI:486287] [LN:SCYKL164C] [AC:Z28164:Y13137] [GN:PIR1] [OR:*Saccharomyces cerevisiae*] [SR:baker's yeast] [DB:genpept-pln5] [DE:*S. cerevisiae* chromosome XI reading frame ORF YKL164c.] [NT:ORF YKL164c] [SP:Q03178] [LE:1103] [RE:2128] [DI:complement] >gp:[GI:218457] [LN:YSCPIR1P] [AC:D13740] [PN:Pir1p] [GN:PIR1] [OR:*Saccharomyces cerevisiae*] [SR:*Saccharomyces cerevisiae* DNA] [DB:genpept-pln5] [DE:*S. cerevisiae* Pir1p gene.] [LE:139] [RE:1164] [DI:direct] |
| orf6.5166 | 156 | 366 | 1536 | 511 | 230 | 5.30E-18 | sp:[LN:AMYH__YEAST] [AC:P08640:P08068] [GN:STA1:STA2:MAL5:YIR019C] [OR:*Saccharomyces cerevisiae*] [SR:,Baker's yeast] [EC:3.2.1.3] [DE:glucosidase) (1,4-alpha-D-glucan glucohydrolase)] [SP:P08640:P08068] [DB:swissprot] >pir:[LN:S4878] [AC:S48478:A26877:B26877:S27281:JC6123] [PN:glucan 1,4-alpha-glucosidase,:extracellular glucoamylase:mucin-like protein MUC1:protein YIR019c] [GN:MUC1:STA2:MAL5:DEX2:S0001458] [CL:yeast glucan 1,4-alpha-glucosidase homolog:glucan 1,4-alpha-glucosidase homology] [OR:*Saccharomyces cerevisiae*] [EC:3.2.1.3] [DB:pir1] [MP:9R] >gp:[GI:557822] [LN:SC9168] [AC:Z38061:Z47047] [GN:mal5] [OR:*Saccharomyces cerevisiae*] [SR:baker's yeast] [DB:genpept-pln4] [DE:*S. cerevisiae* chromosome IX cosmid 9168.] [NT:mal5, sta1, len:1367, CAI: 0.3, AMYH__YEAST P08640] [SP:P08640] [LE:1423] [RE:5526] [DI:complement] >gp:[GI:1304387] [LN:SCU30626] [AC:U30626] [PN:glucoamylase] [GN:MUC1] [OR:*Saccharomyces cerevisiae* var. *diastaticus*] [DB:genpept-pln4] [DE:*Saccharomyces cerevisiae* var. *diastaticus* glucoamylase (MUC1) gene, complete cds.] [NT:ancestral gene of the STA gene family] [LE:2548] [RE:6651] [DI:direct] |
| orf6.5210 | 157 | 367 | 1401 | 466 | 2447 | 2.90E-256 | gp:[GI:6978036] [LN:AF189152] [AC:AF189152] [PN:secretory lipase] [GN:LIP2] [OR:*Candida albicans*] [DB:genpept-pln2] [EC:3.1.1.3] [DE:*Candida albicans* secretory lipase (LIP2) gene, complete cds.] [NT:lipase] [LE:369] [RE:1769] [DI:direct] |
| orf6.5227 | 158 | 368 | | 2052683 | 507 | 6.80E-66 | sp:[LN:SPO1__YEAST] [AC:P53541] [GN:SPO1:YNL012W:N2858] [OR:*Saccharomyces cerevisiae*] [SR:,Baker's yeast] [DE:Sporulation protein SPO1] [SP:P53541] [DB:swissprot] >pir:[LN:S62110] [AC:S62110:S59730:S62924:JC5179] [PN:lysophospholipase,:phospholipase B:protein N2858:protein YNL012w:transcription regulator SPO1] [GN:SPO1] [CL:yeast lysophospholipase] [OR:*Saccharomyces cerevisiae*] [EC:3.1.1.5] [DB:pir2] [MP:14L] >gp:[GI:1301834] [LN:SCYNL012W] [AC:Z71288:Y13139] [GN:SPO1] [OR:*Saccharomyces cerevisiae*] [SR:baker's yeast] [DB:genpept-pln5] [DE:*S. cerevisiae* chromosome XIV reading frame ORF YNL012w.] [NT:ORF YNL012w] [SP:P53541] [LE:545] [RE:2155] [DI:direct] >gp:[GI:1109598] [LN:YSCSPO1G] [AC:L39372] [PN:phospholipase B] [GN:SPO1] [OR:*Saccharomyces cerevisiae* ] [SR:baker's yeast] [DB:genpept-pln5] [DE:*Saccharomyces cerevisiae* transcription regulator (SPO1) mRNA, complete cds.] [NT:homologue] [LE:498] [RE:2108] [DI:direct] |
| orf6.5306 | 159 | 369 | 1197 | 398 | 2017 | 1.30E-210 | sp:[LN:CAR2__CANAL] [AC:P28871:P43097] [GN:SAP2:PRA11:PRA2] [OR:*Candida albicans*] [SR:,Yeast] [EC:3.4.23.24] [DE:(ACP2) (Secreted aspartic protease 2)] [SP:P28871:P43097] [DB:swissprot] >pir:[LN:A45280] [AC:A45280:A60342] [PN:candidapepsin, 2 precursor [validated]:*Candida albicans* aspartic proteinase:secretory acid proteinase 2 (SAP2)] [GN:PRA11] [CL:pepsin] [OR:*Candida albicans*] [EC:3.4.23.24] [DB:pir2] >gp:[GI:170841] [LN:YSACPA] [AC:M83663] [PN:aspartyl proteinase] [GN:PrA2] [OR:*Candida* |

-continued

| ORF | NT Seq ID | AA Seq ID | NT ORF Length | AA ORF Length | Score | Probability | Description |
|---|---|---|---|---|---|---|---|
| | | | | | | | albicans] [SR:Candida albicans (library: lambda-EMBL4; ATCC 10261) DNA] [DB:genpept-pln5] [DE:Candida albicans secreted aspartyl proteinase gene, complete cds.] [NT:pre-pro peptide] [LE:126] [RE:1322] [DI:direct] |
| orf6.5354 | 160 | 370 | 1962 | 653 | 618 | 8.80E-63 | sp:[LN:MUC2_HUMAN] [AC:Q02817:Q14878] [GN:MUC2:SMUC] [OR:Homo sapiens] [SR:,Human] [DE:Mucin 2 precursor (Intestinal mucin 2)] [SP:Q02817:Q14878] [DB:swissprot] >gp:[GI:454154] [LN:HUMMUC2X] [AC:L21998] [PN:mucin] [OR:Homo sapiens] [SR:human] [DB:genpept-pri17] [DE:Homo sapiens intestinal mucin (MUC2) mRNA, complete cds.] [LE:28] [RE:15567] [DI:direct] |
| orf6.5529 | 161 | 371 | 2619 | 872 | 414 | 1.50E-36 | sp:[LN:AMYH_YEAST] [AC:P08640:P08068] [GN:STA1:STA2:MAL5:YIR019C] [OR:Saccharomyces cerevisiae] [SR:,Baker's yeast] [EC:3.2.1.3] [DE:glucosidase] (1,4-alpha-D-glucan glucohydrolase)] [SP:P08640:P08068] [DB:swissprot] >pir:[LN:S48478] [AC:S48478:A26877:B26877:S27281:JC6123] [PN:glucan 1,4-alpha-glucosidase,:extracellular glucoamylase:mucin-like protein MUC1:protein YIR019c] [GN:MUC1:STA2:MAL5:DEX2:S0001458] [CL:yeast glucan 1,4-alpha-glucosidase homolog:glucan 1,4-alpha-glucosidase homology] [OR:Saccharomyces cerevisiae] [EC:3.2.1.3] [DB:pir1] [MP:9R] >gp:[GI:557822] [LN:SC9168] [AC:Z38061:Z47047] [GN:mal5] [OR:Saccharomyces cerevisiae] [SR:baker's yeast] [DB:genpept-pln4] [DE:S. cerevisiae chromosome IX cosmid 9168.] [NT:mal4, sta1, len: 1367, CAI: 0.3, AMYH_YEAST P08640] [SP:P08640] [LE:1423] [RE:5526] [DI:complement] >gp:[GI:1304387] [LN:SCU30626] [AC:U30626] [PN:glucoamylase] [GN:MUC1] [OR:Saccharomyces cerevisiae var. diastaticus] [DB:genpept-pln4] [DE:Saccharomyces cerevisiae var. diastaticus glucoamylase (MUC1) gene, complete cds.] [NT:ancestral gene of the STA gene family] [LE:2548] [RE:6651] [DI:direct] |
| orf6.553 | 162 | 372 | 2055 | 684 | 530 | 2.60E-68 | sp:[LN:SPO1_YEAST] [AC:P53541] [GN:SPO1:YNL012W:N2858] [OR:Saccharomyces cerevisae] [SR:,Baker's yeast] [DE:Sporulation protein SPO1] [SP:P53541] [DB:swissprot] >pir:]LN:S62110] [AC:S62110:S59730:S62924:JC5179] [PN:lysophospholipase,:phospholipase B:protein N2858:protein YNL012w:transcription regulator SPO1] [GN:SPO1] [CL:yeast lysophospholipase] [OR:Saccharomyces cerevisiae] [EC:3.1.1.5] [DB:pir2] [MP:14L] >gp:[GI:1301834] [LN:SCYNL012W] [AC:Z71288:Y13139] [GN:SPO1] [OR:Saccharomyces cerevisiae] [SR:baker's yeast] [DB:genpept-pln5] [DE:S. cerevisiae chromosome XIV reading frame ORF YNL012w.] [NT:ORF YNL012w] [SP:P53541] [LE:545] [RE:2155] [DI:direct] >gp:[GI:1109598] [LN:YSCSPO1G] [AC:L39372] [PN:phosphilipase B] [GN:SPO1] [OR:Saccharomyces cerevisiae] [SR:baker's yeast] [DB:genpept-pln5] [DE:Saccharomyces cerevisiae transcription regulator (SPO1) mRNA complete cds.] [NT:homologue] [LE:498] [RE:2108] [DI:direct] |
| orf6.5940 | 163 | 373 | 3531 | 1176 | 950 | 1.20E-96 | gp:[GI:13810411] [LN:SPAPJ4664] [AC:AL590884] [PN:hypothetical protein; sequence orphan; low] [GN:SPBPJ4664.02] [OR:Schizosaccharomyces pombe] [SR:fission yeast] [DB:genpept-pln5] [DE:S. pombe chromosome I cosmid c4664.] [LE:2430] [RE:14345] [DI:direct] >gp:[GI:14018379] [LN:SPBPJ4664] [AC:AL591302] [PN:hypothetical protein; sequence orphan; low] [GN:SPBPJ4664.02] [OR:Schizosaccharomyces pombe] [SR:fission yeast] [DB:genpept-pln5] [DE:S. pombe chromosome II cosmid c4664.] [LE:2430] [RE:14345] [DI:direct] |
| orf6.6053 | 164 | 374 | 3336 | 1111 | 5878 | 0 | sp:[LN:CHS3_CANAL] [AC:P30573] [GN:CHS3] [OR:Candida albicans] [SR:,Yeast] [EC:2.4.1.16] [DE:transferase 3) (Class-IV chitin synthase 3)] [SP:P30573] [DB:swissprot] >gp:[GI:218362] [LN:YSACACHS3] [AC:D13454] [PN:chitin synthase III] [GN:CACHS3] [OR:Candida albicans] [SR:Candida albicans (strain:IFO1060) DNA] [DB:genpept-pln5] [DE:Candida albicans CACHS3 gene for chitin synthase III.] [LE:268] [RE:3909] [DI:direct] |
| orf6.6176 | 165 | 375 | 4716 | 1571 | 5387 | 0 | pir:[LN:T30576] [AC:T30576] [PN:glucan synthase] [GN:GSL1] [OR:Candida albicans] [DB:pir2] >gp:[GI:2274849] [LN:D88816] [PN:glucan synthase] [GN:GSL1] [OR:Candida albicans] [SR:Candida albicans DNA] [DB:genpept-pln4] [DE:Candida albicans GSL1 gene for glucan synthase, complete cds.] [LE:1053] [RE:4325] [DI:direct] |
| orf6.6206 | 166 | 376 | 1899 | 632 | 1680 | 3.90E-175 | sp:[LN:PLB1_TORDE] [AC:Q11121] [OR:Torulaspora delbrueckii] [SR:,Yeast:Saccharomyces rosei] [EC:3.1.1.5] [DE:Lysophospholipase precursor, (Phospholipase B)] [SP:Q11121] [DB:swissprot] >gp:[GI:1020416] [LN:YSCBGENE] [AC:D32134] [PN:phospholipase B] [OR:Torulaspora delbrueckii] [SR:Saccharomyces rosei (strain YL-32) (library: Charomid 9-36) DNA] [DB:genpept-pln5] [DE:Saccharomyces rosei gene for phospholipase B, complete cds.] [LE:388] [RE:2337] [DI:direct] |
| orf6.6260 | 167 | 377 | 1635 | 544 | 2800 | 9.70E-294 | sp:[LN:PHR2_CANAL] [AC:O13318] [GN:PHR2] [OR:Candida albicans] [SR:,Yeast] [DE:PH responsive protein 2 precursor (PH-regulated protein 2)] [SP:O13318] [DB:swissprot] >gp:[GI:2293530] [LN:AF011386] [AC:AF011386] [PN:pH-regulated protein 2] [GN:PHR2] [OR:Candida albicans] [DB:genpept-pln1] [DE:Candida albicans pH-regulated protein 2 (PHR2) gene, complete cds.] [LE:52] [RE:1692] [DI:direct] |

| ORF | NT Seq ID | AA Seq ID | NT ORF Length | AA ORF Length | Score | Probability | Description |
|---|---|---|---|---|---|---|---|
| orf6.6348 | 168 | 378 | 915 | 305 | 1552 | 1.20E-161 | pir:[LN:T18238] [AC:T18238] [PN:lysophospholipase,] [OR:*Candida albicans*] [EC:3.1.1.5] [DB:pir2] >gp:[GI:3859722] [LN:CAC41C10] [AC:AL033501] [PN:lysophospholipase] [GN:Ca41c10.12] [OR:*Candida albicans*] [DB:genpept-pln4] [DE:*C. albicans* cosmid Ca41C10.] [NT:Ca41C10.12, phospholipase, len: 754 aa, similar to] [LE:34742] [RE:37006] [DI:direct] |
| orf6.6575 | 169 | 379 | 858 | 286 | 619 | 1,50E-62 | sp:[LN:YB12__YEAST] [AC:P38288] [GN:YBR162C:YBR1213] [OR:*Saccharomyces cerevisiae*] [SR:,Baker's yeast] [DE:precursor] [SP:P38288] [DB:swissprot] >pir:[LN:S46033] [AC:S46033:S47311:S55843] [PN:probable membrane protein YBR162c:hypothetical protein YBR1213] [OR:*Saccharomyces cerevisiae*] [DB:pir2] [MP:2R] >gp:[GI:535471] [LN:SCYBR1212] [AC:X80224] [GN:YBR1213] [OR:*Saccharomyces cerevisiae*] [SR:baker's yeast] [DB:genpept-pln4] [DE:*S. cerevisiae* CDC28, YBR1212, and YBR1213 genes.] [SP:P38288] [LE:3785] [RE:5152] [DI:complement] >gp:[GI:536498] [LN:SCYBR162C] [AC:Z36031:Y13134] [OR:*Saccharomyces cerevisiae*] [SR:baker's yeast] [DB:genpept-pln4] [DE:*S. cerevisiae* chromosome II reading frame ORF YBR162c.] [NT:ORF YBR162c] [SP:P38288] [LE:442] [RE:1809] [DI:complement] |
| orf6.6664 | 170 | 380 | 1440 | 479 | 837 | 1.80E-106 | gp:[GI:4007653] [LN:PAJ002195] [AC:AJ002195] [PN:exo-1,3-beta-glucanase] [GN:PAEXG1] [OR:*Pichia anomala*] [DB:genpept-pln4] [EC:3.2.1.58] [DE:*Pichia anomala* PAEXG1 gene.] [LE:355] [RE:1851] [DI:direct] |
| orf6.6782 | 171 | 381 | 1689 | 562 | 2993 | 0 | sp:[LN:HEX1__CANAL] [AC:P43077] [GN:HEX1] [OR:*Candida albicans*] [SR:,Yeast] [EC:3.2.1.52] [DE:glucosaminidase) (Beta-GLCNACASE) (Beta-N-acetylhexosaminidase)] [SP:P43077] [DB:swissprot] >gp:[GI:7547263] [LN:YSAHEX1A] [AC:L26488] [PN:hexosaminidase precursor] [GN:HEX1] [OR:*Candida albicans*] [DB:genpept-pln5] [EC:3.2.1.52] [DE:*Candida albicans* hexosaminidase precursor (HEX1) gene, complete cds.] [NT:beta-N-acetylglucosaminidase] [LE:422] [RE:2110] [DI:direct] |
| orf6.6957 | 172 | 382 | 1392 | 463 | 2408 | 4.00E-252 | gp:[GI:7769756] [LN:AF191318] [AC:AF191318] [PN:secretory lipase 5] [GN:LIP5] [OR:*Candida albicans*] [DB:genpept-pln2] [EC:3.1.1.3] [DE:*Candida albicans* secretory lipase 5 (LIP5) gene, complete cds.] [NT:Lip5; LIP] [LE:336] [RE:1727] [DI:direct] |
| orf6.6963 | 173 | 383 | 759 | 252 | 1275 | 4.70E-132 | gp:[GI:8809747] [LN:AF191322] [AC:AF191322] [PN:secretory lipase 9] [GN:Lip9] [OR:*Candida albicans*] [DB:genpept-pln2] [EC:3.1.1.3] [DE:*Candida albicans* secretory lipase 9 (Lip9) gene, complete cds.] [NT:LIP] [LE:288] [RE:1649] [DI:direct] |
| orf6.6964 | 174 | 384 | 666 | 221 | 1063 | 1.40E-109 | gp:[GI:8809747] [LN:AF191322] [AC:AF191322] [PN:secretory lipase 9] [GN:Lip9] [OR:*Candida albicans*] [DB:genpept-pln2] [EC:3.1.1.3] [DE:*Candida albicans* secretory lipase 9 (Lip9) gene, complete cds.] [NT:LIP] [LE:288] [RE:1649] [DI:direct] |
| orf6.708 | 175 | 385 | 1137 | 378 | 1891 | 3.00E-197 | gp:[GI:12057031] [LN:CAL010064] [AC:AJ010064] [PN:mannoprotein MP65] [GN:mp65] [OR:*Candida albicans*] [DB:genpept-pln4] [DE:*Candida albicans* mRNA for MP65 mannoprotein.] [LE:90] [RE:1229] [DI:direct] |
| orf6.7314 | 176 | 386 | 1635 | 544 | 2692 | 2.70E-282 | sp:[LN:CAR9__CANAL] [AC:O42779] [GN:SAP9] [OR:*Candida albicans*] [SR:,Yeast] [EC:3.4.23.24] [DE:(ACP9) (Secreted aspartic protease 9)] [SP:O42779] [DB:swissprot] >gp:]GI2811290] [LN:AF043331] [AC:AF043331] [PN:secreted aspartyl proteinase] [GN:SAP9] [OR:*Candida albicans*] [DB:genpept-pln1] [DE:*Candida albicans* secreted aspartyl proteinase (SAP9) gene, complete cds.] [NT:Sap9p] [LE:255] [RE:1889] [DI:direct] |
| orf6.7355 | 177 | 387 | 1416 | 471 | 2411 | 1.90E-252 | gp:[GI:7769752] (LN:AF191316] [AC:AF191316] [PN:secretory lipase 3] [GN:LIP3] [OR*Candida albicans*] [DB:genpept-pln2] [EC:3.1.1.3] [DE:*Candida albicans* secretory lipase 3 (LIP3) gene, complete cds.] [NT:Lip3; LIP] [LE:332] [RE:1747] [DI:direct] |
| orf6.7401 | 178 | 388 | 1728 | 575 | 200 | 1.10E-14 | pir:[LN:T45463] [AC:T45463] [PN:membrane glycoprotein [imported]] [CL:*equine herpesvirus* glycoprotein X:*equine herpesvirus* 1 glycoprotein homology] [OR:*equine herpesvirus 1*] [DB:pir2] >gp:[GI:2114323] [LN:D88734] [AC:D88734] [PN:membrane glycoprotein] [GN:ORF71] [OR:*Equine herpesvirus* 1] [SR:*Equine herpesvirus* 1 (strain:BK343, isolate:3F clone) DNA] [DNA] [DB:genpept-vrl2] [DE:*Equine herpesvirus* 1 DNA for membrane glycoprotein, complete cds.] [LE:118] [RE:2721] [DI:direct] |
| orf6.7448 | 179 | 389 | 1356 | 451 | 1198 | 7.80E-129 | sp:[LN:YOD0__YEAST] [AC:Q08193] [GN:YOL030W] [OR:*Saccharomyces cerevisiae*] [SR:,Baker's yeast] [DE:precursor] [SP:Q08193] [DB:swissprot] >pir:[LN:S66713] [AC:S66713] [PN:hypothetical protein YOL030w:hypothetical protein O2145] [GN:YOL030w] [CL:glycophospholipid-anchored surface glycoprotein GAS1] [OR:*Saccharomyces cerevisiae*] [DB:pir2] [MP:15L] >gp:[GI:1419819] [LN:SCYOL030W] [AC:Z74772:Y13140] [OR:*Saccharomyces cerevisiae*] [SR:baker's yeast] [DB:genpept-pln5] [DE:*S. cerevisiae* chromosome XV reading frame ORF YOL030w.] [NT:ORF YOL030w] [SP:Q08193] [LE:658] [RE:2112] [DI:direct] |
| orf6.7480 | 180 | 390 | 1356 | 451 | 1265 | 5.30E-131 | sp:[LN:YM77__YEAST] [AC:Q05031] [GN:YMR238W:YM9959.20] [OR:*Saccharomyces cerevisiae*] [SR:,Baker's yeast] [DE:Hypothetical 50.5 kDa protein in RNA1-RNT1 intergenic region] [SP:Q05031] [DB:swissprot] >pir:[LN:S57605] [AC:S57605] [PN:probable membrane protein YMR238w:hypothetical protein YM9959.20] [GN:DFG5] |

-continued

| ORF | NT Seq ID | AA Seq ID | NT ORF Length | AA ORF Length | Score | Probability | Description |
|---|---|---|---|---|---|---|---|
| | | | | | | | [CL:*Schizosaccharomyces pombe* hypothetical protein SPCC970.02] [OR:*Saccharomyces cerevisiae*] [DB:pir2] [MP:13R] >gp:[GI:887619] [LN:SC9959] [AC:Z49939:Z71257] [PN:unknown] [OR:*Saccharomyces cerevisiae*] [SR:baker's yeast] [DB:genpept-pln4] [DE:*S. cerevisiae* chromosome XIII cosmid 9959.] [NT:YM9959.20, unknown, len: 458, CAI: 0.18, similar to] [SP:Q05031] [LE:37400] [RE:38776] [DI:direct] |
| orf6.7524 | 181 | 391 | 1647 | 548 | 2827 | 1.30E-296 | gp:[GI:8132882] [LN:AF247190] [AC:AF247190] [PN:Phr1p] [GN:PHR1] [OR:*Candida albicans*] [DB:genpept-pln2] [DE:*Candida albicans* Phr1p (PHR1) gene, PHR1-2 allele, complete cds.] [LE:262] [RE:1908] [DI:direct] |
| orf6.7534 | 182 | 392 | 1362 | 453 | 2131 | 9.40E-223 | gp:[GI:7673038] [LN:AF146440] [AC:AF146440] [PN:secretory aspartyl proteinase] [GN:SAP10] [OR:*Candida albicans*] [DB:genpept-pln2] [DE:*Candida albicans* secretory aspartyl proteinase (SAP10) gene, complete cds.] [NT:secreted aspartyl protease; secreted acid] [LE:130] [RE:1455] [DI:direct] |
| orf6.7594 | 183 | 393 | 1113 | 370 | 102 | 0.00026 | sp:[LN:TROP_HUMAN] [AC:Q12816:Q9NU89:Q9UPN8[ [GN:TRO:KIAA1114] [OR:*Homo sapiens*] [SR:,Human] [DE:*Trophinin*] [SP:Q12816:Q9NU89:Q9UPN8] [DB:swissprot] >gp:[GI:7529568] [LN:HSDA14C6] [AC:AL049732] [PN:dA14C6.1 (KIAA1114 (similar to BCG1 and melanoma] [GN:dA14C6.1] [OR:*Homo sapiens*] [SR:human] [DB:genpept-pri16] [DE:Human DNA sequence from clone RP6-14C6 on chromosome Xp11.21-11.23. Contains part of a putative gene for a novel protein similar to ITIH3 (pre-alpha (globulin) inhibitor, H3 polypeptide), the gene KIAA1114 for a protein similar to BCG1 and melanoma associated antigen MAGE-D1, the PFKFB1 gene for 6-phosphofructo-2-kinase/fructose-2,6-biphosphatase 1, ESTs, STSs and GSSs, complete sequence.] [NT:match:proteins: Tr:O76058 Tr:Q9Y5V3] [LE:89186:90972:91191:91510] [RE:90289:91076:91254:91589] [DI:directJoin] |
| orf6.795 | 184 | 394 | 1185 | 394 | 455 | 2.60E-45 | gp:[GI:3169132] [LN:AB014495] [AC:AB014495] [PN:phospholipase B] [GN:KIPLB] [OR:*Kluyveromyces lactis*] [SR:*Kluyveromyces lactis* (strain:IFO 1090) cDNA to genomic RNA] [DB:genpept-pln1] [DE:*Kluyveromyces lactis* gene for phospholipase B, complete cds.] [LE:219] [RE:2141] [DI:direct] |
| orf6.7959 | 185 | 395 | 3234 | 1077 | 412 | 7.00E-73 | sp:[LN:YB9T_YEAST] [AC:P38148] [GN:YBR276C:YBR2013] [OR:*Saccharomyces cerevisiae*] [SR:,Baker's yeast] [EC:3.1.3.48] [DE:Probable protein-tyrosine phosphatase YBR276C.] [SP:P38148] [DB:swissprot] >pir:[LN:S44538] [AC:S44538:S46158:S39132] [PN:probable protein-tyrosine-phosphatase,:hypothetical protein YBR2013:hypothetical protein YBR276c] [GN:PPS1:YBR276c] [CL:*Saccharomyces* protein-tyrosine-phosphatase YBR2013:VH1-type dual specificity phosphoprotein phosphatase homology] [OR:*Saccharomyces cerevisiae*] [EC:3.1.3.48] [DB:pirl] [MP:2R] >gp:[GI:429121] [LN:SCDPB3] [AC:X76053] [OR:*Saccharomyces cerevisiae*] [SR:baker's yeast] [DB:genpept-pln4] [DE:*S. cerevisiae* (s288c) RIF1, DPB3, YmL27 and SNF5 genes.] [NT:YBR2013-ORF] [SP:P38148] [LE:3804] [RE:6227] [DI:complement] >gp:[GI:536717] [LN:SCYBR276C] [AC:Z36145:Y13134] [GN:PPS1] [OR:*Saccharomyces cerevisiae*] [SR:baker's yeast] [DB:genpept-pln4] [DE:*S. cerevisiae* chromosome II reading frame ORF YBR276c.] [NT:ORF YBR276c] [SP:P38148] [LE:2578] [RE:5001] [DI:complement] |
| orf6.796 | 186 | 396 | 915 | 304 | 686 | 9.10E-70 | gp:[GI:3445504] [LN:CAU59710] [AC:U59710] [PN:phospholipase B precursor] [GN:PLB1] [OR:*Candida albicans*] [DB:genpept-pln4] [DE:*Candida albicans* phospholipase B precursor (PLB1) gene, complete cds.] [LE:1] [RE:1818] [DI:direct] |
| orf6.7977 | 187 | 397 | 1119 | 372 | 1074 | 9.40E-111 | sp:[LN:YK22_YEAST] [AC:P36135] [GN:YKR042W] [OR:*Saccharomyces cerevisiae*] [SR:,Baker's yeast] [DE:Hypothetical 46.9 kDa protein in GAP1-NAP1 intergenic region] [SP:P36135] [DB:swissprot] >pir:[LN:S38114] [AC:S38114] [PN:hypothetical protein YKR042W] [GN:UTH1] [CL:*Saccharomyces* NCA3 protein] [OR:*Saccharomyces cerevisiae*] [DB:pir2] [MP:11R] >gp:[GI:486485] [LN:SCYKR042W] [AC:Z28267:Y13137] [GN:UTH1] [OR:*Saccharomyces cerevisiae*] [SR:baker's yeast] [DB:genpept-pln5] [DE:*S. cerevisiae* chromosome XI reading frame ORF YKR042w.] [NT:ORF YKR042w] [SP:P36135] [LE:322] [RE:1674] [DI:direct] |
| orf6.799 | 188 | 398 | 1155 | 384 | 963 | 6.20E-99 | sp:[LN:YJR1_YEAST] [AC:P46992] [GN:YJL171C:J0512] [OR:*Saccharomyces cerevisiae*] [SR:,Baker's yeast] [DE:Hypothetical 43.0 kDa protein in CPS1-FPP1 intergenic region] [SP:P46992] [DB:swissprot] >pir:[LN:S56954] [AC:S56954] [PN:protein YBR162c homolog YJL171c:probable membrane protein YJL171c:probable J0512] [GN:YJL171c] [OR:*Saccharomyces cerevisiae*] [DB:pir2] [MP:10L] >gp:[GI:1008365] [LN:SCYJL171C] [AC:Z49446:Y13136] [OR:*Saccharomyces cerevisiae*] [SR:baker's yeast] [DB:genpept-pln5] [DE:*S. cerevisiae* chromosome X reading frame ORF YJL171c.] [NT:ORF YJL171c] [SP:P46992] [LE:237] [RE:1427] [DI:complement] |
| orf6.8067 | 189 | 399 | 801 | 266 | 354 | 1.20E-33 | gp:[GI:3393011] [LN:SAA224764] [AC:AJ224764] [PN:Clumping factor B] [GN:clfB] [FN:binds fibrinogen] [OR:*Staphylococcus aureus*] [DB:genpept-bct4] [DE:*Staphylococcus aureus* strain Newman clumping factor B (clfB) gene.] [LE:28] [RE:2769] [DI:direct] |

-continued

| ORF | NT Seq ID | AA Seq ID | NT ORF Length | AA ORF Length | Score | Probability | Description |
|---|---|---|---|---|---|---|---|
| orf6.8114 | 190 | 400 | 1509 | 502 | 906 | 5.30E-93 | sp:[LN:YBQ6_YEAST] [AC:P38081] [GN:YBR056W:YBR0510] [OR:*Saccharomyces cerevisiae*] [SR:,Baker's yeast] [DE:Hypothetical 57.8 kDa protein in PRP6-MUM2 intergenic region] [SP:P38081] [DB:swissprot] >pir:[LN:S45914] [AC:S45914:S49511:S55855] [PN:probable glucan 1,3-beta-glucosidase, YBR056w:hypothetical protein YBR0510] [OR:*Saccharomyces cerevisiae*] [EC:3.2.1.58] [DB:pir2] [MP:2R] >gp:[GI:559952] [LN:SCA10131] [AC:Z46260] [PN:putative protein] [OR:*Saccharomyces cerevisiae*] [SR:baker's yeast] [DB:genpept-pln4] [DE:*S. cerevisiae* alphaS288C DNA of remnant delta gene for ribosomalprotein S18.] [SP:P38081] [LE:15420] [RE:16925] [DI:direct] >gp:[GI:536293] [LN:SCYBR056W] [AC:Z35925:Y13134] [OR:*Saccharomyces cerevisiae*] [SSR:baker's yeast] [DB:genpept-pln4] [DE:*S. cerevisiae* chromosome II reading frame ORF YBR056w.] [NT:ORF YBR056w] [SP:P38081] [LE:578] [RE:2083] [DI:direct] |
| orf6.8118 | 191 | 401 | 816 | 271 | 492 | 6.00E-49 | sp:[LN:YKZ3_YEAST] [AC:P36110] [GN:YKR013W:YK111] [OR:*Saccharomyces cerevisiae*] [SR:,Baker's yeast] [DE:precursor] [SP:P36110] [DB:swissprot] [>pir:[LN:S38082] [AC:S38082] [PN:pathogenesis-related protein homolog YKR013w] [GN:PRY2] [OR:*Saccharomyces cerevisiae*] [DB:pir2] [MP:11R] >gp:[GI:486427] [LN:SCYKRO13W] [AC:Z28238:Y13137] [GN:PRY2] [OR:*Saccharomyces cerevisiae*] [SR:baker's yeast] [DB:genpept-pln5] [DE:*S. cerevisiae* chromosome XI reading frame ORF YKR013w.] [NT:ORF YKR013w] [SP:P36110] [LE:1] [RE:990] [DI:direct] |
| orf6.8151 | 192 | 402 | 1476 | 491 | 412 | 1.30E-40 | pir:[LN:T45525] [AC:T45525] [PN:WSC4 homolog [imported]] [GN:wsc4] [OR:*Kluyveromyces marxianus* var. *lactis:Candida sphaerica*] [DB:pir2] >gp:[GI:5531272] [LN:KLA243803] [AC:AJ243800] [PN:WSC4 homologue] [GN:wsc4] [OR:*Kluyveromyces lactis*] [DB:genpept-pln4] [DE:*Kluyveromyces lactis* rim101 (partial), wsc4, ubi4 and ecm29 (partial) genes.] [LE:2272] [RE:3612] [DI:complement] |
| orf6.8214 | 193 | 403 | 429 | 142 | 86 | 0.00044 | gp:[GI:15141575] [LN:AX181474] [AC:AX181474] [PN:olfactory receptor] [OR:*Eulemur rubriventer*] [SR:red-bellied lemur] [DB:genpept-pat2] [DE:Sequence 262 from Patent WO0146262.] [LE:>2] [RE:>487] [DI:direct] >gp:[GI:7211565] [LN:AF179784] [AC:AF179784] [PN:olfactory receptor] [GN:ERU160] [OR:*Eulemur rubriventer*] [SR:red-bellied lemur] [DB:genpept-pri9] [DE:*Eulemur rubriventer* olfactory receptor (ERU160) gene, partial cds.] [LE:<1] [RE:>487] [DI:direct] |
| orf6.8265 | 194 | 404 | 1671 | 556 | 950 | 2.50E-114 | sp:[LN:TRM1_YEAST] [AC:P15565:Q9URQ7:Q9URQ8] [GN:TRM1:YDR120C:YD9727.15C] [OR:*Saccharomyces cerevisiae*] [SR:Baker's yeast] [EC:2.1.1.32] [DE:(tRNA(m(2,2)G26)dimethyltransferase)] [SP:P15565:Q9URQ7:Q9URQ8] [DB:swissprot] >pir:[LN:A28323] [AC:A28323:S52685] [PN:N2,N2-dimethylguanine tRNA methyltransferase, [validated]:protein YD9727.15c:protein YDR120c] [GN:TRM1:YDR120c] [OR:*Saccharomyces cerevisiae*] [EC:2.1.1.—] [DB:pir2] [MP:4R] >gp:[GI:747894] [LN:SC9727] [AC:Z48758:Z71256] [PN:Trm1p] [GN:TRM1] [OR:*Saccharomyces cerevisiae*] [SR:baker's yeast] [DB:genpept-pln4] [DE:*S. cerevisiae* chromosome IV cosmid 9727.] [NT:YD9727.15c, TRM1 gene, len: 570, CAI: 0.16,] [SP:P15565] [LE:26338] [RE:28050] [DI:complement] >gp:[GI:172940] [LN:YSCTGM1] [AC:M17193] [OR:*Saccharomyces cerevisiae*] [SR:Yeast (*S. cerevisiae*) DNA] [DB:genpept-pln5] [DE:Yeast (*S. cerevisiae*) tRNA methyltransferase (TRM1) gene, complete cds.] [NT:tRNA dimethyltransferase] [LE:595] [RE:2307] 8 DI:direct] |
| orf6.8269 | 195 | 405 | 2343 | 780 | 3993 | 0 | gp:[GI:2274776] [LN:AB001077] [AC:AB001077] [PN:glucan synthase] [GN:GSL2] [OR:*Candida albicans*] [SR:*Candida albicans* DNA] [DB:genpept-pln1] [DE:*Candida albicans* GSL2 gene for glucan synthase, complete cds.] [LE:1] [RE:4923] [DI:direct] |
| orf6.8270 | 196 | 406 | 2595 | 864 | 4535 | 0 | gp:[GI:2274776] [LN:AB001077] [AC:AB001077] [PN:glucan synthase] [GN:GSL2] [OR:*Candida albicans*] [SR:*Candida albicans* DNA] [DB:genpept-pln 1] [DE:*Candida albicans* GSL2 gene for glucan synthase, complete cds.] [LE:1] [RE:4923] [DI:direct] |
| orf6.8379 | 197 | 407 | 3030 | 1009 | 5307 | 0 | sp:[LN:CHS2_CANAL] [AC:P30572] [GN:CHS2] [OR:*Candida albicans*] [SR:,Yeast] [EC:2.4.1.16] [DE:transferase 2)] [SP:P30572] [DB:swissprot] >gp:[GI:7687906] [LN:YSACS2A] [AC:M82937] [PN:chitin synthase 2] [GN:CHS2] [OR:*Candida albicans*] [DB:genpept-pln5 ] [DE:*Candida albicans* chitin synthase 2 (CHS2) gene, complete cds.] [LE:703] [RE:3732] [DI:direct] |
| orf6.8457 | 198 | 408 | 2931 | 976 | 321 | 1.00E-49 | pir:[LN:S64821] [AC:S64821:S64823:S70577] [PN:probable membrane protein YLR001c:hypothetical protein L1388] [CL:*Saccharomyces cerevisiae* probable membrane protein YLR001c] [OR:*Saccharomyces cerevisiae*] [DB:pir2] [MP:12R] >gp:[GI:1495225] [LN:SCCEN12RG] [AC:X91488] [PN:L1388 protein] [GN:L1388] [OR:*Saccharomyces cerevisiae*] [SR:baker's yeast] [DB:genpept-pln4] [DE:*S. cerevisiae* DNA from CEN12 region including ATS/APSG, SCD25, SOF1, DRS1, MMM1 and DNM1 genes.] [LE:40057] [RE:42645] [DI:complement] >gp:[GI:1360286] [LN:SCYLR001C] |

-continued

| ORF | NT Seq ID | AA Seq ID | NT ORF Length | AA ORF Length | Score | Probability | Description |
|---|---|---|---|---|---|---|---|
| orf6.848 | 199 | 409 | 1680 | 559 | 697 | 6.90E-71 | [AC:Z73173:Y13138] [OR:*Saccharomyces cerevisiae*] [SR:baker's yeast] [DB:genpept-pln5] [DE:*S. cerevisiae* chromosome XII reading frame ORF YLR001c.] [NT:ORF YLR001c] [LE:1226] [RE:3814] [DI:complement] sp:[LN:MID1__YEAST] [AC:P41821] [GN:MID1:YNL291C:N0530] [OR:*Saccharomyces cerevisiae*] [SR:,Baker's yeast] [DE:MID1 protein] [SP:P41821] [DB:swissprot] >:[LN:A56353] [AC:A56353:S60411:S63267:S63265:S50251] [PN:MID1 protein:protein NO530:protein YNL0530:protein YNL291c] [GN:MID1] [CL:*Saccharomyces cerevisiae* MID1 protein] [OR:*Saccharomyces cerevisiae*] [DB:pir2] [MP:14L] >gp:[GI:1050871] [LN:SCU23084] [PN:Mid1p] [GN:MID1] [OR:*Saccharomyces cerevisiae*] [SR:baker's yeast] [DB:genpept-pln4] [DE:*Saccharomyces cerevisiae* chromosome XIV, 30 Kb fragment.] [NT:plasma membrane protein; YNL0530; Ynl0530p] [LE:26645] [RE:28291] [DI:complement] >gp:[GI:1302377] [LN:SCYNL291C] [AC:Z71567:Y13139] [GN:MID1] [OR:*Saccharomyces cerevisiae*] [SR:baker's yeast] [DB:genpept-pln5] [DE:*S. cerevisiae* chromosome XIV reading frame ORF YNL291c.] [NT:ORF YNL291c] [SP:P41821] [LE:152] [RE:1798] [DI:complement] >gp [GI:601941] [LN:YSCMID1P] [AC:D32133] [PN:Mid1p] [GN:M1D1] [OR:*Saccharomyces cerevisiae*] [SR:*Saccharomyces cerevisiae* DNA] [DB:genpept-pln5] [DE:Yeast gene for Mid1p.] [LE:150] [RE:1796] [DI:direct] |
| orf6.8560 | 200 | 410 | 6003 | 2000 | 5583 | 0 | gp:[GI:9754771] [LN:AF201684] [AC:AF201684] [PN:agglutinin-like protein Als7p] [GN:ALS7] [OR:*Candida albicans*] [DB:genpept-pln2] [DE:*Candida albicans* agglutinin-like protein Als7p (ALS7) gene, complete cds.] [LE:1] [RE:6894] [DI:direct] |
| orf6.857 | 201 | 411 | 1548 | 515 | 1664 | 1.40E-173 | sp:[LN:HYR1__CANAL] [AC:P46591] [GN:HYR1] [OR:*Candida albicans*] [SR:,Yeast] [DE:Hyphally regulated protein precursor] [SP:P46591] [DB:swissprot] >gp:[GI:1052565] [LN:CAHYR1GN] [AC:Z50123] [PN:hyphally regulated protein] [GN:HYR1] [FN:unknown] [OR:*Candida albicans*] [DB:genpept-pln4] [DE:*Candida albicans* HYR1 gene and promoter region.] [SP:P46591] [LE:1890] [RE:4703] [DI:direct] |
| orf6.8574 | 202 | 412 | 4101 | 1366 | 4527 | 0 | gp:[GI:5326752] [LN:AF075293] [AC:AF075293] [PN:agglutinin-like protein 6] [GN:ALS6] [OR:*Candida albicans*] [DB:genpept-pln2] [DE:*Candida albicans* strain 1161 agglutinin-like protein 6 (ALS6) gene, complete cds.] [LE:1] [RE:4332] [DI:direct] |
| orf6.8620 | 203 | 413 | 3318 | 1105 | 2179 | 3.40E-228 | sp:[LN:CHS2__CANAL] [AC:P30572] [GN:CHS2] [OR:*Candida albicans*] [SR:,Yeast] [EC:2.4.1.16] [DE:transferase 2)] [SP:P30572] [DB:swissprot] >gp:[GI:7687906] [LN:YSACS2A] [AC:M82937] [PN:chitin synthase 2] [GN:CHS2] [OR:*Candida albicans*] [DB:genpept-pln5] [DE:*Candida albicans* chitin synthase 2 (CHS2) gene, complete cds.] [LE:703] [RE:3732] [DI:direct] |
| orf6.8635 | 204 | 414 | 1536 | 511 | 458 | 8.10E-45 | sp:[LN:HYR1__CANAL] [AC:P46591] [GN:HYR1] [OR:*Candida albicans*] [SR:,Yeast] [DE:Hyphally regulated protein precursor] [SP:P46591] [DB:swissprot] >gp:[GI:1052565] [LN:CAHYR1GN] [AC:Z50123] [PN:hyphally regulated protein] [GN:HYR1] [FN:unknown] [OR:*Candida albicans*] [DB:genpept-pln4] [DE:*Candida albicans* HYR1 gene and promoter region.] [SP:P46591] [LE:1890] [RE:4703] [DI:direct] |
| orf6.8640 | 205 | 415 | 1692 | 563 | 455 | 6.20E-47 | sp:[LN:HYR1__CANAL] [AC:P46591] [GN:HYR1] [OR:*Candida albicans*] [SR:,Yeast] [DE:Hyphally regulated protein precursor] [SP:P46591] [DB:swissprot] >gp:[GI:1052565] [LN:CAHYR1GN] [AC:Z50123] [PN:hyphally regulated protein] [GN:HYR1] [FN:unknown] [OR:*Candida albicans*] [DB:genpept-pln4] [DE:*Candida albicans* HYR1 gene and promoter region.] [SP:P46591] [LE:1890] [RE:4703] [DI:direct] |
| orf6.8724 | 206 | 416 | 4581 | 1526 | 793 | 3.60E-80 | sp:[LN:HYR1__CANAL] [AC:P46591] [GN:HYR1] [OR:*Candida albicans*] [SR:Yeast] [DE:Hyphally regulated protein precursor] [SP:P46591] [DB:swissprot] >gp:[GI:1052565] [LN:CAHYR1GN] [AC:Z50123] [PN:hyphally regulated protein] [GN:HYR1] [FN:unknown] [OR:*Candida albicans*] [DB:genpept-pln4] [DE:*Candida albicans* HYR1 gene and promoter region.] [SP:P46591] [LE:1890] [RE:4703] [DI:direct] |
| orf6.8725 | 207 | 417 | 2274 | 757 | 230 | 5.60E-18 | pir:[LN:S67694] [AC:S67694] [PN:probable membrane protein YDL146w:hypothetical protein D1575] [GN:YDL146w] [OR:*Saccharomyces cerevisiae*] [DB:pir2] [MP:4L] >gp:[GI:1321958] [LN:SCIV23] [AC:X97751] [OR:*Saccharomyces cerevisiae*] [SR:baker's yeast] [DB:genpept-pln4] [DE:*S. cerevisiae* chrIV genes STE7, CLB3, MSH5, RPC53, RET1.] [NT:D1575] [LE:20062] [RE:21537] [DI:direct] >gp:[GI:1431229] [LN:SCYDL146W] [AC:Z74194:Z71256] [OR:*Saccharomyces cerevisiae*] [SR:baker's yeast] [DB:genpept-pln4] [DE:*S. cerevisiae* chromosome IV reading frame ORF YDL146w.] [NT:ORF YDL146w] [LE:489] [RE:1964] [DI:direct] |
| orf6.8769 | 208 | 418 | 1389 | 462 | 2392 | 2.00E-250 | gp:[GI:15530178] [LN:CAU36490] [AC:U36490] [PN:chitinase] [GN:CHT1] [OR:*Candida albicans*] [DB:genpept-pln4] [DE:*Candida albicans* chitinase (CHT1) gene, complete cds.] [LE:444] [RE:1832] [DI:direct] |
| orf6.9090 | 209 | 419 | 5520 | 1839 | 3643 | 0 | gp:[GI:13811667] [LN:AF356651] [AC:AF356651] [PN:Sec7p] [GN:SEC7] [OR:*Pichia pastoris*] [DB:genpept-pln2] [DE:*Pichia pastoris* Sec7p (SEC7) gene, complete cds.] [LE:1343] [RE:6661] [DI:direct] |

-continued

| ORF | NT Seq ID | AA Seq ID | NT ORF Length | AA ORF Length | Score | Probability | Description |
|---|---|---|---|---|---|---|---|
| orf6.6934 | 210 | 420 | 900 | 300 | 1612 | 3.00E-165 | sp:[LN:PRA1_CANAL] [AC:P87020:P78598] [GN:PRA1:FBP1] [OR:*Candida albicans*] [SR:,Yeast] [DE:mannoprotein)] [SP:P87020:P78598] [DB:swissprot] >gp:[GI:1916852] [LN:CAU84261] [AC:U84261] [PN:pH-regulated antigen] [GN:PRA1] [OR:*Candida albicans*] [SR:*Candida albican*] [DB:genpept-pln4] [DE:*Candida albicans* pH-regulated antigen (PRA1) gene, complete cds.] [LE:569] [RE:1468] [DI:direct] |

Example 2

Biological Characterization of Six Protein Targets Among the 210 Candidates

Among the 210 protein targets that fulfilled the bioinformatics criteria, we selected a subset of 6 proteins for biological characterization: MP65, PRA1, SAP9, 6.1231, 6.1639 and 6.3873 (named CSF for cell surface factor; see Table 6). The protein names are listed in the first column of Table 6. The second column contains an internal name designation (CSF1-6). The Genbank Accession number, when available, is in the third column. The fourth column contains the protein length in amino acids. Prediction of GPI anchor motif at the C-terminal of the protein, a good indication for cell surface protein, is indicated in the fifth column. The serine/threonine (ST) and cysteine contents are in the sixth and seventh columns, respectively. The ST content is represented in percent of total amino acids present in the polypeptide. The cysteine content is represented in the number of cysteine residues present over the entire protein. Preferred polypeptides contain eight or more cysteine residues. For a discussion on the relevance of cysteine rich domains, see for examples, Molloy et al., 1995 *Exp. Mycol.* 19: 178-85; Shen et al., 2001 *J. Biol. Chem.* 276: 15768-75; Wojtaszek et al., 1997 *FEBS Lett.* 405: 95-8; and Thompson et al., 1970 *J. Microsc.* 91: 87-98. Column 8 contains information about the signal peptide. A predicted transmembrane domain (TM) is indicated in the ninth column. The program PSORT2 was used to predict GPI anchor motifs, signal peptides and TM domains.

MP65 and PRA1 are two cell surface proteins that are predicted to have a role in the host-parasite interaction during candidal infection (Gomez, Infect Immun, 1996, 64, 2577-84, Gomez, Infect Immun, 2000, 68, 694-701, La Valle, Infect Immun, 2000, 68, 6777-84, Nisini, Infect Immun, 2001, 69, 3728-36, Sentandreu, J Bacteriol, 1998, 180, 282-9). Therefore, targeting antibodies or drugs against these two major antigens would result in a decrease in adherence to host tissue and most probably to a decrease in virulence. In addition to its role in cell-cell interaction, PRA1 is involved in the yeast-to-hyphal transition, which is critical for virulence of *C. albicans*. Inhibition of the protein function by a small molecule could then result in the alteration of hyphal formation and consequently affect virulence. The presence of cell surface proteins, such as MP65 and PRA1 in the list of 210 candidates supports our bioinformatics search procedure for *C. albicans* cell surface proteins.

Another protein, SAP9 is a member of the secreted aspartyl proteinase family, a group of enzymes that are involved in colonization, penetration and invasion by *C. albicans* (De Bernardis, Med Mycol, 2001, 39, 303-13, Stewart and Abad-Zapatero, Curr Med Chem, 2001, 8, 941-8, Hube, Curr Top Med Mycol, 1996, 7, 55-69). Similar to aspartyl proteinases that have been already characterized in *Candida*, SAP9 can be localized to the fungal cell surface, thereby accessible to antibodies or drugs (Borg and Ruchel, Infect Immun, 1988, 56, 626-31).

Figure 3:
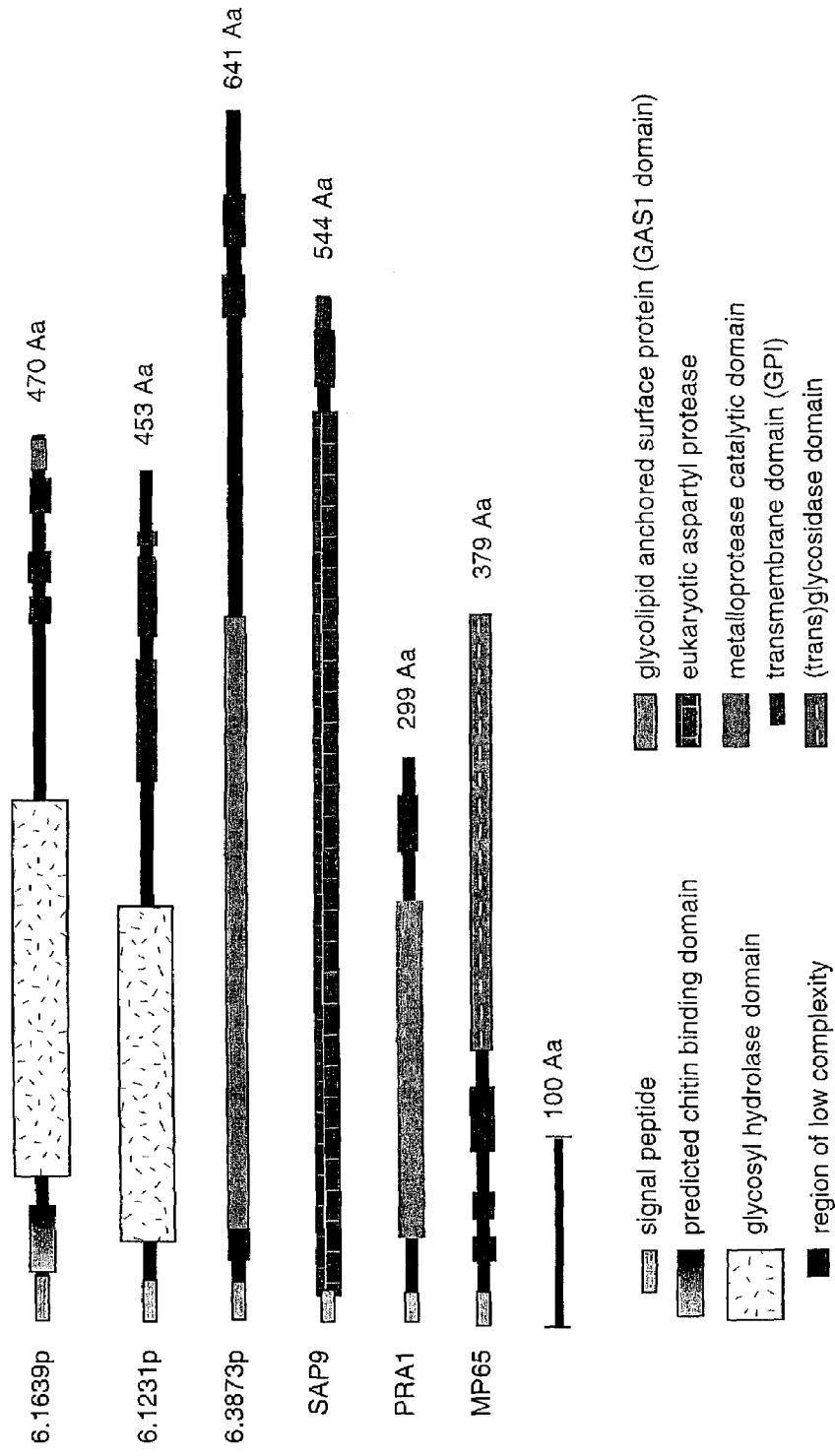
FIG. 3. Domain composition of *C. albicans* CSF proteins. The six primary sequences are drawn to scale. The protein length in amino acid is indicated on the right.

6.1231 and 6.1639 are two novel proteins that show significant sequence identity (~45% identity) to *S. cerevisiae* CRH1 and CRH2, two cell wall proteins that contribute to cell wall integrity and maintenance (Rodriguez-Pena, Mol Cell Biol, 2000, 20, 3245-55). In addition to its glycosyl hydrolase domain, 6.1639 contains a chitin binding domain located immediately after the signal peptide (FIG. 3). This indicates a potential role for 6.1639 in the recognition or binding of chitin subunits, a result that agrees with a cell wall localization. In addition, 6.1231 was found to be 51% identical to a known *A. fumigatus* allergen (Asp f9—Genbank #CAA11266.1—(Crameri, Int Arch Allergy Immunol, 1998, 115, 99-114, Banerjee, Clin Exp Allergy, 2001, 31, 761-70)) suggesting that 6.1231 may also be a major *C. albicans* allergen with a role in the host-parasite interaction. A hit for the same allergen was also found with 6.1639. Thus development of antibodies against these two novel proteins, 6.1639 or 6.1231, would be useful for diagnosis and could be used as a therapy to block fungal infection and facilitate clearance by the host immune system. Development of small drugs that modulate these proteins would be also beneficial.

TABLE 6

| Proteins | CSF | Genbank annotation | Size (Aa) | Gpi* | Ser-Thr residues (% of total Aa) | Cysteines | Signal peptides* | TM* | SEQ ID NO: |
|---|---|---|---|---|---|---|---|---|---|
| MP65 | 1 | CAC19886.1 | 379 | 0 | 20.58 | 6 | predicted | 0 | |
| PRA1 | 2 | AAC00525.1 | 299 | 0 | 19.06 | 9 | predicted | 0 | |
| SAP9 | 3 | AAC69996.1 | 544 | 1 | 22.06 | 4 | predicted | 1 | |
| 6.1639 | 4 | Novel | 470 | 1 | 22.77 | 9 | predicted | 1 | |
| 6.1231 | 5 | Novel | 453 | 0 | 29.36 | 2 | predicted | 0 | |
| 6.3873 | 6 | Novel | 641 | 0 | 13.73 | 20 | predicted | 1 | |

*predicted by the PSORT2 program based on McGeoch's (McGeoch, Virus Res, 1985, 3, 271–86) and Heijne's methods (Heijne, Nucl. Acids Res. 1986, 14:4683)

The protein, 6.3873 shows significant sequence identity (40%) with *Aspergillus fumigatus* Gel3p (Mouyna, Biochem J, 2000, 347 Pt 3, 741-7), a glycosylphosphatidylinositol-anchored glucanosyltransferase that is predicted to be localized to the fungal cell wall. It also shows similarity with *C. glabrata* GAS3p (50%) (Weig, Microbiology,. 2001, 147, 2007-19) and *C. dubliensis* PHR2p (40%) (Heinz, Int J Med Microbiol, 2000, 290, 231-8). Therefore targeting Orf 6.3873 by antibodies or small drugs would be useful not only in the treatment of *Candida* spp. infections, but also in the treatment of other serious fungal infections, such as Aspergillosis.

All six CSF genes including the three novel genes, 6.1639, 6.1231 and 6.3873, were shown to be expressed by RT-PCR using primers internal to the ORFs, indicating that they are all real genes. We further investigated the role of each CSF gene in fungal cell wall biosynthesis, adhesion to mammalian cells and virulence.

A. Strains and Growth Conditions

The *C. albicans* strains used in this study are listed in Table 7. Column 1 contains the names of the strains and column 2 indicates the source of each strain. The designation "this study" means that the strain was created during the present study. The relevant genotype or phenotype of the strains is listed in the last column. *C. albicans* strains were routinely grown in rich YEPD medium (2% glucose, 1% yeast extract, 2% bacto-peptone) or minimal CSM medium (0.67% yeast nitrogen base without amino acids, 2% glucose) supplemented with 2.5 mg/l uridine when necessary. *C. albicans* primary transformants were selected at 30° C. on CSM –arg +uridine plates on the basis of the integration of the ARG marker at the locus of interest. Secondary transformants were selected on CSM –arg –ura plates for the integration of the URA marker, replacing the second allele of the gene of interest.

B. Gene Expression:

Gene expression was confirmed by RT-PCR using the Invitrogen SUPERSCRIPT™ One-Step RT-PCR System for Long Templates (Cat. No. 11922-010). PCR mixtures contain 12.5 µl of 2× Reaction mix, 1 µl (~400 ng) of template RNA, 1 µl of each primer (10 µM), 1 µl of RT/Taq enzyme and 8.5 µl of DEPC-treated water. Reverse transcription was performed at 50° C. for 30 min. followed by a denaturation step of 2 min. at 94° C. PCR amplification consisted of 35 cycles of 94° C. for 30 seconds, 54° C. for 30 seconds, 68° C. for 2 min. A final extension at 68° C. for 5 min. followed by 4° C. incubation ended the PCR. Any possible DNA contamination was verified by PCR using RNA as template and Taq polymerase as enzyme (Invitrogen SuperMix).

C. Construction of *Candida albicans* Null Mutants

Figure 4A:
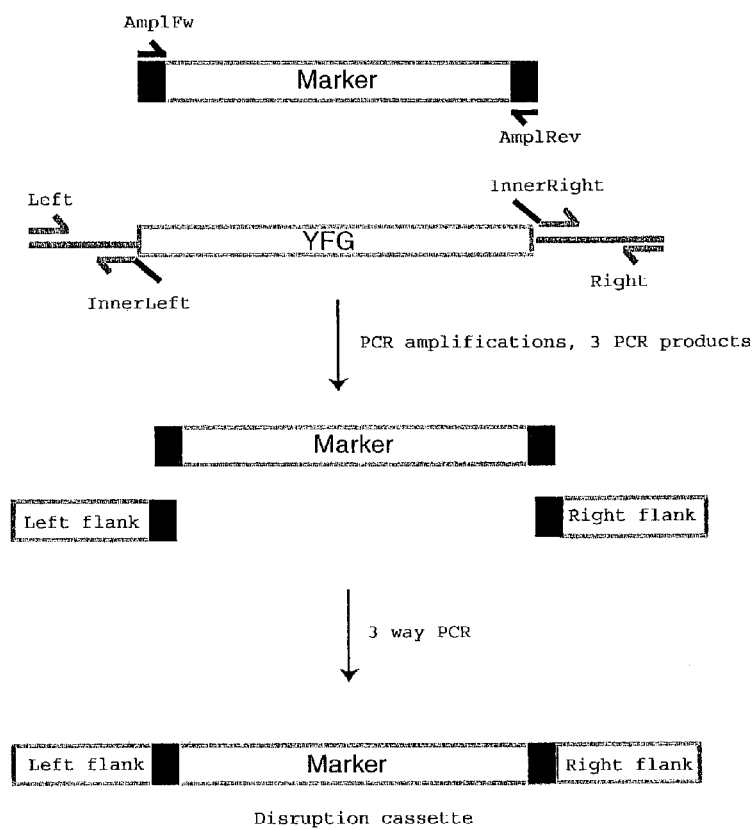
FIGS. 4A-C. Construction of *C. albicans* null mutants. A. Generation of the disruption cassette by 3-way PCR. To generate a fragment containing the marker gene flanked by upstream and downstream sequences of the gene of interest, the three PCR pieces (left and right fragments and the marker gene) were used as templates in a final PCR reaction with only the two outermost left and right primers. B. Gene disruption method. The genomic locus of the targeted gene is shown before and after replacement of the first and second alleles by the ARG4 and URA3 marker respectively. Verification primers (A, D, I, J, G, H, K and L) are positioned according to the sequences they are homologous to. Genomic sequences targeted in the first or second deletions are indicated in light gray or dark gray boxes respectively. C. verification PCR on mp65 null mutants. I and J primers internal to the MP65 ORF were used to indicate the presence of the wild-type gene. We included in the same reaction the I and J primers of another gene (ORFX) as control. As indicated (lane1), no PCR product (~550 bp) corresponding to the IJ amplification of MP65 was obtained indicating that the MP65 ORF has been deleted. Correct integration of the ARG4 marker was checked by combining primers A, G, H and D in the same reaction (lane2). Replacement of the second allele of MP65 was verified using the two following combinations of primers: A/K (lane3), and D/L (lane4).
Figure 4B:
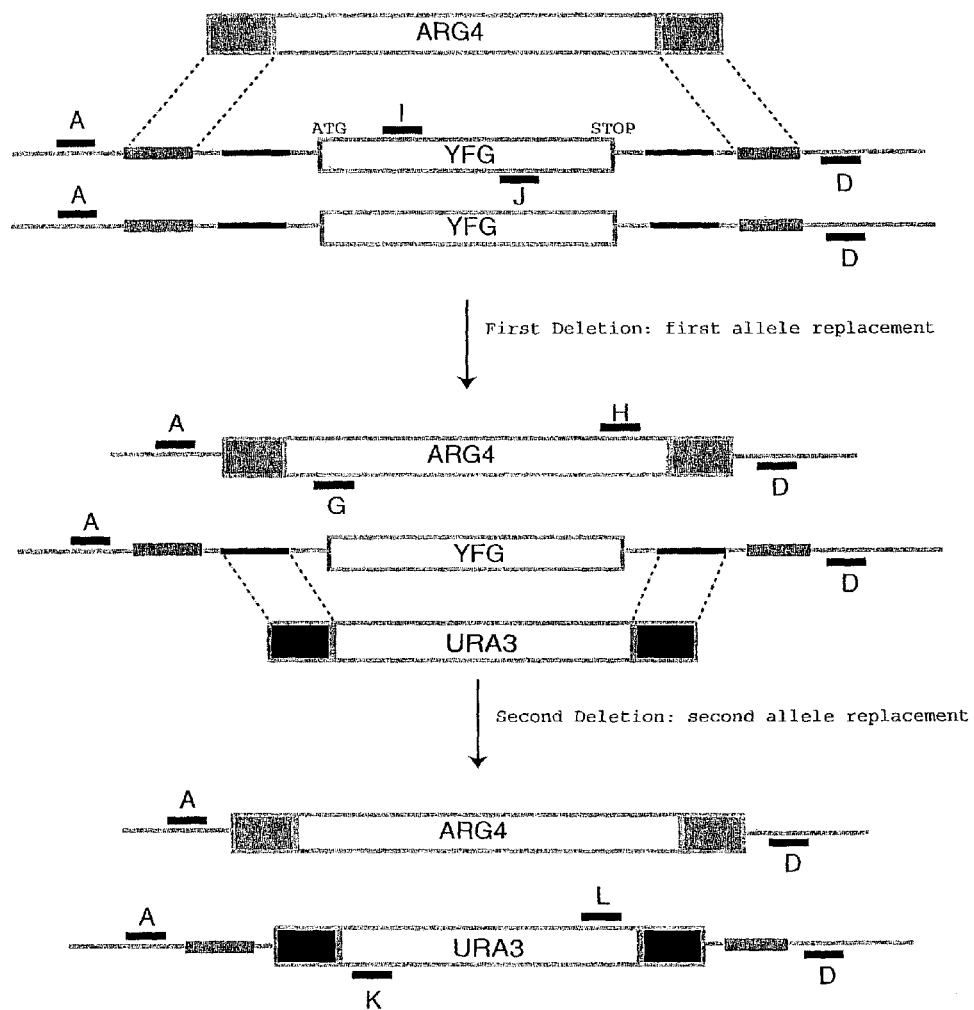

In an attempt to investigate the role of the potential protein targets in cell wall biosynthesis, adherence and virulence, we deleted for each particular gene of interest both alleles using a one step (Cruz, Embo J, 2002, 21, 546-59, Enloe, J Bacteriol, 2000, 182, 5730-6) or a two steps (Willins, Gene, 2002, 292, 141-9) gene disruption methods as described below. Correct integration of the two markers as well as the absence of the wild-type gene in the final homozygote null mutant was checked by PCR. The als1Δ, hwp1Δ and csf1-5 mutants were generated using an adapted version of the 3-way PCR based technique recently described to delete genes in *C. glabrata* (Willins, Gene, 2002, 292, 141-9). The disruption method is presented FIGS. 4A and 4B. Briefly, two deletion cassettes consisting of the *C. albicans* ARG4 or URA3 markers flanked by 300-400 bp of homology to the gene of interest were used to delete sequentially both alleles. Each deletion cassette was generated by 3-way PCR using the following three PCR pieces: 1) a fragment consisting of 300-400 base segment

TABLE 7

| Strains | Source of strains | Relevant genotype or phenotype |
|---|---|---|
| SC5314 clinical isolate | Parental strain of CAI4 (Bhattacherhee et al, Med. Mycol. 37:411–417, 1999) | Wild-type, pathogenic strain |
| CAI4 | derived from strain SC5314 | ura3Δ::λimm434/ura3Δ::λimm434 |
| BWP17 | derived from CAI4 | ura3Δ::λimm434 his1::hisG arg4::hisGlura3Δ::λimm434 his1::hisG arg4::hisG |
| BWP17 ARG/HisCIp | This study | ura3Δ::λimm434 his1::hisG ARG4 lura3Δ::λimm434 his1::hisG arg4::hisG, RP10/rp10::URA3-HIS1 |
| als1Δ | This study | ura3Δ::λimm434 his1::hisG arg4::hisGlura3Δ::λimm434 his1::hisG arg4::hisG, als1Δ::ARG4/als1Δ::URA3 RP10/rp10:: URA3-HIS1 |
| hwp1Δ | This study | ura3Δ::λimm434 his1::hisG arg4::hisGlura3Δ::λimm434 his1::hisG arg4::hisG, hwp1Δ::ARG4/hwp1Δ::URA3 RP10/rp10:: URA3-HIS1 |
| Csf1Δ | This study | ura3Δ::λimm434 his1::hisG arg4::hisGlura3Δ::λimm434 his1::hisG arg4::hisG, mp65Δ::ARG4/mp65Δ::URA3 RP10/rp10:: URA3-HIS1 |
| Csf2Δ | This study | ura3Δ::λimm434 his1::hisG arg4::hisG/ura3Δ::λimm434 his1::hisG arg4::hisG, pra1Δ::ARG4/pra1Δ::URA3 RP10/rp10:: URA3-HIS1 |
| Csf3Δ | This study | ura3Δ::λimm434 his1::hisG arg4::hisG/ura3Δ::λimm434 his1::hisG arg4::hisG, sap9Δ::ARG4/sap9Δ::URA3 RP10/rp10:: URA3-HIS1 |
| Csf4Δ | This study | ura3Δ::λimm434 his1::hisG arg4::hisG/ura3Δ::λimm434 his1::hisG arg4::hisG, 6.1639Δ::ARG4/6.1639Δ::URA3 RP10/rp10:: URA3-HIS1 |
| Csf5Δ | This study | ura3Δ::λimm434 his1::hisG arg4::hisG/ura3Δ::λimm434 his1::hisG arg4::hisG, 6.1231Δ::ARG4/6.1231Δ::URA3 RP10/rp10:: URA3-HIS1 |
| Csf6Δ | This study | ura3Δ::λimm434 his1::hisG arg4::hisG/ura3Δ::λimm434 his1::hisG arg4::hisG, 6.3873Δ::ARG4/6.3873Δ::URA3 RP10/rp10:: URA3-HIS1 | derived from the region upstream of the gene of interest, with an additional 24 base segment of homology to the 5' end of the ARG4 or URA3 marker (=Left fragment); 2) the marker gene (including its native transcriptional promoter and terminator sequences), 3) a fragment containing a short 24 base segment homologous to the 3' end of the ARG4 or URA3 marker followed by 300-400 bp sequence with homology to region downstream of the gene of interest (=Right fragment). The 300-400 region of homology were chosen ~1 kb upstream and downstream of the ORF of interest for the first ARG4 deletion. For the second URA3 deletion the homology regions were chosen within the region that has been deleted during the first allele replacement to ensure proper disruption of the second allele.

The three pieces indicated in the previous paragraph were generated by PCR with *C. albicans* genomic DNA from strain CAI4 and the appropriate primers, with the exception of the URA3 marker that was amplified from *C. albicans* ATCC90029 genomic DNA. PCR amplification was performed in a 50 μl reaction with 0.3 μM of each primer and approximately 100 ng of genomic DNA template using PCR SuperMix High Fidelity enzyme or eLONGaseR enzyme (Gibco-BRL Life Technologies). PCR conditions were as follows or a similar set of conditions: 95° C. for 2 min., 25 cycles of 95° C. for 30 seconds, 54° C. for 30 seconds, 68° C. for 2 min. The 25 cycles were ended by a final extension at 68° C. for 5 min. followed by a 4° C. incubation. The three fragments were optionally purified and concentrated by ethanol precipitation, the QIAquick™ DNA Cleanup System (QIAGEN), or gel purification. To generate a fragment containing the marker gene flanked by upstream and downstream segments of the gene of interest, the three fragments were used as templates in a final PCR reaction with only the two outermost primers. The following conditions were used: 1) 92° C. for 2 min., 2) 9 cycles of 92° C. for 30 seconds, 50° C. for 30 seconds, 68° C. for 5 min., 3) 19 cycles of 92° C. for 30 seconds, 50° C. for 30 seconds, 68° C. for 5 min. with a time increment of 20 seconds per cycle, and 4) 68° C. for 15 min. The 3-way PCR products were concentrated by ethanol precipitation and 20-30 μg was used to transform *C. albicans* strains. After each transformation step, correct integration of the marker was checked by PCR on genomic DNA. Alternatively, transformants were tested directly by colony PCR (Steffan et al., 1997 *Clin. Microbiol.* 35: 2031-9). The absence of the wild-type gene in the secondary transformant was confirmed by PCR using two primers internal to the gene. All primers used for gene disruption and analytical PCR are listed in Table 8. The first column of Table 8 contains the markers and the gene names (according to the Stanford genome annotation www-sequence.stanford-.edu/group/candida). The forward and reverse primers (AmplFw and AmplRev, respectively) that were used to amplify the markers as well as the four primers (Left, IL, IR and Right) used to generate the disruption cassettes are listed in the second column. The analytical primers A, D, I, J that were used to verify the correct integration of the marker are also reviewed. Primer sequences homologous to the marker are underlined.

The csf6 strain was created using the UAU1 transformation protocol (Cruz, Embo J, 2002, 21, 546-59, Enloe, J Bacteriol, 2000, 182, 5730-6) with the following modifications: the UAU1 cassette was amplified and transformed into *C. albicans* BWP17 strain. Arg+ transformants were selected on CSM –arg +uri plates. Transformants with correct integration were then grown in 5 ml YPD overnight. After 16 hours incubation at 30° C. cells were centrifuged, resuspended in 1 ml H20 and spread on CSM –arg –ura selective plates. Thirty Arg+ Ura+ colonies were picked and screened by PCR. Primers used for the amplification of the UAU1 cassette (UAU1Left and UAU1Right primers) as well as verification primers are listed in Table 8.

To ensure that the expression of the URA3 marker in the final homozygote strain is independent of its position and will not produce spurious effects by itself, we targeted the URA3 marker to the RP10 locus. First, we constructed a HIS-CIp10 plasmid by cloning *C. albicans* HIS1 gene at the ClaI site of the integrating vector CIp10 (Murad, Yeast, 2000, 16, 325-7). The resulting HIS-CIp10 plasmid was linearized with StuI and transformed into each null mutant using standard yeast transformation procedure. Integration of HIS-CIp10 at the RP10 locus was verified by PCR.

*C. albicans* null mutants that show correct integration of all three markers and lack the wild-type gene of interest were selected for further investigations.

TABLE 8

| Markers | Primers |
| --- | --- |
| CaARG4 | Amplification primers |
| | AmplFw:cccctttagtaagatttttcaagag<br>AmplRev:gttccttattcttgaaagctgctg<br>Analytical primers |
| | G: ctcttgaaaaatcttactaaagggg<br>H: ggatatgttggctactgatttagc |
| CaURA3 | Amplification primers |
| | AmplFw:ggaattgatttggatggtataaacggaaacaa<br>AmplRev:tgatttctagaaggaccacctttgattg<br>Analytical primers |
| | K: ctataggtcttagtgttgactgtcat<br>L: ggtatagagatgctggttggaatg |
| Genes (Stanford annotation) | Primers |
| Als1 | First Deletion |
| | LeftARG: cactaaagttgctgcaactgaagg<br>ILARG: <u>ctcttgaaaaatcttactaaagggg</u>caaagtcaatcagacccatatc<br>IRARG: <u>ctagtgttataatgtttataacagcagcttt</u>caagaataaggaacggacaacttttagacacacggaattgc<br>RightARG: ttggtagcgcagttctgatcagtg |

TABLE 8-continued

| Markers | Primers |
|---|---|
| | Second Deletion<br><br>LeftURA: cggagaagtaagacagcac<br>ILURA: ccagctcttttttttgtttccgtttataccatccaaatcaattccggtagttgtttgaacaattctg<br>IRURA: gtggtaattattactatttacaatcaaaggtggtccttctagaaatcaggcttgatctagttcacat<br>RightURA: cctgcttccgcataagttgttcaac<br>Analytical primers<br><br>PrimerA: caccaaaccatacgtatatttagt<br>PrimerD: tctggaaagtgttcctatttattctga<br>PrimerI: gccgatggtgttaaatatgc<br>PrimerJ: ggcataactctggaagcatac |
| HWP1 | First deletion<br><br>LeftARG: ctgaattatcagtccactaattcc<br>ILARG: ctcttgaaaaatcttactaaaggggccgaattccttgtttttggatcc<br>IRARG: ctagtgttataatgtttataacagcagctttcaagaataaggaacctgttttcggttcatagttgatagc<br>RightARG: cagctttacacgaccatacagattctac<br>Second Deletion<br><br>LeftURA: gggagagttttggtaggctcataatcg<br>ILURA: *ccagctcttttttttgtttccgtttataccatccaaatcaattcc*aagcgagtgactataggagattcctg<br>IRURA: *gtggtaattattactatttacaatcaaaggtggtccttctagaaatc*agtgaaacctcaccaattgctccag<br>RightURA: cctttaatgtagtaaac<br>Analytical primers<br><br>PrimerA: ggaaatccctctcacagtgaactgaattatccatctg<br>PrimerD: atcttttattgcggctgatcctcc<br>PrimerI: ctgctcaacttattgctatcgc<br>PrimerJ: ggagtagtttcagtcaatggacag |
| SAP9 | First deletion<br><br>LeftARG: caacagttatcttagatcaagatcgtgga<br>ILARG: ctcttgaaaaatcttactaaagggggaaaaacaaaagcaatagtacaattaatc<br>IRARG: ctagtgttataatgtttataacagcagctttcaagaataaggaacccaagagacacaatatgtaattatct<br>RightARG: atggggcacgggatcaaagac<br>Second Deletion<br><br>LeftURA: agtagtaaatggatttcccaaatttc<br>ILURA: ccagctcttttttttgtttccgtttataccatccaaatcaattccaaaaagaaaagaaatcagatg<br>IRURA: gtggtaattattactatttacaatcaaaggtggtccttctagaaatcaggttgttgcttcgcttttgatatc<br>RightURA: atacgaacgcagtatcctagctac<br>Analytical primers<br><br>PrimerA: ggtgactttccgatcattcaaaga<br>PrimerD: cgaatcaattattcgggaactag<br>PrimerI: ccccctgaagatgattccaatcc<br>PrimerJ: gcatcggcagtattgagatataagg |
| PRA1 | First deletion<br><br>LeftARG: GTATTGGTTGGAACTGGCAAGATTG<br>ILARG: ctcttgaaaaatcttactaaaggggGTGTTGAGTTCTCTTGGCGACCGATGG<br>IRARG: ctagtgttataatgtttataacagcagctttcaagaataaggaacCAGGACAACCGACAAAGCCTCTC<br>RightARG: GTCAAGTCAAAGATAGTAATGGGC<br>Second Deletion<br><br>LeftURA: CTTCATGGATCAGTATTCCGAAC<br>ILURA: ccagctcttttttttgtttccgtttataccatccaaatcaattccTAAAAAAAATGATTAACCAAAC<br>IRURA: gtggtaattattactatttacaatcaaaggtggtccttctagaaatcaGCTAACCTGCATTGCCACAC<br>RightURA: CTCTTTTGTCTACATACGATTTTGC<br>Analytical primers<br><br>PrimerA: GAGCTCGACTCTTCATCATCTTC<br>PrimerD: CAACAAGGTCAACTGTGAATC<br>PrimerI: CCGATTGATCTGTCGTGTAATGC<br>PrimerJ: GAGCCAATTCAAGAACCTCCTC |
| MP65 | First deletion<br><br>LeftARG: ACCTATAATCTTGCTTATCTAGCTTTGTTG<br>ILARG: ctcttgaaaaatcttactaaaggggATTATTATTACGCAAAGAAAG<br>IRARG: ctagtgttataatgtttataacagcagctttcaagaataaggaacCACTTCAAACAAACAATAAAC<br>RightARG: GCAATAGTATTAGTGCGAAATTCGTC |

TABLE 8-continued

| Markers | Primers |
|---|---|
| | Second Deletion<br><br>LeftURA: CAAAGTAGGTAGTAGGTATCAC<br>ILURA: ccagctcttttttttgtttccgtttataccatccaaatcaattccCTTTGGAAGGCCGATGGTCC<br>IRURA: gtggtaattattactatttacaatcaaaggtggtccttctagaaatcaAGCTAATGGAGCAGCCAAAGC<br>RightURA: CAAAGTTATATTCTATCAGTCTTTCCTTACA<br>Analytical primers<br><br>PrimerA: GGTGTAGAAGAACAAGCGTGTG<br>PrimerD: GCAGCAACAACAACCTATCACT<br>PrimerI: GCAAGACCCAAGCACCAGAGTTT<br>PrimerJ: GGTTCTGAACCTTCTGGTGGTGTTGG |
| ORF6.1639 | First deletion<br><br>LeftARG: tcttccacttcaagacaaatcaaatcc<br>ILARG: ctcttgaaaaatcttactaaaggggaatataaataaataaaaaaattttaaga<br>IRARG: ctagtgttataatgtttataacagcagctttcaagaataaggaaccgacctgacctgtaattattttc<br>RightARG: aaaggcaacacctttagccctagaag<br>Second Deletion<br><br>LeftURA: cttgtcttttcccttttttattg<br>ILURA: ccagctcttttttttgtttccgtttataccatccaaatcaattccgtatcgaatgtgcttgcgatatg<br>IRURA: gtggtaattattactatttacaatcaaaggtggtccttctagaaatcacttccatttgcttgggtatattatc<br>RightURA: acttccttataaggagcacaacttac<br>Analytical primers<br><br>PrimerA: ggttacccatacactacttgacttac<br>PrimerD: ggttgagttggatggaaatcaac<br>PrimerI: cctgaagataaaccatgctgttctc<br>PrimerJ: gcccattcaatagtaccttagca |
| ORF6.1231 | First deletion<br><br>LeftARG: aaccgattttttggtgtaacacaaag<br>ILARG: ctcttgaaaaatcttactaaaggggggtgtttatgtatgtgcggttttg<br>IRARG: ctagtgttataatgtttataacagcagctttcaagaataaggaactgattggaccaaagatgcagt<br>RightARG: gtattgtttgcctgaagaataatcagc<br>Second Deletion<br><br>LeftURA: tgatcttgttcagttccttctttc<br>ILURA: ccagctcttttttttgtttccgtttataccatccaaatcaattcctctattattattatttatttattttttgc<br>IRURA: gtggtaattattactatttacaatcaaaggtggtccttctagaaatcaaaagaagcaaggtactattg<br>RightURA: tataccttaccttctgccccc<br>Analytical primers<br><br>PrimerA: cacaacacagtgtgtgaccacc<br>PrimerD: gtaacaaacgtataatcattttcctc<br>PrimerI: gctgctaatgctaatgctgacacatg<br>PrimerJ: ggattgccattggtatggatcacc |
| ORF6.3873 | Deletion<br><br>UAU1LeftPrimer: gcaacaatcaactttactactccttttttttttttaattaaccgccaacaacaaccaccaccGTGGAATTGTGAGCGGATA<br>UAU1RightPrimer: gggagtaggctaagatttatttaaatcaatatagcagcagaacatgtaaataagatttcaTTTCCCAGTCACGACGTT<br>Analytical primers<br><br>PrimerA: gctctgttatggtgttgattggtt<br>PrimerD: ggattaacgaataagcataaggat<br>PrimerI: caccattattgatgacgataacaac<br>PrimerJ: gccaatacataaatccccgcttc |

D. Filamentation Assays

To determine the effect of gene disruption on the yeast-to-hyphal transition, we induced filamentation on solid media and checked for germ tube and hyphae formation. The assays were performed on Spider medium (1% w/v nutrient broth, 0.2% w/v $K_2HPO_4$, 1% w/v mannitol, 2% agar) at 37° C. The yeast to hyphal transition was also tested in liquid by growing the cells at 37° C. in RPMI medium 1640 (GIBCO Cell Culture) supplemented with 10% serum.

E. Sensitivities to Calcofluor White, SDS or NaCl

To investigate the effect of gene disruption on cell wall integrity and remodeling, we tested the sensitivity of all csf null mutants to calcofluor white (CW; Fluorescent Brightener 28-Sigma), SDS or NaCl by spotting cells on plates. Exponential cultures were harvested and adjusted to an $OD_{600}$ of 0.24. 2.5 µl of samples plus three to four tenfold serial dilutions were deposited on the surface of YPD plates containing increasing concentrations of the compound: 3-25 µg/ml CW, 1-3 M NaCl, 0.01-0.5% SDS. Growth was monitored after 20 hours incubation at 37° C.

F. Antifungal Susceptibility Assays

Assays were performed at the Center for Medical Mycology, University Hospitals of Cleveland to investigate whether the csf null mutants show a higher susceptibility to antifungals when compared to wild-type. The minimum inhibitory concentrations (MIC) of three antifungal agents, amphotericin B, fluconazole and micafungin, against each fungal isolate were determined according to the NCCLS M27A standard for susceptibility testing of yeasts. Briefly, MIC testing was performed in RPMI 1640 medium at 35° C. for 48 hours and with an inoculum of 0.5-2.5×10$^3$ CFU/ml. The MIC endpoint was defined as the lowest concentration that inhibits 80% of fungal growth as compared to the growth control, for fluconazole and micafungin, and 100% inhibition for amphotericin B.

G. Adhesion Assay

The adhesion assay was based on that described by Cormack et al. (*Science* 285: 578-582, 1999). The purpose of this assay was to determine the ability of *Candida* csf null mutants to adhere to mammalian cells and thus identify new potential cell surface adhesins. Human cell lines of the following types were used: HUVEC endothelial cells, FaDu pharynx carcinoma cells, CCD-18Co normal colon cells, and FHS-74-Int normal intestine cells (all from the ATCC). The mammalian cells were plated in 96-well tissue culture plates at a density of 2×10$^5$ cells/ml in a volume of 200 μl using media from Invitrogen/GIBCO BRL (unless otherwise noted) and supplemented with 10% FBS (Hyclone), penicillin/streptomycin, and HEPES buffer. Culture medium was different for each cell line: HUVEC cells were grown in Ham's F12 supplemented with L-glutamine, non-essential amino acids, heparin (0.1 mg/ml), and endothelial cell growth supplement (0.03 mg/ml; US Biological); FaDu and colon cells were grown in MEM with Earle's BSS supplemented with L-glutamine and non-essential amino acids; FHS-74-Int cells were grown in DMEM supplemented with sodium pyruvate and non-essential amino acids. The human cells were allowed to grow for four days or until a confluent monolayer was formed. The day of the assay, fungal cells were diluted by a factor of 10- to 20-fold from an overnight culture grown in YEPD medium (supplemented if necessary with uridine), and grown an additional two hours in YEPD medium. Fungal cells were diluted to 2×10$^8$ cells/ml in RPMI medium to make a standardized cell suspension for each fungal strain. Human cell monolayers were washed twice with PBS to remove cell growth media and 100 μl of standardized fungal cell suspension was added to each well. The plate was centrifuged at 1500 rpm for 2 min, then incubated for 4 hours at 37° C. The plate was washed four times with PBS to remove nonadherent fungal cells. Mammalian cells were lysed by the addition to each well of 100 μl of 0.1% Triton X100 in PBS, incubation at room temperature for 8 minutes, and resuspension by pipetting. The plates were centrifuged at 2000 rpm for 5 minutes, the supernatant removed by aspiration, and the pellets (including adherent fungal cells) resuspended in 90 μl of PBS. Fungal cells were stained by the addition of 10 μl of FUN-ITM dye (Molecular Probes Inc.) diluted 1:100 in PBS and incubation for 30 minutes at 37° C. in the dark. Plates were read in a fluorescence plate reader at an excitation wavelength of 485 nm and an emission wavelength of 590 nm. Fluorescence readings were compared to pre-assay fungal samples that were incubated at 37° C. for 4 hours and quantitated in the same manner. The percent adhesion was calculated as [(Fluoresence of mammalian cells plus adherent fungal cells)-(Fluoresence of mammalian cells alone)/(Fluoresence of total fungal cells from the pre-assay sample)×100%]. An average percent adhesion was calculated from triplicate samples.

H. Murine Model of Disseminated Candidiasis

The aim of this study is to evaluate the virulence of *Candida albicans* strains in an immunocompetent murine model of a hematogenously disseminated candidiasis. The virulence study is divided into two studies, survival and tissue invasion (fungal burden/histopathology).

Six to eight-week-old female BALB/c mice (20-25 g in weight, Charles River Laboratories, Willmington, Mass.) were housed in the Animal Resource Center (ARC) at Case Western Reserve University. Five mice per *Candida albicans* strains were used in each set of survival experiments. An additional three mice per strains were sacrificed for each set of fungal burden experiments. For survival studies, mice were injected with 0.1 ml of 3×10$^6$ blastospores of *C. albicans* in sterile normal saline via the tail vein. The number of mice surviving in each group as well as any signs of illness was monitored and recorded twice daily for 28 days.

To determine tissue fungal burden, animals were sacrificed 48 h after infection by cervical dislocation. The kidney and brain of each mouse were aseptically removed, weighed, and homogenized in 2 ml of sterile saline solution. The homogenates were then serially diluted, and 1 ml aliquots were cultured on Sabouraud dextrose agar (Difco Laboratories) supplemented with 50 mg/l chloramphenicol (United States Biochemical Corp., Cleveland, Ohio). The number of colony forming units (CFU) was determined after 24-48 h of incubation at 35° C. The tissue fungal burden data was analyzed by Mann-Whitney U Test analysis of the Means. A P value <0.05 was considered statistically significant.

For histopathological studies, sections of the kidney of the sacrificed animals at 48 h were prepared using the standard procedures. Tissue specimens were excised and fixed in 10% neutral buffered formal in, embedded in paraffin, sectioned and then stained with Hematoxylin and Eosin (H & E) and Grocott Methenamine Silver (GMS) stains. Tissues were examined for the presence of fungal elements using light microscopy.

1. Results (a.) Effect of gene disruption on growth, filamentation, cell-wall integrity and antibiotics susceptibility.

Figure 4C:
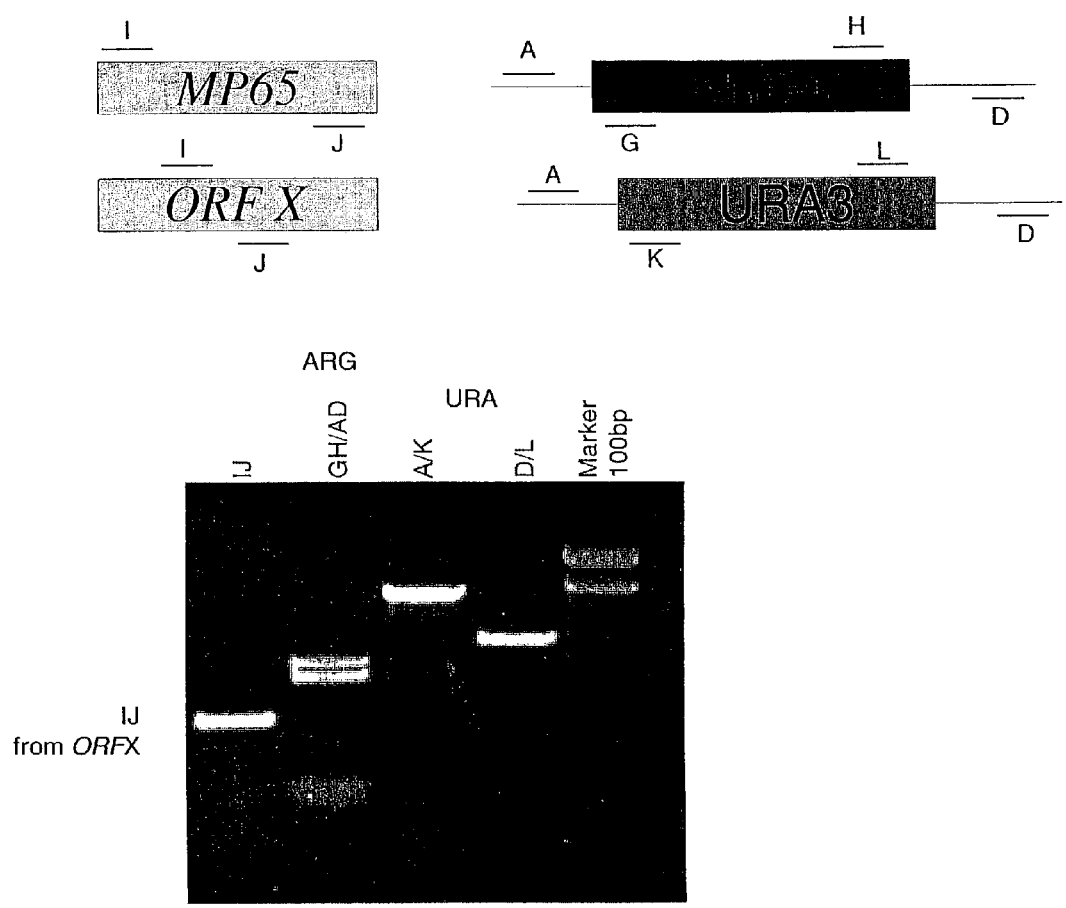
Figure 5:
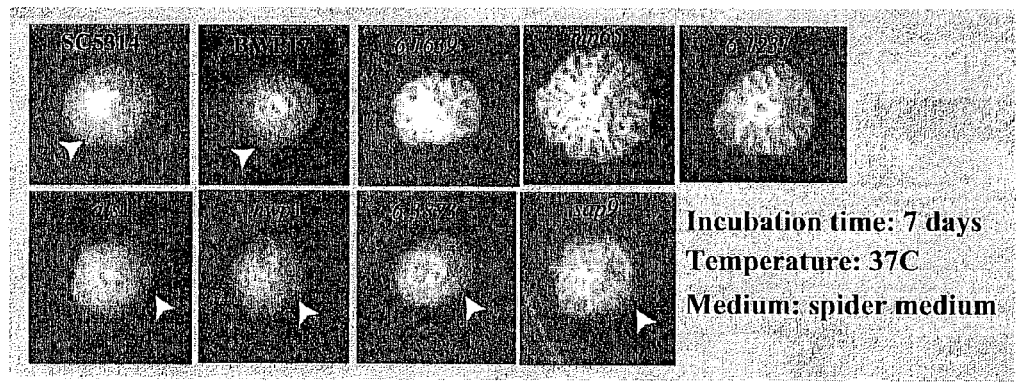
FIG. 5. Filamentation assay on solid medium. A. Blastospores of each fungal isolate including the parental strain (BWP17) and clinical isolate (SC5314) were spotted onto Spider agar plates and incubated for 7 days at 37° C. The white arrow shows the site of invasive growth. These data are summarized in B. Absence of filamentation is indicated by a "–". Successful yeast-to-hyphal transition and invasive growth are indicated by at least one "+".

An example confirming gene disruption in *C. albicans* by 3-way PCR (in this particular case disruption of the MP65 locus) is shown in FIG. 4C. All six mutants were viable indicating that the target genes are not essential for growth. Moreover all mutants showed a wild type like growth rate in full medium at 30° C. suggesting that the loss of the targeted genes do not affect growth rate. A severe defect in filamentation was observed for mp65Δ, 6.1639Δ and 6.1231Δ when the mutant strains were grown for 7 days on spider medium at 37° C. (FIG. 5). Whereas the clinical isolate SC5314 and the parental strain BWP17 were both forming hyphae and invading the agar, all three mutants exhibited only growth on the surface of the agar. Microscopic observation of the colony periphery confirmed the absence of filaments in all three cases. These data suggest a role for MP65, 6.1639 and 6.1231 in filamentation under the conditions tested.

We further characterized the mutants by determining their susceptibility to calcofluor white, SDS and NaCl. Results are summarized in Table 9. The first column contains the name of the strains. Sensitivities to calcofluor, SDS and NaCl are shown in columns 2, 3 and 4. A "+" denotes that the strain was as sensitive as the wild type and more than one "+" indicates that the strain was more sensitive than wild type (cell viability starts to be affected at a lower concentration of compounds). When mp65Δ, 6.1639Δ and sap9Δ were grown in the presence of increasing concentrations of SDS (0-0.5%), they were found to be hypersensitive to SDS after 24 h at 37° C. These increases in SDS sensitivity indicate a cell wall structural defect in the mutants. In addition to hypersensitivity to SDS, mp65Δ was shown to be highly sensitive to calcofluor white. A similar effect was also observed with 6.1231Δ for which no more cells were growing at a concentration of 25 μg/ml calcofluor. In contrast the differences of sensitivity recorded for pra1Δ and 6.3873Δ, were smaller. However these observations may still reflect a slight defect in cell wall integrity for these two mutants. These data confirm the role of all six CSF proteins in fungal cell wall biosynthesis and structure.

To go further in the analysis, we decided to test cells for their ability to respond to hyperosmotic stresses that require cell wall remodeling and integrity. All mutants were grown in the presence of increasing NaCl concentration (0-3M) for 24 h at 37° C. and were found to be as sensitive as the parental strain (Table 9, column 4). This result indicates that response to hyperosmotic stresses is not affected in any of the six csf mutants.

TABLE 9

| Strains | Calcofluor white (CW) sensitivity | SDS sensitivity | NaCl sensitivity |
|---|---|---|---|
| als1 | + | + | + |
| hwp1 | + | + | + |
| mp65 | +++ | +++ | + |
| pra1 | ++ | + | + |
| sap9 | + | +++ | + |
| 6.1639 | + | +++ | + |
| 6.1231 | +++ | ++ | + |
| 6.3873 | ++ | ++ | + |

+: as sensitive as the wild type
more than one +: more sensitive than wild type

In order to investigate more extensively the effects induced by the loss of the targeted genes on the cell wall (e.g. cell wall permeability), we tested whether the mutant strains were more susceptible to antifungal drugs. Three different antifungal agents were tested at Cleaveland: one polyene (Amphotericin B; a compound that binds to ergosterols and increases membrane permeability), one azole (Fluconazole; a compound that interferes with the ergosterol biosynthesis pathway) and one echinochandin (Micafungin; a compound that inhibits the β-glucan synthetase). No differences in MIC were detected. The MIC of amphotericin B against all isolates, including the clinical isolate and parental strain, was 0.5-1 μg/ml. The MIC of fluconazole was 0.25 μg/ml and the MIC of micafungin was 0.008 μg/ml. These data indicate that none of the six CSF proteins are involved directly or indirectly in the mechanism of resistance to antibiotics.

Figure 6A:
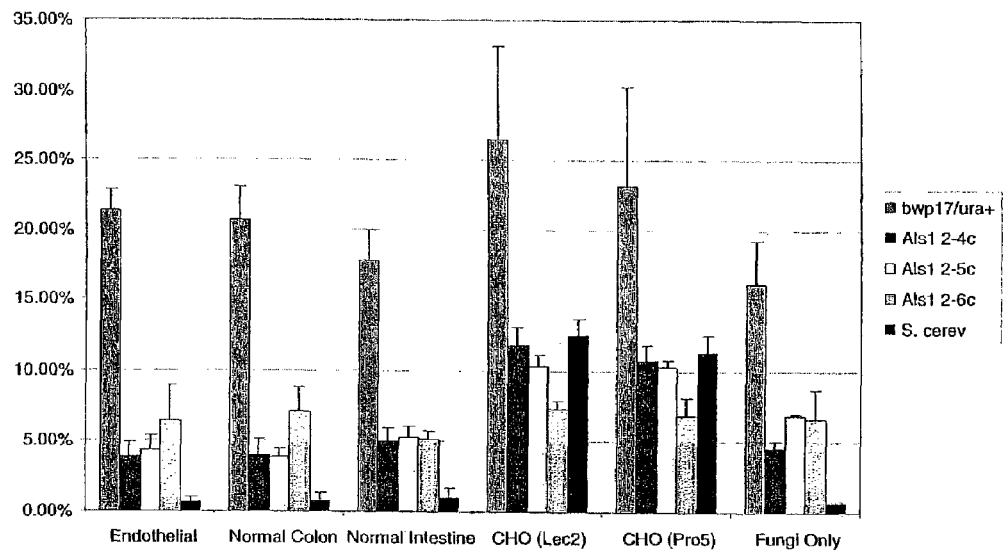
FIGS. 6A-C. Adhesion assay. A. Mammalian cell adherence of BWP17 and als1 null mutant. In that assay *S. cerevisiae* W303A strain was used as a control for non-adherent strain. The percent adhesion was calculated as (Fluoresence of mammalian cells plus adherent fungal cells)–(Fluoresence of mammalian cells alone)/(Fluoresence of total fungal cells from the pre-assay sample)×100%. An average % adhesion was calculated from triplicate samples. B Mammalian cell adherence of BWP17 and hwp1 null mutant. C. Colon and FaDu carcinoma cell adherence of 6.1639Δ and mp65Δ null mutants. In that assay the als1Δ null mutant was used as a control for reduced adherence.
Figure 6B:
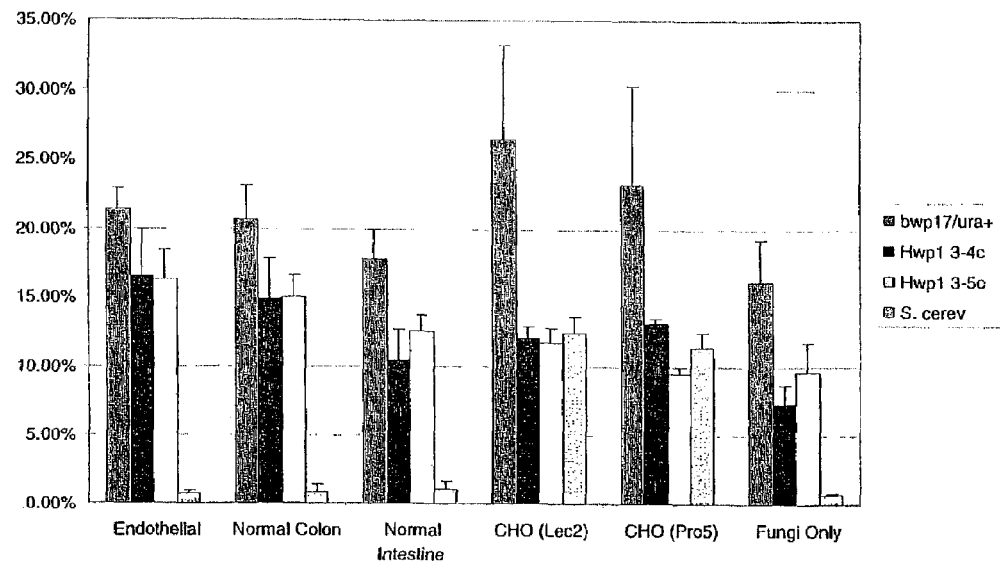
Figure 6C:
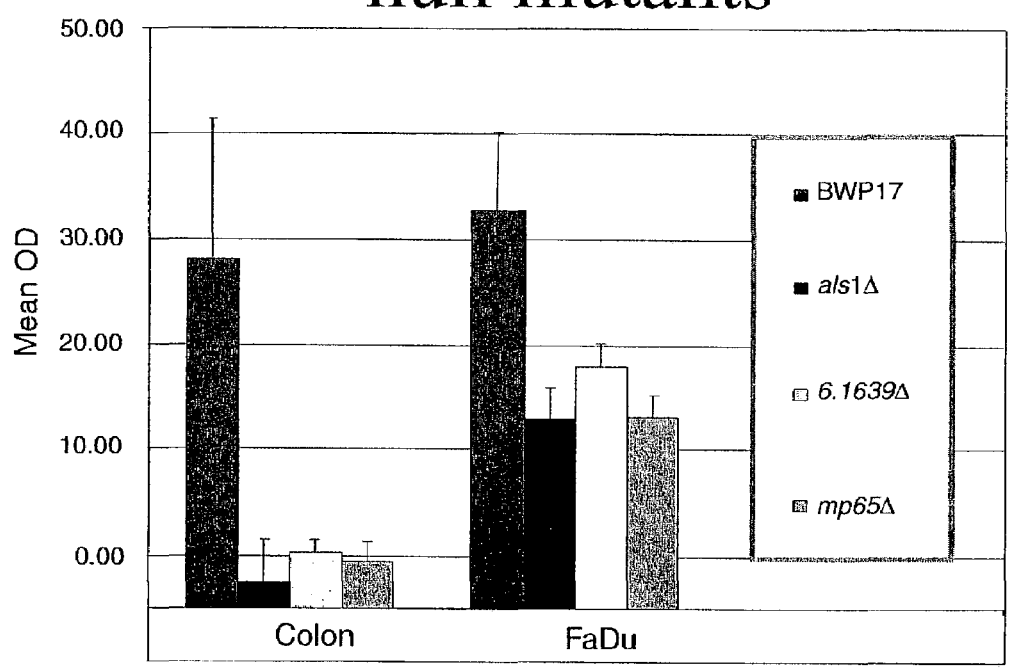

(b.) mp65Δ and 6.1639Δ showed reduced adherence to mammalian cells ALS1 mediates adherence of C. albicans to mammalian cells (Fu, Mol Microbiol, 2002, 44, 61-72). In order to identify additional factors important for adhesion, we performed an in vitro adhesion assay and measured adherence of the six csf mutants to mammalian cells. We also included as controls measurements of the adherence of als1Δ and hwp1Δ mutants. The als1Δ strain showed a significant reduction in adherence (20-50% reduction depending on the cell lines considered; FIG. 6A). In contrast, under the conditions tested, the hwp1Δ mutant showed only a modest effect on adhesion which is restricted to particular cell lines as depicted in FIG. 6B. This result can be explained by the conditions utilized herein which may not be optimal for expression of the HWP1 protein. Interestingly, we measured a noticeable reduction in adherence for two of our csf mutants: mp65Δ and 6.1639Δ. This reduction was comparable to that observed for the als1Δ strain as shown in FIG. 6C. A role for MP65 and 6.1639 in adhesion is of particular interest. By targeting these two proteins we could affect adherence to host tissue and thereby alter virulence.

(c.) Individual deletion of 4 csf genes attenuate C. albicans virulence

Figure 7:
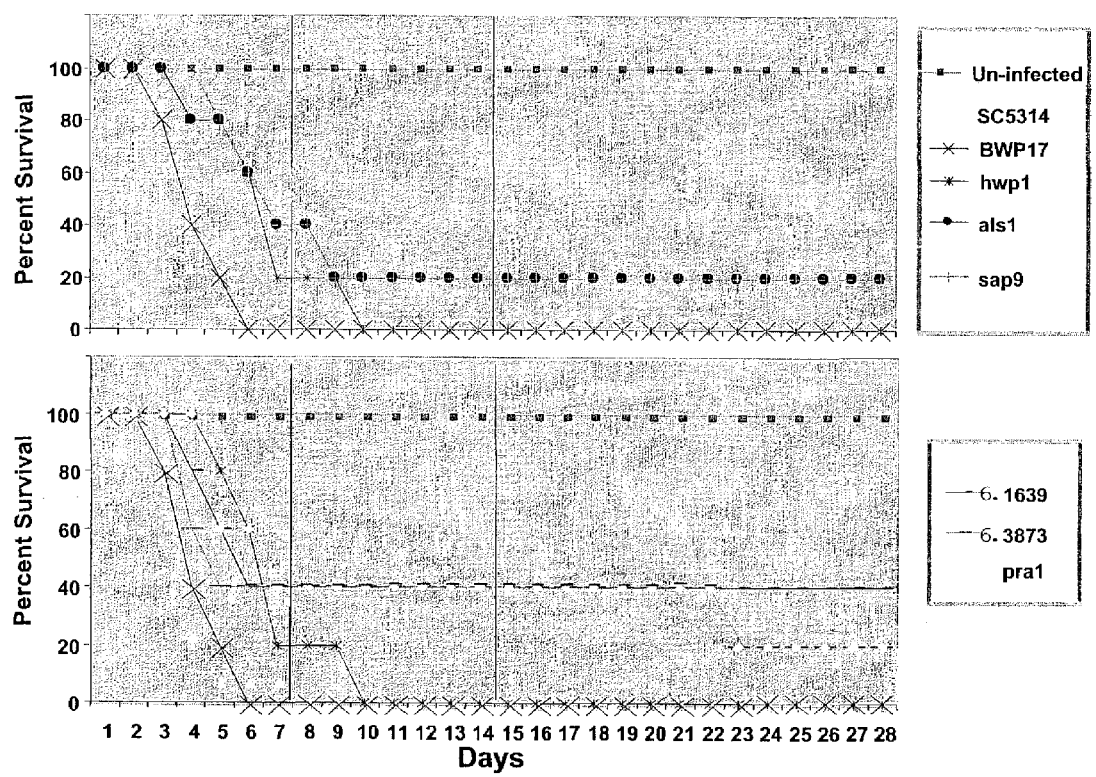
FIG. 7. Graphical representations of the survival data presented in Table 10. For each fungal isolate five mice were injected with 0.1 ml of 3×10$^6$ blastospores and monitored over 28 days for survivors. The percentage survival was calculated as followed: (Number of mice alive at day X)/(Total number of mice at day 0)×100. Survival data were reported on two separate graphs for simplification/clarity.

To determine whether the CSF proteins play a role in pathogenicity, all strains including the clinical isolate, the parental strain, the als1Δ and hwp1Δ mutant strains were tested for virulence in a mouse model of disseminated candidiasis. As already mentioned above, all C. albicans strains tested showed similar growth rate in vitro. Moreover fungal cells were carefully counted and adjusted to the same density before injection. Our survival data are summarized in Table 10. FIG. 7 shows the corresponding survival curves. The 28 days of observation are listed in the first column of Table 10. Each other column represents a group of uninfected (column 2) or infected mice (column 3-10). The number of mice alive in each group was determined and reported every day. No deaths were observed in uninfected control mice during the 28-day study period. At day 7, no survivals were recorded in the group of mice that were infected with SC5314, BWP17 and hwp1Δ. In contrast a prolongation of survival was observed for mice infected with als1Δ, sap9Δ, 6.1639Δ, 6.3873Δ and pra1Δ. At day 14, 40% of the mice infected with 6.1639Δ, 6.3873Δ or pra1Δ were alive against 20% survival recorded for the group of mice infected with als1Δ or sap9Δ. More importantly, at least one mouse in each of these groups was still alive after 28 days of infection.

We did not detect any significant differences in the number of organisms recovered from the kidney and the brains of animals infected with SC5314, BWP17, hwp1Δ, sap9Δ, 6.1639Δ or 6.3873Δ strains. In contrast, kidneys and brains of mice infected with als1Δ mutant contained significantly fewer organisms. A smaller difference in the number of organisms was also detected in the kidneys and brains of mice infected with pra1Δ mutant.

Histopathological examination of the kidneys of mice infected with SC5314 or BWP17 and sacrificed after 48 hours of infection revealed extensive tissue destruction and the presence of multiple foci of proliferating hyphae. Patches of tissue destruction and clustered fungal elements were also observed in the kidney sections obtained from mice infected with hwp1Δ. Tissue invasion was reduced in the kidney sections of all other groups of mice. Interestingly no tissue destruction was observed in kidneys infected with als1Δ mutant. Kidney sections of mice infected with sap9Δ mutant were comparable to kidney sections of als1Δ-infected mice. However, more fungal elements were observed. Finally, kidney sections of mice infected with pra1Δ strain showed not only reduced tissue invasion but also reduced tissue destruction.

TABLE 10

| Day Observed | Un-infected | SC5314 Infected | hwp1Δ- Infected | BWP17- Infected | als1Δ- Infected | sap91Δ-- Infected | 6.1639Δ- Infected | 6.3873Δ- Infected | pra1Δ- Infected |
|---|---|---|---|---|---|---|---|---|---|
| 1 | 9 | 13 | 5 | 5 | 5 | 5 | 5 | 5 | 5 |
| 2 | 9 | 13 | 5 | 5 | 5 | 5 | 5 | 5 | 5 |
| 3 | 9 | 11 | 5 | 4 | 5 | 5 | 5 | 5 | 5 |
| 4 | 9 | 3 | 5 | 2 | 4 | 5 | 4 | 3 | 5 |
| 5 | 9 | 1 | 4 | 1 | 4 | 4 | 3 | 2 | 3 |
| 6 | 9 | 1 | 3 | 0 | 3 | 3 | 2 | 2 | 3 |
| 7 | 9 | 1 | 1 |  | 2 | 2 | 2 | 2 | 2 |
| 8 | 9 | 0 | 1 |  | 2 | 2 | 2 | 2 | 2 |
| 9 | 9 |  | 1 |  | 1 | 1 | 2 | 2 | 2 |
| 10 | 9 |  | 0 |  | 1 | 1 | 2 | 2 | 2 |
| 11 | 9 |  |  |  | 1 | 1 | 2 | 2 | 2 |
| 12 | 9 |  |  |  | 1 | 1 | 2 | 2 | 2 |
| 13 | 9 |  |  |  | 1 | 1 | 2 | 2 | 2 |
| 14 | 9 |  |  |  | 1 | 1 | 2 | 2 | 2 |
| 15 | 9 |  |  |  | 1 | 1 | 2 | 2 | 2 |
| 16 | 9 |  |  |  | 1 | 1 | 2 | 2 | 2 |
| 17 | 9 |  |  |  | 1 | 1 | 2 | 2 | 2 |
| 18 | 9 |  |  |  | 1 | 1 | 2 | 2 | 2 |
| 19 | 9 |  |  |  | 1 | 1 | 2 | 2 | 2 |
| 20 | 9 |  |  |  | 1 | 1 | 2 | 2 | 2 |
| 21 | 9 |  |  |  | 1 | 1 | 2 | 1 | 2 |
| 22 | 9 |  |  |  | 1 | 1 | 2 | 1 | 2 |
| 23 | 9 |  |  |  | 1 | 1 | 2 | 1 | 1 |
| 24 | 9 |  |  |  | 1 | 1 | 2 | 1 | 1 |
| 25 | 9 |  |  |  | 1 | 1 | 2 | 1 | 1 |
| 26 | 9 |  |  |  | 1 | 1 | 2 | 1 | 1 |
| 27 | 9 |  |  |  | 1 | 1 | 2 | 1 | 1 |
| 28 | 9 |  |  |  | 1 | 1 | 2 | 1 | 1 |

IV. Summary

From the six protein targets that we selected from the pool of 210 potential cell surface proteins, we identified two new adhesins and four additional factors that are important for cell wall integrity and virulence. All six proteins are *Candida* cell surface proteins and represent promising targets for the development of new antifungal drugs. In particular, the development of specific antibodies would inhibit their biological activity (e.g adhesion, filamentation) would be useful in the prevention or treatment of candidiasis. In addition, targeting proteins such as the novel factor 6.3873, which shows strong similarity with allergens from other fungal species would be not only useful for the treatment of candidiasis, but also, for the treatment of other serious fungal infections, such as Aspergillosis.

In summary, based on the subset of six cell surface proteins analyzed, all 210 proteins identified using the same method would represent addition therapeutic targets.

All cited patents and publications referred to in this application are herein incorporated by reference in their entirety for all purposes.

EQUIVALENTS

The disclosure of each of the patents, patent applications and publications cited in the specification is hereby incorporated by reference herein in its entirety. Although the invention has been set forth in detail, one skilled in the art will recognize that numerous changes and modifications can be made, and that such changes and modifications may be made without departing from the spirit and scope of the invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07241613B1). An electronic copy of the "Sequence Listing" will also be available from the USPTO upon request and payment of the fee set forth in 37 CFR 1.19(b)(3).

We claim:
1. An isolated polypeptide set forth as SEQ ID NO: 341.
2. A composition for inducing an immune response in a subject comprising an effective amount of the polypeptide of claim 1, an adjuvant and a carrier.

* * * * *